United States Patent [19]

Leinert et al.

[11] Patent Number: 4,612,313

[45] Date of Patent: Sep. 16, 1986

[54] PHARMACEUTICAL PHENYLACETONITRILE DERIVATIVES

[75] Inventors: Herbert Leinert, Heppenheim; Wolfgang Kampe, Heddesheim; Klaus Strein, Hemsbach; Bernd Müller-Beckmann, Grünstadt; Wolfgang Bartsch, Viernheim, all of Fed. Rep. of Germany

[73] Assignee: Boehringer Mannheim GmbH, Mannheim, Fed. Rep. of Germany

[21] Appl. No.: 774,354

[22] Filed: Sep. 10, 1985

[30] Foreign Application Priority Data

Sep. 12, 1984 [DE] Fed. Rep. of Germany ....... 3433383

[51] Int. Cl.$^4$ ................ A61K 31/495; A61K 31/275; C07C 121/80
[52] U.S. Cl. .................... 514/255; 514/330; 514/423; 514/452; 514/466; 514/523; 544/390; 546/226; 548/538; 549/366; 549/435; 549/437; 549/438; 549/441; 549/442; 558/390
[58] Field of Search ............... 558/390; 549/366, 435, 549/437, 438, 441, 442; 544/390; 546/226; 548/538; 514/255, 330, 423, 452, 466, 523

[56] References Cited

U.S. PATENT DOCUMENTS

| 3,261,859 | 7/1966 | Dengel et al. | 558/390 |
| 4,340,603 | 7/1982 | Bodor et al. | 424/301 |
| 4,438,131 | 3/1984 | Ehrmann et al. | 514/523 X |

*Primary Examiner*—Dolph H. Torrence
*Attorney, Agent, or Firm*—Felfe & Lynch

[57] ABSTRACT

The present invention provides phenylacetonitrile derivatives of the general formula:

(I)

wherein $R_1$, $R_2$, $R_3$, $R_4$ and $R_5$, which can be the same or different, are hydrogen or haolgen atoms or alkyl, alkoxy, nitro, amino or acylamino radicals and two adjacent substituents can together also form a methylenedioxy or ethylenedioxy radical, A is a radical of the general formula:

$$-\underset{\underset{R_6}{|}}{\overset{\overset{CN}{|}}{C}}-(CH_2)_m-\underset{\underset{}{|}}{\overset{\overset{R_7}{|}}{N}}-(CH_2)_n- \text{ or } -(CH_2)_n-\underset{\underset{}{|}}{\overset{\overset{R_7}{|}}{N}}-(CH_2)_m-\underset{\underset{R_6}{|}}{\overset{\overset{CN}{|}}{C}}-$$

in which $R_6$ is a straight-chained, cyclic or branched, saturated or unsaturated alkyl radical containing 2 to 12 carbon atoms, $R_7$ is a hydrogen atom or a straight-chained or branched, saturated alkyl radical containing up to 6 carbon atoms, m and n, which can be the same or different, are 2 or 3, p is 1 or 2 and X is a straight-chained, cyclic or branched alkyl radical containing 2 to 10 carbon atoms which is optionally substituted by an amino group or is a grouping of the general formula:

$$-Y-\overset{\overset{O}{\|}}{C}-N\overset{Z}{\underset{Z}{\diagdown}} \text{ or } -Z-NH-\overset{\overset{O}{\|}}{C}-Y$$

(II)           (II')

wherein Y and Z, which can be the same or different, are straight-chained or branched alkyl radicals containing up to 8 carbon atoms or cycloalkyl, alkylcycloalkyl or cycloalkylalkyl radicals, in which these radicals are optionally interrupted by an oxygen or sulphur atom, and one of the groups Z in general formula II can also be a hydrogen atom or both Z groups are joined to form a ring containing 4 to 6 carbon atoms which is optionally interrupted by a further nitrogen atom which can be substituted by alkyl or alkanoyl, the —O—NO$_2$ groups being substituents of Y as well as of Z; as well as the salts thereof with physiologically acceptable acids.

The present invention also provides processes for the preparation of these compounds and pharmaceutical compositions containing them.

23 Claims, No Drawings

PHARMACEUTICAL PHENYLACETONITRILE DERIVATIVES

The present invention is concerned with new phenylacetonitrile derivatives, with processes for the preparation thereof and with pharmaceutical compositions containing them.

Thus, according to the present invention, there are provided new phenylacetonitrile derivatives of the general formula:

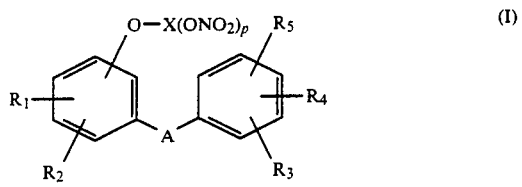

wherein $R_1$, $R_2$, $R_3$, $R_4$ and $R_5$, which can be the same or different, are hydrogen or halogen atoms or alkyl, alkoxy, nitro, amino or acylamino radicals and two adjacent substituents can together also form a methylenedioxy or ethylenedioxy radical, A is a radical of the general formula:

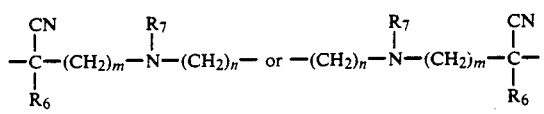

in which $R_6$ is a straight-chained, cyclic or branched, saturated or unsaturated alkyl radical containing 2 to 12 carbon atoms, $R_7$ is a hydrogen atom or a straight-chained or branched, saturated alkyl radical containing up to 6 carbon atoms, m and n, which can be the same or different, are 2 or 3, p is 1 or 2 and X is a straight-chained, cyclic or branched alkyl radical containing 2 to 10 carbon atoms which is optionally substituted by an amino group or is a grouping of the general formula:

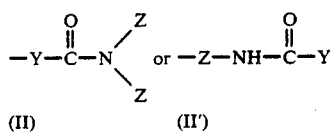

wherein Y and Z, which can be the same or different are straight-chained or branched alkyl radicals containing up to 8 carbon atoms or are cycloalkyl, alkylcycloalkyl or cycloalkylalkyl radicals, in which these radicals are optionally interrupted by an oxygen or sulphur atom, and one of the groups Z in general formula II can also be a hydrogen atom or both Z groups are joined to form a ring containing 4 to 6 carbon atoms which is optionally interrupted by a further nitrogen atom which can be substituted by alkyl or alkanoyl, the —O—NO$_2$ groups being substituents of Y as well as of Z; as well as the salts thereof with physiologically acceptable acids.

The physiologically acceptable acids can be, for example, hydrochloric acid, hydrobromic acid, sulphuric acid, phosphoric acid, acetic acid, malonic acid, succinic acid, fumaric acid, maleic acid, citric acid, tartaric acid, lactic acid, amidosulphonic acid, benzoic acid, oxalic acid, adipic acid, salicylic acid, naphthoic acid or o-acetoxybenzoic acid.

The new compounds according to the present invention contain at least one asymmetric carbon atom. Therefore, the present invention also provides all possible diastereomeric mixtures, racemates and all optically-active forms of the compounds of general formula I.

A number of similar compounds are already known from Federal Republic of Germany Patent Specification No. 11 54 810. However, the compounds of general formula I according to the present invention differ from the there-described compounds in that they contain the grouping —O—X—(ONO$_2$)$_p$ in at least one of the phenyl nuclei.

In comparison with the compounds described in Federal Republic of Germany Patent Specification No. 11 54 810, the compounds of general formula I according to the present invention possess superior pharmacological properties.

Investigations on awake dogs with compounds according to Federal Republic of Germany Patent Specification No. 11 54 810, such as verapamil, show a dosage-dependent decrease of the arterial blood pressure and a dosage-dependent increase of the right atrial pressure, i.e. an after-load decrease but an increase of the pre-load. In contradistinction thereto, the new compounds of general formula I according to the present invention display a dosage-dependent reduction of the arterial blood pressure and also of the atrial pressure and thus of the pre-load. This is to be regarded as being an important therapeutic advantage since a lowering of the pre-load is a recognised effective therapeutic principle in the case of various diseases of the heart-circulatory system, for example in the case of angina pectoris and of cardiac failure.

Furthermore, in vitro investigations on blood vessels show that the compounds of general formula (I), in contradistinction to those of Federal Republic of Germany Patent Specification No. 11 54 810, increase the content of cyclic guanosine monophosphate (c-GMP). According to the views at present held, an increase of the c-GMP content results in a blood vessel relaxation which is an important therapeutic principle in the case of heart-circulatory diseases.

The compounds of general formula I according to the present invention can be prepared, for example, by one of the following methods:

(a) subjecting a compound of the general formula:

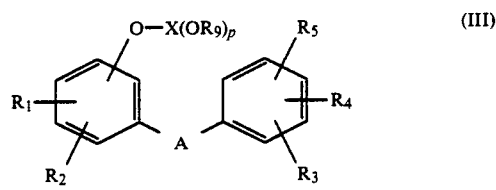

in which $R_1$, $R_2$, $R_3$, $R_4$, $R_5$, A, X and p have the same meanings as above and $R_9$ is a hydrogen atom or a group which can easily be split off, to a nitrate ester formation reaction; or (b) subjecting a compound of the general formula:

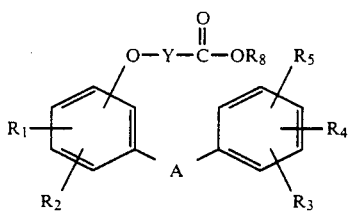

in which $R_1$, $R_2$, $R_3$, $R_4$, $R_5$, A and Y have the same meanings as above and $R_8$ is a hydrogen atom or a lower alkyl radical, to an amide formation reaction with a compound of the general formula:

$$H_2N-Z-(ONO_2)_p \quad (V)$$

in which Z and p have the same meanings as above; or
(c) subjecting a compound of the general formula:

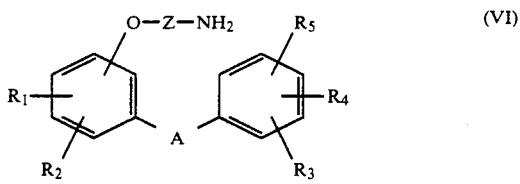

in which $R_1$, $R_2$, $R_3$, $R_4$, $R_5$, A and Z have the same meanings as above, to an amide formation reaction with a compound of the general formula:

in which $R_8$, Y and p have the same meanings as above; whereafter, if desired, the compound obtained is either reacted with an acid to give a corresponding salt or is reacted with a base to liberate a free base therefrom.

Compounds of general formula III are obtained by reacting a compound of general formula IV with a compound of the general formula:

$$H_2N-Z-(OR_9)_p \quad (V')$$

in which Z and p have the same meanings as above and $R_9$ is a hydrogen atom or a protective group which can easily be split off; or by reacting a compound of general formula VI with a compound of the general formula:

in which $R_8$, $R_9$, Y and p have the same meanings as above.

The nitrate ester formation reaction of compounds of general formula III, in which $R_9$ is a hydrogen atom or a protective group which can easily be split off, can be carried out by reaction with a nitrate ester-forming reagent, such as fuming nitric acid and acetic anhydride or a mixture of fuming nitric acid and concentrated sulphuric acid, at a low temperature in the presence or absence of an inert solvent. The reaction temperature is from ambient temperature to −60° C. and preferably from −10° to −30° C. The mole ratio is from 1 to 10.

As protective group $R_9$, there are preferably used ester groups which, under the acidic conditions of the nitration reaction, are easily split off or exchanged for the nitrate group. Preferred protective groups include the benzoyloxy, alkoxycarbonyl, alkanoyl and sulphonyl groups. Groups which are split off under basic conditions must possibly be removed in a preceding reaction.

Alternatively, the nitrate ester formation reaction can also be carried out in that, in a compound of general formula III, wherein $R_9$ is a hydrogen atom or an active ester or a sulphonyl group, the group $OR_9$ is halogenated and the reaction product is subsequently reacted with silver nitrate in the presence or absence of a solvent at a temperature of from ambient temperature to 100° C.

The halogenation reaction can be carried out by processes known from the literature by reacting a compound of general formula III with mesyl chloride or tosyl chloride in the presence of an acid-binding agent and subsequently the reaction product is reacted with an alkali metal halide in an organic solvent, for example dimethylformamide. The mole ratio of the mixture reaction between the halogen compound and silver nitrate is not critical. It can be from 1 to 10. This reaction is also usually carried out at a temperature of from 20° to 100° C.

The amide formation reaction of a compound of general formula IV with a compound of general formula V can be carried out by reacting the two compounds in an inert solvent, for example tetrahydrofuran, dioxan, dimethylformamide or methylene chloride, when $R_8$ in general formula IV is a lower alkyl radical. The reaction can be carried out at a temperature of from ambient temperature to 100° C., the reaction period can be from 1 to 10 hours and the mole ratio of the reactants can be from 1 to 3.

When $R_8$ in general formula IV is a hydrogen atom, the amide formation reaction with a compound of general formula V can be carried out with the help of a coupling reagent, for example dicyclohexylcarbodiimide or carbonyldiimidazole, or by converting the carboxyl group in a compound of general formula IV into an activated carboxylic acid derivative, for example a carboxylic acid halide or mixed anhydride, by means of known processes. As solvents, there can be used inert organic solvents, for example, tetrahydrofuran, dioxan, dimethylformamide or methyl chloride. The reaction temperature is from −30° to +50° C., the reaction time is from 30 minutes to 10 hours and the mole ratio of the reactants can be from 1 to 5.

The amide formation reaction of a compound of general formula IV with a compound of general formula V' can be carried out by reacting the two compounds directly or in an inert solvent, for example tetrahydrofuran, dioxan, dimethylformamide or methylene chloride, for the case in which $R_8$ in general formula IV is a lower alkyl radical and $R_9$ in general formula V' is a hydrogen atom or a protective group. The reaction can be carried out between ambient temperature and 100° C., the reaction time can be from 1 to 10 hours and the mole ratio of the reactants can be from 1 to 3.

When $R_8$ in general formula IV is a hydrogen atom, the amide formation reaction can be carried out with a compound of general formula V' with the help of a coupling reagent, for example dicyclohexylcarbodiimide or carbonyldiimidazole, or by conversion of the carboxyl group in a compound of general formula IV into an activated carboxylic acid derivative, for example a carboxylic acid halide or mixed anhydride, for example a halogenoformic acid ester, by means of known methods. As solvents, there can be used inert organic solvents, for example tetrahydrofuran, dioxan, dimethylformamide or methylene chloride. The reaction temperature is from −30° to +50° C., the reaction time is from 30 minutes to 10 hours and the mole ratio of the reactants can be from 1 to 5.

The amide formation reaction of a compound of general formula VII or VII' with a compound of general formula VI can, in principle, be carried out by the same processes such as are carried out in the case of the described amide formation reactions from a compound of general formula IV with a compound of the general formula V or V'.

The compounds of general formulae III, IV and VI can be prepared by reacting a compound of the general formula:

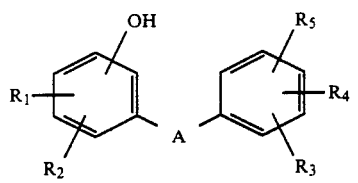
(VIII)

in which $R_1$, $R_2$, $R_3$, $R_4$, $R_5$ and A have the same meanings as above, by known processes with a compound of the general formula:

Hal—X'—W (IX)

in which Hal is a halogen atom, such as chlorine or bromine, X' is a straight-chained or branched alkyl radical containing up to 8 carbon atoms, which is optionally substituted by an amino group, and W is a hydroxyl, amino, carboxyl or carbalkoxy group or a grouping which can subsequently be converted thereinto or a carbon atom from X' and W can together form an epoxide ring.

The compounds of general formula VIII can be prepared, for example, by reacting a compound of the general formula:

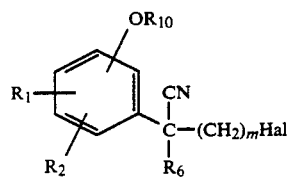
(X)

with a compound of the general formula:

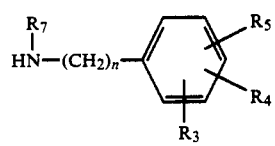
(XI)

in which $R_1$, $R_2$, $R_6$, Hal and m have the same meanings as above and $R_{10}$ is a benzyl radical, with a compound of the general formula:

in which $R_3$, $R_4$, $R_5$, $R_7$ and n have the same meanings as above, according to known processes, whereafter the benzyl radical is split off hydrogenolytically.

The compounds of general formula VIII can also be prepared by reacting a compound of the general formula:

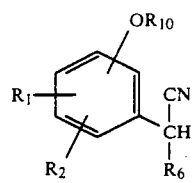
(XII)

in which $R_1$, $R_2$, $R_6$ and $R_{10}$ have the same meanings as above, with a compound of the general formula:

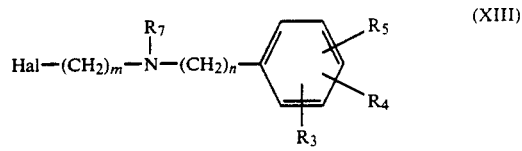
(XIII)

in which $R_3$, $R_4$, $R_5$, $R_7$, Hal, m and n have the same meanings as above, whereafter the benzyl radical is split off hydrogenolytically.

The compounds of general formula III, IV, VI and VIII are new and some of them are also pharmacologically active.

The preparation of the compound of general formula X takes place analogously to known processes, for example by reaction of a compound of general formula XII with a compound of the general formula:

Hal(CH₂)ₘHal (XIV)

wherein m has the same meaning as above and Hal is a chlorine or bromine atom, with the help of a phase transfer-catalysed reaction. The catalyst used can be, for example, a quaternary ammonium or phosphonium salt or a crown ether.

The preparation of compounds of general formula XII also takes place analogously to known processes, for example by reaction of a compound of the general formula:

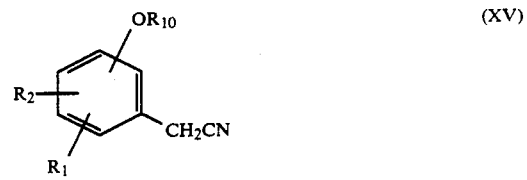
(XV)

wherein $R_1$, $R_2$ and $R_{10}$ have the same meanings as above, with a compound of the general formula:

$R_6$—Hal (XVI)

wherein $R_6$ and Hal have the same meanings as above, with the help of a phase transfer-catalysed reaction. As catalyst, there can be used a quaternary ammonium or phosphonium salt or a crown ether.

Halogen means, according to the present invention, fluorine, chlorine, bromine and iodine, fluorine and chlorine being preferred.

Alkyl, also in alkoxy, means, insofar as it is not otherwise defined, a radical containing up to 6 carbon atoms, the methyl, ethyl, n-propyl, isopropyl and butyl radicals being preferred.

By cyclic alkyl radicals are to be understood mono- and dicycles, especially cyclopropyl, cyclopentyl and cyclohexyl radicals.

Especially preferred are compounds in which A in general formula I is the radical:

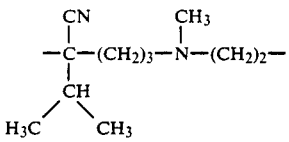

By acylamino radicals are to be understood alkanoylamino radicals containing up to 6 carbon atoms, formyl and acetylamino being especially preferred.

The new compounds of general formula I according to the present invention and the salts thereof can be administered enterally and parenterally in liquid or solid form. As injection medium, it is preferred to use water which contains the conventional additives for injection solutions, such as stabilisers, solubilisers and buffers. Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening materials.

The compounds according to the present invention are usually administered in amounts of from 50 to 500 mg. per day, referred to a body weight of 75 kg. It is preferred to administer, 2 to 3 times a day, 1 to 2 tablets with an active material content of 20 to 200 mg. The tablets can also be retarded in which case only 1 to 2 tablets containing 50 to 500 mg. of active material are given once per day. The active material can also be administered by injection 1 to 8 times a day or by continuous infusion, amounts of from 10 to 200 mg./day thereby usually being sufficient.

Preferred compounds according to the present invention include the following:

2-methoxy-4-{1-cyano-1-(methylethyl)-4-[N-methyl-N-[2-(3,4-dimethoxyphenyl)-ethyl]-aminobutyl]}-phenoxy-N-(3-nitrooxypropyl-1)-acetamide 2-methoxy-4-{1-cyano-1-(methylethyl)-4-[N-methyl-N-[2-(3,4-dimethoxyphenyl)-ethyl]-aminobutyl]}-phenoxyacetic acid 4-(nitrooxymethyl)-piperidylamide 2-methoxy-4-{1-cyano-1-(methylethyl)-4-[N-methyl-N-[2-(3,4-dimethoxyphenyl)-ethyl]-aminobutyl]}-phenoxyacetic acid 4-(α-nitrooxyethyl)-piperidylamide 2-methoxy-4-{1-cyano-1-(methylethyl)-4-[N-methyl-N-[2-(3,4-dimethoxyphenyl)-ethyl]-aminobutyl]}-phenoxy-N-(4-methyl-3-nitrooxypentyl-2)-acetamide 2-methoxy-4-{1-cyano-1-(methylethyl)-4-[N-methyl-N-[2-(3,4-dimethoxyphenyl)-ethyl]-aminobutyl]}-phenoxy-N-(4,4-dimethyl-3-nitrooxypentyl-2)-acetamide 2-methoxy-4-{1-cyano-1-(methylethyl)-4-[N-methyl-N-[2-(3,4-dimethoxyphenyl)-ethyl]-aminobutyl]}-phenoxy-N-(2,4-dimethyl-3-nitrooxypentyl-2)-acetamide 2-methoxy-4-{1-cyano-1-(methylethyl)-4-[N-methyl-N-[2-(3,4-dimethoxyphenyl)-ethyl]-aminobutyl]}-phenoxy-N-(2,4,4-trimethyl-3-nitrooxypentyl-2)-acetamide 2-methoxy-4-{1-cyano-1-(methylethyl)-4-[N-methyl-N-[2-(3,4-dimethoxyphenyl)-ethyl]-aminobutyl]}-phenoxy-N-(2,2-dimethyl-3-nitrooxypropyl-1)-acetamide 2-chloro-3-ethyl-4-{1-cyano-1-(methylethyl)-3-[N-methyl-N-[2-(3,4-dimethylphenyl)-ethyl]-aminopropyl]}-phenoxy-N-(3-nitrooxypropyl-1)-acetamide 2-methoxy-5-{1-cyano-1-(methylethyl)-4-[N-methyl-N-[2-(3,4-dimethoxyphenyl)-ethyl]-aminobutyl]}-phenoxy-N-(3-nitrooxypropyl-1)-acetamide 2-methoxy-5-{1-cyano-1-(methylethyl)-4-[N-methyl-N-[2-(3,4-dimethoxyphenyl)-ethyl]-aminobutyl]}-phenoxyacetic acid 4-(nitrooxymethyl)-piperidylamide 2-methoxy-5-{1-cyano-1-(methylethyl)-4-[N-methyl-N-[2-(3,4-dimethoxyphenyl)-ethyl]-aminobutyl]}-phenoxyacetic acid 4-(α-nitrooxyethyl)-piperidylamide 2-methoxy-5-{1-cyano-1-(methylethyl)-4-[N-methyl-N-[2-(3,4-dimethoxyphenyl)-ethyl]-aminobutyl]}-phenoxy-N-(4-methyl-3-nitrooxypentyl-2)-acetamide 2-methoxy-5-{1-cyano-1-(methylethyl)-4-[N-methyl-N-[2-(3,4-dimethoxyphenyl)-ethyl]-aminobutyl]}-phenoxy-N-(4,4-dimethyl-3-nitrooxypentyl-2)-acetamide 2-methoxy-5-{1-cyano-1-(methylethyl)-4-[N-methyl-N-[2-(3,4-dimethoxyphenyl)-ethyl]-aminobutyl]}-phenoxy-N-(2,4-dimethyl-3-nitrooxypentyl-2)-acetamide 2-methoxy-5-{1-cyano-1-(methylethyl)-4-[N-methyl-N-[2-(3,4-dimethoxyphenyl)-ethyl]-aminobutyl]}-phenoxy-N-(2,4,4-trimethyl-3-nitrooxypentyl-2)-acetamide 2-methoxy-5-{1-cyano-1-(methylethyl)-4-[N-methyl-N-[2-(3,4-dimethoxyphenyl)-ethyl]-aminobutyl]}-phenoxy-N-(2,2-dimethyl-3-nitrooxypropyl-1)-acetamide 2-methoxy-5-{1-cyano-1-(cyclohexyl)-4-[N-ethyl-N-[2-(3,4-methylenedioxyphenyl)-ethyl]-aminobutyl]}-phenoxy-N-(3-nitrooxypropyl-1)-acetamide 2-methoxy-4-{2-[N-methyl-N-[4-cyano-4-(methylethyl)-4-(3,4-dimethoxyphenyl)-butyl]-aminoethyl]}-phenoxy-N-(3-nitrooxypropyl-1)-acetamide 2-methoxy-4-{2-[N-methyl-N-[4-cyano-4-(methylethyl)-4-(3,4-dimethoxyphenyl)-butyl]-aminoethyl]}-phenoxyacetic acid 4-(nitrooxymethyl)-piperidylamide 2-methoxy-4-{2-[N-methyl-N-[4-cyano-4-(methylethyl)-4-(3,4-dimethoxyphenyl)-butyl]-aminoethyl]}-phenoxyacetic acid 4-(α-nitrooxyethyl)-piperidylamide 2-methoxy-4-{2-[N-methyl-N-[4-cyano-4-(methylethyl)-4-(3,4-dimethoxyphenyl)-butyl]-aminoethyl]}-phenoxy-N-(4-methyl-3-nitrooxypentyl-2)-acetamide 2-methoxy-4-{2-[N-methyl-N-[4-cyano-4-(methylethyl)-4-(3,4-dimethoxyphenyl)-butyl]-aminoethyl]}-phenoxy-N-(4,4-dimethyl-3-nitrooxypentyl-2)-acetamide 2-methoxy-4-{2-[N-methyl-N-[4-cyano-4-(methylethyl)-4-(3,4-dimethoxyphenyl)-butyl]-aminoethyl]}-phenoxy-N-(2,4-dimethyl-3-nitrooxypentyl-2)-acetamide 2-methoxy-4-{2-[N-methyl-N-[4-cyano-4-(methylethyl)-4-(3,4-dimethoxyphenyl)-butyl]-aminoethyl]}-phenoxy-N-(2,4,4-trimethyl-3-nitrooxypentyl-2)-acetamide 2-methoxy-4-{2-[N-methyl-N-[4-cyano-4-(methylethyl)-4-(3,4-dimethoxyphenyl)-butyl]-aminoethyl]}-phenoxy-N-(2,2-dimethyl-3-nitrooxypropyl-1)-acetamide 2-propoxy-4-{2-N-[4-cyano-4-(methylethyl)-4-(4-fluorophenyl)-butyl]-aminoethyl}-phenoxy-(2-nitrooxyethyl-1)-acetamide 2-methoxy-5-{2-[N-methyl-N-[4-cyano-4-(methylethyl)-4-(3,4-dimethoxyphenyl)-butyl]-aminoethyl]}-phenoxy-N-(3-nitrooxypropyl-1)-acetamide 2-methoxy-5-{2-[N-methyl-N-[4-cyano-4-(methylethyl)-4-(3,4-dimethoxyphenyl)-butyl]-aminoethyl]}-phenoxyacetic acid 4-(nitrooxymethyl)-piperidylamide 2-methoxy-5-{2-[N-methyl-N-[4-cyano-4-(methylethyl)-4-(3,4-dimethoxyphenyl)-butyl]-aminoethyl]}-phenoxyacetic acid 4-(α-nitrooxyethyl)-piperidylamide 2-methoxy-5-{2-[N-methyl-N-[4-cyano-4-(methylethyl)-4-(3,4-dimethoxyphenyl)-butyl]-aminoethyl]}-phenoxy-N-(4-methyl-3-nitrooxypentyl-2)-acetamide 2-methoxy-5-{2-[N-methyl-N-[4-cyano-4-(methylethyl)-4-(3,4-dimethoxyphenyl)-butyl]-aminoethyl]}-phenoxy-N-(4,4-dimethyl-3-nitrooxypentyl-2)-acetamide 2-methoxy-5-{2-[N-methyl-N-[4-cyano-4-(methylethyl)-4-(3,4-dimethoxyphenyl)-butyl]-aminoethyl]}-phenoxy-N-(2,4-dimethyl-3-nitrooxypentyl-2)-acetamide 2-methoxy-5-{2-[N-methyl-N-[4-cyano-4-(methylethyl)-4-(3,4-dimethoxyphenyl)-butyl]-aminoethyl]}-phenoxy-N-(2,4,4-trimethyl-3-nitrooxypentyl-2)-acetamide 2-methoxy-5-{2-[N-methyl-N-[4-cyano-4-(methylethyl)-4-(3,4-dimethoxyphenyl)-butyl]-aminoethyl]}-phenoxy-N-(2,2-dimethyl-3-nitrooxypropyl-1)-acetamide 2-methoxy-4-{2-[N-methyl-N-[4-cyano-4-(methylethyl)-4-(3-nitro-4-methoxyphenyl)-butyl]-aminoethyl]}-phenoxy-N-(2-nitrooxtpropyl-1)-acetamide 2-methoxy-4-{2-(N-methyl-N-[4-cyano-4-(methylethyl)-4-(3-amino-4-methoxyphenyl)-butyl]-aminoethyl]}-phenoxy-N-(2-nitrooxypropyl-1)-acetamide 2-methoxy-4-{2-[N-methyl-N-[4-cyano-4-(methylethyl)-4-(3-acetamide-4-methoxyphenyl)-butyl]-aminoethyl]}-phenoxy-N-(2-nitrooxypropyl-1)-acetamide 2-methoxy-5-{2-[N-methyl-N-[4-cyano-4-(methylethyl)-4-(3,4,5-trimethoxyphenyl)-butyl]-aminoethyl]}-phenoxy-N-(nitrooxyethyl)-acetamide 2-methoxy-5-{2-[N-methyl-N-[4-cyano-4-(methylethyl)-4-(3,4,5-trimethoxyphenyl)-butyl]-aminoethyl]}-phenoxy-N-(2-nitrooxypropyl)-acetamide 2-methoxy-5-{2-[N-methyl-N-[4-cyano-4-(methylethyl)-4-(3,4,5-trimethoxyphenyl)-butyl]-aminoethyl]}-phenoxy-N-(3-nitrooxybutyl-2)-acetamide 2-methoxy-5-{2-[N-methyl-N-[4-cyano-4-(methylethyl)-4-(3,4,5-trimethoxyphenyl)-butyl]-aminoethyl]}-phenoxy-N-(2-methyl-3-nitrooxypropyl-2)-acetamide 2-methoxy-5-{2-[N-methyl-N-[4-cyano-4-(methylethyl)-4-(3,4,5-trimethoxyphenyl)-butyl]-aminoethyl]}-phenoxy-N-(1,3-bis-nitrooxycyclohexyl-2)-acetamide 2-methoxy-5-{2-[N-methyl-N-[4-cyano-4-(methylethyl)-4-(3,4,5-trimethoxyphenyl)-butyl]-aminoethyl]}-phenoxy-N-(3-nitrooxypropyl-1)-acetamide 2-methoxy-5-{2-[N-methyl-M-[4-cyano-4-(methylethyl)-4-(3,4,5-trimethoxyphenyl)-butyl]-aminoethyl]}-phenoxyacetic acid 4-(nitrooxymethyl)-piperidylamide 2-methoxy-5-{2-[N-methyl-N-[4-cyano-4-(methylethyl)-4-(3,4,5-trimethoxyphenyl)-butyl]-aminoethyl]}-phenoxyacetic acid 4-(α-nitrooxyethyl)-piperidylamide 2-methoxy-5-{2-[N-methyl-N-[4-cyano-4-(methylethyl)-4-(3,4,5-trimethoxyphenyl)-butyl]-aminoethyl]}-phenoxy-N-(4-methyl-3-nitrooxypentyl-2)-acetamide 2-methoxy-5-{2-[N-methyl-N-[4-cyano-4-(methylethyl)-4-(3,4,5-trimethoxyphenyl)-butyl]-aminoethyl]}-phenoxy-N-(4,4-dimethyl-3-nitrooxypentyl-2)-acetamide 2-methoxy-5-{2-[N-methyl-N-[4-cyano-4-(methylethyl)-4-(3,4,5-trimethoxyphenyl)-butyl]-aminoethyl]}-phenoxy-N-(2,4-dimethyl-3-nitrooxypentyl-2)-acetamide 2-methoxy-5-{2-[N-methyl-N-[4-cyano-4-(methylethyl)-4-(3,4,5-trimethoxyphenyl)-butyl]-aminoethyl]}-phenoxy-N-(2,4,4-trimethyl-3-nitrooxypentyl-2)-acetamide 2-methoxy-5-{2-[N-methyl-N-[4-cyano-4-(methylethyl)-4-(3,4,5-trimethoxyphenyl)-butyl]-aminoethyl]}-phenoxy-N-(2,2-dimethyl-3-nitrooxypropyl-1)-acetamide 2-methoxy-4-{2-[N-methyl-N-[4-cyano-4-(methylethyl)-4-(3,4,5-trimethoxyphenyl)-butyl]-aminoethyl]}-phenoxy-N-(3-nitrooxypropyl-1)-acetamide 2-methoxy-4-{2-[N-methyl-N-[4-cyano-4-(methylethyl)-4-(3,4,5-trimethoxyphenyl)-butyl]-aminoethyl]}-phenoxy-acetic acid 4-(nitrooxymethyl)-piperidylamide 2-methoxy-4-{2-[N-methyl-N-[4-cyano-4-(methylethyl)-4-(3,4,5-trimethoxyphenyl)-butyl]-aminoethyl]}-phenoxyacetic acid 4-(α-nitrooxyethyl)-piperidylamide 2-methoxy-4-{2-[N-methyl-N-[4-cyano-4-(methylethyl)-4-(3,4,5-trimethoxyphenyl)-butyl]-aminoethyl]}-phenoxy-N-(4-methyl-3-nitrooxypentyl-2)-acetamide 2-methoxy-4-{2-[N-methyl-N-[4-cyano-4-(methylethyl)-4-(3,4,5-trimethoxyphenyl)-butyl]-aminoethyl]}-phenoxy-N-(4,4-dimethyl-3-nitrooxypentyl-2)-acetamide 2-methoxy-4-{2-[N-methyl-N-[4-cyano-4-(methylethyl)-4-(3,4,5-trimethoxyphenyl)-butyl]-aminoethyl]}-phenoxy-N-(2,4-dimethyl-3-nitrooxypentyl-2)-acetamide 2-methoxy-4-{2-[N-methyl-N-[4-cyano-4-(methylethyl)-4-(3,4,5-trimethoxyphenyl)-butyl]-aminoethyl]}-phenoxy-N-(2,4,4-trimethyl-3-nitrooxypentyl-2)-acetamide 2-methoxy-4-{2-[N-methyl-N-[4-cyano-4-(methylethyl)-4-(3,4,5-trimethoxyphenyl)-butyl]-aminoethyl]}-phenoxy-N-(2,2-dimethyl-3-nitrooxypropyl-1)-acetamide 3-{2-[N-methyl-N-[4-cyano-4-dodecyl-4-(3,4,5-trimethoxyphenyl)-butyl]-aminoethyl]}-phenoxy-N-(2-nitrooxypropyl)-acetamide 3-{2-[N-methyl-N-[4-cyano-4-dodecyl-4-(3,4,5-trimethoxyphenyl)-butyl]-aminoethyl]}-phenoxy-N-(3-nitrooxybutyl-2)-acetamide 3-{2-[N-methyl-N-[4-cyano-4-dodecyl-4-(3,4,5-trimethoxyphenyl)-butyl]-aminoethyl]}-phenoxy-N-(3-nitrooxypropyl-1)-acetamide 3-{2-[N-methyl-N-[4-cyano-4-dodecyl-4-(3,4,5-trimethoxyphenyl)-butyl]-aminoethyl]}-phenoxyacetic acid 4-(nitrooxymethyl)-piperidylamide 3-{2-[N-methyl-N-[4-cyano-4-dodecyl-4-(3,4,5-trimethoxyphenyl)-butyl]-aminoethyl]}-phenoxyacetic acid 4-(α-nitrooxyethyl)-piperidylamide 3-{2-[N-methyl-N-[4-cyano-4-dodecyl-4-(3,4,5-trimethoxyphenyl)-butyl]-aminoethyl]}-phenoxy-N-(4-methyl-3-nitrooxypentyl-2)-acetamide 3-{2-[N-methyl-N-[4-cyano-4-dodecyl-4-(3,4,5-trimethoxyphenyl)-butyl]-aminoethyl]}-phenoxy-N-(4,4-dimethyl-3-nitrooxypentyl-2)-acetamide 3-{2-[N-methyl-N-[4-cyano-4-dodecyl-4-(3,4,5-trimethoxyphenyl)-butyl]-aminoethyl]}-phenoxy-N-(2,4-dimethyl-3-nitrooxypentyl-2)-acetamide 3-{2-[N-methyl-N-[4-cyano-4-dodecyl-4-(3,4,5-trimethoxyphenyl)-butyl]-aminoethyl]}-phenoxy-N-(2,4,4-trimethyl-3-nitrooxypentyl-2)-acetamide 3-{2-[N-methyl-N-[4-cyano-4-dodecyl-4-(3,4,5-trimethoxyphenyl)-butyl]-aminoethyl]}-phenoxy-N-(2,2-dimethyl-3-nitrooxypropyl-1)-acetamide 4-{2-[N-methyl-N-[4-cyano-4-dodecyl-4-(3,4,5-trimethoxyphenyl)-butyl]-aminoethyl]}-phenoxy-N-(nitrooxyethyl)-acetamide 4-{2-[N-methyl-N-[4-cyano-4-dodecyl-4-(3,4,5-trimethoxyphenyl)-butyl]-aminoethyl]}-phenoxy-N-(2-nitrooxypropyl)-acetamide 4-{2-[N-methyl-N-[4-cyano-4-dodecyl-4-(3,4,5-trimethoxyphenyl)-butyl]-aminoethyl]}-phenoxy-N-(3-nitrooxybutyl-2)-acetamide 4-{2-[N-methyl-N-[4-cyano-4-dodecyl-4-(3,4,5-trimethoxyphenyl)-butyl]-aminoethyl]}-phenoxy-N-(3-nitrooxypropyl-1)-acetamide 4-{2-[N-methyl-N-[4-cyano-4-dodecyl-4-(3,4,5-trimethoxyphenyl)-butyl]-aminoethyl]}-phenoxyacetic acid-4-(nitrooxymethyl)-piperidylamide 4-{2-[N-methyl-N-[4-cyano-4-dodecyl-4-(3,4,5-trimethoxyphenyl)-butyl]-aminoethyl]}-phenoxyacetic acid 4-(α-nitrooxyethyl)-piperidylamide 4-{2-[N-methyl-N-[4-cyano-4-dodecyl-4-(3,4,5-trimethoxyphenyl)-butyl]-aminoethyl]}-phenoxy-N-(4-methyl-3-nitrooxypentyl-2)-acetamide 4-{2-[N-methyl-N-[4-cyano-4-dodecyl-4-(3,4,5-trimethoxyphenyl)-butyl]-aminoethyl]}-phenoxy-N-(4,4-dimethyl-3-nitrooxypentyl-2)-acetamide 4-{2-[N-methyl-N-[4-cyano-4-dodecyl-4-(3,4,5-trimethoxyphenyl)-butyl]-aminoethyl]}-phenoxy-N-(2,4-dimethyl-3-nitrooxypentyl-2)-acetamide 4-{2-[N-methyl-N-[4-cyano-4-dodecyl-4-(3,4,5-trimethoxyphenyl)-butyl]-aminoethyl]}-phenoxy-N-(2,4,4-trimethyl-3-nitrooxypentyl-2)-acetamide 4-{2-[N-methyl-N-[4-cyano-4-dodecyl-4-(3,4,5-trimethoxyphenyl)-butyl]-aminoethyl]}-phenoxy-N-(2,2-dimethyl-3-nitrooxypropyl-1)-acetamide 3-{2-[N-methyl-N-[4-cyano-4-dodecyl-4-(3,4-dimethoxyphenyl)-butyl]-aminoethyl]}-phenoxy-N-(3-nitrooxybutyl-2)-acetamide 3-{2-[N-methyl-N-[4-cyano-4-dodecyl-4-(3,4-dimethoxyphenyl)-butyl]-aminoethyl]}-phenoxy-N-(3-nitrooxypropyl-1)-acetamide 3-{2-[N-methyl-N-[4-cyano-4-dodecyl-4-(3,4-dimethoxyphenyl)-butyl]-aminoethyl]}-phenoxyacetic acid 4-(nitrooxymethyl)-piperidylamide 3-{2-[N-methyl-N-[4-cyano-4-dodecyl-4-(3,4-dimethoxyphenyl)-butyl]-aminoethyl]}-phenoxyacetic acid 4-(α-nitrooxyethyl)-piperidylamide 3-{2-[N-methyl-N-[4-cyano-4-dodecyl-4-(3,4-dimethoxyphenyl)-butyl]-aminoethyl]}-phenoxy-N-(4-methyl-3-nitrooxypentyl-2)-acetamide 3-{2-[N-methyl-N-[4-cyano-4-dodecyl-4-(3,4-dimethoxyphenyl)-butyl]-aminoethyl]}-phenoxy-N-(4,4-dimethyl-3-nitrooxypentyl-2)-acetamide 3-{2-[N-methyl-N-[4-cyano-4-dodecyl-4-(3,4-dimethoxyphenyl)-butyl]-aminoethyl]}-phenoxy-N-(2,4-dimethyl-3-nitrooxypentyl-2)-acetamide 3-{2-[N-methyl-N-[4-cyano-4-dodecyl-4-(3,4-dimethoxyphenyl)-butyl]-aminoethyl]}-phenoxy-N-(2,4,4-trimethyl-3-nitrooxypentyl-2)-acetamide 3-{3-[N-methyl-N-[4-cyano-4-dodecyl-4-(3,4-dimethoxyphenyl)-butyl]-aminoethyl]}-phenoxy-N-(2,2-dimethyl-3-nitrooxypropyl-1)-acetamide 4-{2-[N-methyl-N-[4-cyano-4-dodecyl-4-(3,4-dimethoxyphenyl)-butyl]aminoethyl]}-phenoxy-N-(nitrooxyethyl)-acetamide 4-{2-[N-methyl-N-[4-cyano-4-dodecyl-4-(3,4-dimethoxyphenyl)-butyl]-aminoethyl]}-phenoxy-N-(2-nitrooxypropyl)-acetamide 4-{2-[N-methyl-N-[4-cyano-4-dodecyl-4-(3,4-dimethoxyphenyl)-butyl]-aminoethyl]}-phenoxy-N-(3-nitrooxybutyl-2)-acetamide 4-{2-[N-methyl-N-[4-cyano-4-dodecyl-4-(3,4-dimethoxyphenyl)-butyl]-aminoethyl]}-phenoxy-N-(3-nitrooxypropyl-1)-acetamide 4-{2-[N-methyl-N-[4-cyano-4-dodecyl-4-(3,4-dimethoxyphenyl)-butyl]-aminoethyl]}-phenoxyacetic acid 4-(nitrooxymethyl)-piperidylamide 4-{2-[N-methyl-N-[4-cyano-4-dodecyl-4-(3,4-dimethoxyphenyl)-butyl]-aminoethyl]}-phenoxyacetic acid 4-(α-nitrooxyethyl)-piperidylamide 4-{2-[N-methyl-N-[4-cyano-4-dodecyl-4-(3,4-dimethoxyphenyl)-butyl]-aminoethyl]}-phenoxy-N-(4-methyl-3-nitrooxypentyl-2)-acetamide 4-{2-[N-methyl-N-[4-cyano-4-dodecyl-4-(3,4-dimethoxyphenyl)-butyl]-aminoethyl]}-phenoxy-N-(4,4-dimethyl-3-nitrooxypentyl-2)-acetamide 4-{2-[N-methyl-N-[4-cyano-4-dodecyl-4-(3,4-dimethoxyphenyl)-butyl]-aminoethyl]}-phenoxy-N-(2,4-dimethyl-3-nitrooxypentyl-2)-acetamide 4-{2-[N-methyl-N-[4-cyano-4-dodecyl-4-(3,4-dimethoxyphenyl)-butyl]-aminoethyl]}-phenoxy-N-(2,4,4-trimethyl-3-nitrooxypentyl-2)-acetamide 4-{2-[N-methyl-N-[4-cyano-4-dodecyl-4-(3,4-dimethoxyphenyl)-butyl]-aminoethyl]}-phenoxy-N-(2,2-dimethyl-3-nitrooxypropyl-1)-acetamide 4-{2-[N-methyl-N-[4-cyano-4-hexyl-4-(3,4,5-trimethoxyphenyl)-butyl]-aminoethyl]}-phenoxy-N-(nitrooxyethyl)-acetamide 4-{2-[N-methyl-N-[4-cyano-4-hexyl-4-(3,4,5-trimethoxyphenyl)-butyl]-aminoethyl]}-phenoxy-N-(2-nitrooxypropyl)-acetamide 4-{2-[N-methyl-N-[4-cyano-4-hexyl-4-(3,4,5-trimethoxyphenyl)-butyl]-aminoethyl]}-phenoxy-N-(3-nitrooxybutyl-2)-acetamide 4-{2-[N-methyl-N-[4-cyano-4-hexyl-4-(3,4,5-trimethoxyphenyl)-butyl]-aminoethyl]}-phenoxy-N-(3-nitrooxypropyl-1)-acetamide 4-{2-[N-methyl-N-[4-cyano-4-hexyl-4-(3,4,5-trimethoxyphenyl)-butyl]-aminoethyl]}-phenoxyacetic acid 4-(nitrooxymethyl)-piperidylamide 4-{2-[N-methyl-N-[4-cyano-4-hexyl-4-(3,4,5-trimethoxyphenyl)-butyl]-aminoethyl]}-phenoxyacetic acid 4-(α-nitrooxyethyl)-piperidylamide 4-{2-[N-methyl-N-[4-cyano-4-hexyl-4-(3,4,5-trimethoxyphenyl)-butyl]-aminoethyl]}-phenoxy-N-(4-methyl-3-nitrooxypentyl-2)-acetamide 4-{2-[N-methyl-N-[4-cyano-4-hexyl-4-(3,4,5-trimethoxyphenyl)-butyl]-aminoethyl]}-phenoxy-N-(4,4-dimethyl-3-nitrooxypentyl-2)-acetamide 4-{2-[N-methyl-N-[4-cyano-4-hexyl-4-(3,4,5-trimethoxyphenyl)-butyl]aminoethyl]}-phenoxy-N-(2,4-dimethyl-3-nitrooxypentyl-2)-acetamide 4-{2-[M-methyl-N-[4-cyano-4-hexyl-4-(3,4,5-trimethoxyphenyl)-butyl]-aminoethyl]}-phenoxy-N-(2,4,4-trimethyl-3-nitrooxypentyl-2)-acetamide 4-{2-[N-methyl-N-[4-cyano-4-hexyl-4-(3,4,5-trimethoxyphenyl)-butyl]-aminoethyl]}-phenoxy-N-(2,2-dimethyl-3-nitrooxypropyl-1)-acetamide 4-{2-[N-methyl-N-[4-cyano-4-dodecyl-4-(3,4-dimethoxyphenyl)-butyl]-aminoethyl]}-phenoxy-N-(nitrooxyethyl)-acetamide 4-{2-[N-methyl-N-[4-cyano-4-dodecyl-4-(3,4-dimethoxyphenyl)-butyl]-aminoethyl]}-phenoxy-N-(2-nitrooxypropyl)-acetamide 3-{2-[N-methyl-N-[4-cyano-4-hexyl-4-(3,4-dimethoxyphenyl)-butyl]-aminoethyl]}-phenoxy-N-(3-nitrooxybutyl-2)-acetamide 3-{2-[N-methyl-N-[4-cyano-4-hexyl-4-(3,4-dimethoxyphenyl)-butyl]-aminoethyl]}-phenoxy-N-(3-nitrooxypropyl-1)-acetamide 3-{2-[N-methyl-N-[4-cyano-4-hexyl-4-(3,4-dimethoxyphenyl)-butyl]-aminoethyl]}-phenoxyacetic acid 4-(nitrooxymethyl)-piperidylamide 3-{2-[N-methyl-N-[4-cyano-4-hexyl-4-(3,4-dimethoxyphenyl)-butyl]-aminoethyl]}-phenoxyacetic acid 4-(α-nitrooxyethyl)-piperidylamide 3-{2-[N-methyl-N-[4-cyano-4-hexyl-4-(3,4-dimethoxyphenyl)-butyl]-aminoethyl]}-phenoxy-N-(4-methyl-3-nitrooxypentyl-2)-acetamide 3-{2-[N-methyl-N-[4-cyano-4-dodecyl-4-(3,4-dimethoxyphenyl)-butyl]-aminoethyl]}-phenoxy-N-(4,4-dimethyl-3-nitrooxypentyl-2)-acetamide 3-{2-[N-methyl-N-[4-cyano-4-dodecyl-4-(3,4-dimethoxyphenyl)-butyl]-aminoethyl]}-phenoxy-N-(2,4-dimethyl-3-nitrooxypentyl-2)-acetamide 3-{2-[N-methyl-N-[4-cyano-4-dodecyl-4-(3,4-dimethoxyphenyl)-butyl]-aminoethyl]}-phenoxy-N-(2,4,4-trimethyl-3-nitrooxypentyl-2)-acetamide 3-{2-[N-methyl-N-[4-cyano-4-dodecyl-4-(3,4-dimethoxyphenyl)-butyl]-aminoethyl]}-phenoxy-N-(2,2-dimethyl-3-nitrooxypropyl-1)-acetamide 4-{1-cyano-1-hexyl-4-[N-methyl-N-[2-(3-methoxyphenyl)-ethyl]-aminobutyl]}-phenoxy-N-(nitrooxyethyl)-acetamide 4-{1-cyano-1-hexyl-4-[N-methyl-N-[2-(3-methoxyphenyl)-ethyl]-aminobutyl]}-phenoxy-N-(2-nitrooxypropyl)-acetamide 4-{1-cyano-1-hexyl-4-[N-methyl-N-[2-(3-methoxyphenyl)-ethyl]-aminobutyl]}-phenoxy-N-(3-nitrooxypropyl)-acetamide 4-{1-cyano-1-hexyl-4-[N-methyl-N-[2-(3-methoxyphenyl)-ethyl]-aminobutyl]}-phenoxyacetic acid 4-(nitrooxymethyl)-piperidylamide 4-{1-cyano-1-hexyl-4-[N-methyl-N-[2-(3-methoxyphenyl)-ethyl]-aminobutyl]}-phenoxyacetic acid 4-(α-nitrooxyethyl)-piperidylamide 4-{1-cyano-1-hexyl-4-[N-methyl-N-[2-(3-methoxyphenyl)-ethyl]-aminobutyl]}-phenoxy-N-(4-methyl-3-nitrooxypentyl-2)-acetamide 4-{1-cyano-1-hexyl-4-[N-methyl-N-[2-(3-methoxyphenyl)-ethyl]-aminobutyl]}-phenoxy-N-(4,4-dimethyl-3-nitrooxypentyl-2)-acetamide 4-{1-cyano-1-hexyl-4-[N-methyl-N-[2-(3-methoxyphenyl)-ethyl]-aminobutyl]}-phenoxy-N-(2,4-dimethyl-3-nitrooxypentyl-2)-acetamide 4-{1-cyano-1-hexyl-4-[N-methyl-N-[2-(3-methoxyphenyl)-ethyl]-aminobutyl]}-phenoxy-N-(2,4,4-trimethyl-3-nitrooxypentyl-2)-acetamide 4-{1-cyano-1-hexyl-4-[N-methyl-N-[2-(3-methoxyphenyl)-ethyl]-aminobutyl]}-phenoxy-N-(2,2-dimethyl-3-nitrooxypropyl-1)-acetamide 4-{1-cyano-1-hexyl-4-[N-methyl-N-[2-(4-methoxyphenyl)-ethyl]-aminobutyl]}-phenoxy-N-(nitrooxyethyl)-acetamide 4-{1-cyano-1-hexyl-4-[N-methyl-N-[2-(4-methoxyphenyl)-ethyl]-aminobutyl]}-phenoxy-N-(2-nitrooxypropyl)-acetamide 4-{1-cyano-1-hexyl-4-[N-methyl-N-[2-(4-methoxyphenyl)-ethyl]-aminobutyl]}-phenoxy-N-(3-nitrooxypropyl-1)-acetamide 4-{1-cyano-1-hexyl-4-[N-methyl-N-[2-(4-methoxyphenyl)-ethyl]-aminobutyl]}-phenoxyacetic acid 4-(nitrooxymethyl)-piperidylamide 4-{1-cyano-1-hexyl-4-[N-methyl-N-[2-(4-methoxyphenyl)-ethyl]-aminobutyl]}-phenoxyacetic acid 4-(α-nitrooxyethyl)-piperidylamide 4-{1-cyano-1-hexyl-4-[N-methyl-N-[2-(4-methoxyphenyl)-ethyl]-aminobutyl]}-phenoxy-N-(4-methyl-3-nitrooxypentyl-2-)-acetamide 4-{1-cyano-1-hexyl-4-[N-methyl-N-[2-(4-methoxyphenyl)-ethyl]-aminobutyl]}-phenoxy-N-(4,4-dimethyl-3-nitrooxypentyl-2)-acetamide 4-{1-cyano-1-hexyl-4-[N-methyl-N-[2-(4-methoxyphenyl)-ethyl]-aminobutyl]}-phenoxy-N-(2,4-dimethyl-3-nitrooxypentyl-2)-acetamide 4-{1-cyano-1-hexyl-4-[N-methyl-N-[2-(4-methoxyphenyl)-ethyl]-aminobutyl]}-phenoxy-N-(2,4,4-trimethyl-3-nitrooxypentyl-2)-acetamide 4-{1-cyano-1-hexyl-4-[N-methyl-N-[2-(4-methoxyphenyl)-ethyl]-aminobutyl]}-phenoxy-N-(2,2-dimethyl-3-nitrooxypropyl-1)-acetamide 3-{1-cyano-1-hexyl-4-[N-methyl-N-[2-(3-methoxyphenyl)-ethyl]-aminobutyl]}-phenoxy-N-(nitrooxyethyl)-acetamide 3-{1-cyano-1-hexyl-4-[N-methyl-N-[2-(3-methoxyphenyl)-ethyl]-aminobutyl]}-phenoxy-N-(2-nitrooxypropyl)-acetamide 3-{1-cyano-1-hexyl-4-[N-methyl-N-[2-(3-methoxyphenyl)-ethyl]-aminobutyl]}-phenoxy-N-(3-nitrooxypropyl-1)-acetamide 3-{1-cyano-1-hexyl-4-[N-methyl-N-[2-(3-methoxyphenyl)-ethyl]-aminobutyl]}-phenoxyacetic acid 4-(nitrooxymethyl)-piperidylamide 3-{1-cyano-1-hexyl-4-[N-methyl-N-[2-(3-methoxyphenyl)-ethyl]-aminobutyl]}-phenoxyacetic acid 4-(α-nitrooxyethyl)-piperidylamide 3-{1-cyano-1-hexyl-4-[N-methyl-N-[2-(3-methoxyphenyl)-ethyl]-aminobutyl]}-phenoxy-N-(4-methyl-3-nitrooxypentyl-2)-acetamide 3-{1-cyano-1-hexyl-4-[N-methyl-N-[2-(3-methoxyphenyl)-ethyl]-aminobutyl]}-phenoxy-N-(4,4-dimethyl-3-nitrooxypentyl-2)-acetamide 3-{1-cyano-1-hexyl-4-[N-methyl-N-[2-(3-methoxyphenyl)-ethyl]-aminobutyl]}-phenoxy-N-(2,4-dimethyl-3-nitrooxypentyl-2)-acetamide 3-{1-cyano-1-hexyl-4-[N-methyl-N-[2-(3-methoxyphenyl)-ethyl]-aminobutyl]}-phenoxy-N-(2,4,4-trimethyl-3-nitrooxypentyl-2)-acetamide 3-{1-cyano-1-hexyl-4-[N-methyl-N-[2-(3-methoxphenyl)-ethyl]-aminobutyl]}-phenoxy-N-(2,2-dimethyl-3-nitrooxypropyl-1)-acetamide 3-{1-cyano-1-hexyl-4-[N-methyl-N-[2-(4-methoxyphenyl)-ethyl]-aminobutyl]}-phenoxy-N-(nitrooxyethyl)-acetamide 3-{1-cyano-1-hexyl-4-[N-methyl-N-[2(4-methoxyphenyl)-ethyl]-aminobutyl]}-phenoxy-N-(2-nitrooxypropyl)-acetamide 3-{1-cyano-1-hexyl-4-[N-methyl-N-[2-(4-methoxyphenyl)-ethyl]-aminobutyl]}-phenoxy-N-(3-nitrooxypropyl-1)-acetamide 3-{1-cyano-1-hexyl-4-[N-methyl-N-[2-(4-methoxyphenyl)-ethyl]-aminobutyl]}-phenoxyacetic acid 4-(nitrooxymethyl)-piperidylamide 3-{1-cyano-1-hexyl-4-[N-methyl-N-[2-(4-methoxyphenyl)-ethyl]-aminobutyl]}-phenoxyacetic acid 4-(α-nitrooxyethyl)-piperidylamide 3-{1-cyano-1-hexyl-4-[N-methyl-N-[2-(4-methoxyphenyl)-ethyl]-aminobutyl]}-phenoxy-N-(4-methyl-3-nitrooxypentyl-2)-acetamide 3-{1-cyano-1-hexyl-4-[N-methyl-N-[2-(4-methoxyphenyl)-ethyl]-aminobutyl]}-phenoxy-N-(4,4-dimethyl-3-nitrooxypentyl-2)-acetamide 3-{1-cyano-1-hexyl-4-[N-methyl-N-[2-(4-methoxyphenyl)-ethyl]-aminobutyl]}-phenoxy-N-(2,4-dimethyl-3-nitrooxypentyl-2)-acetamide 3-{1-cyano-1-hexyl-4-[N-methyl-N-[2-(4-methoxyphenyl)-ethyl]-aminobutyl]}-phenoxy-N-(2,4,4-trimethyl-3-nitrooxypentyl-2)-acetamide 3-{1-cyano-1-hexyl-4-[N-methyl-N-[2-(4-methoxyphenyl)-ethyl]-aminobutyl]}-phenoxy-N-(2,2-dimethyl-3-nitrooxypropyl-1)-acetamide α-isopropyl-α-[(N-methyl-N-homoveratryl)-amino-γ-propyl]-3-methoxy-4-(2-nitrooxyethoxy)-phenylacetonitrile α-isopropyl-α-[(N-methyl-N-homoveratryl)-amino-γ-propyl]-3-methoxy-4-(2-nitrooxypropoxy)-phenylacetonitrile.

α-isopropyl-α[(N-methyl-N-homoveratryl)-amino-γ-propyl]-3-methoxy-4-(3-amino-2-nitrooxypropoxy)-phenylacetonitrile α-isopropyl-α-[(N-methyl-N-homoveratryl)-amino-γ-propyl]-3-methoxy-4-(3-dimethylamino-2-nitrooxypropoxy)-phenylacetonitrile α-isopropyl-α-[(N-methyl-N-homoveratryl)-amino-γ-propyl]-3-(2-nitrooxyethoxy)-4-methoxyphenylacetonitrile.

α-isopropyl-α-[(N-methyl-N-homoveratryl)-amino-γ-propyl]-3-(2-nitrooxypropoxy)-4-methoxyphenylacetonitrile α-isopropyl-α-[(N-methyl-N-homoveratryl)-amino-γ-propyl]-3-(3-amino-2-nitrooxypropoxy)-4-methoxyphenylacetonitrile α-isopropyl-α-[(N-methyl-N-homoveratryl)-amino-γ-propyl]-3-(3-dimethylamino-2-nitrooxypropoxy)-4-methoxyphenylacetonitrile α-isopropyl-α-{[N-methyl-N-[2-(3-methoxy-4-(2-nitrooxyethoxy)-phenyl)-ethyl]]-amino-γ-propyl}-3,4-dimethoxyphenylacetonitrile α-isopropyl-α-{[N-methyl-N-[2-(3-methoxy-4-(2-nitrooxypropoxy)-phenyl)-ethyl]]-amino-γ-propyl}-3,4-dimethoxyphenylacetonitrile α-isopropyl-α-{[N-methyl-N-[2-(3-methoxy-4-(3-amino-2-nitrooxypropoxy)-phenyl)-ethyl]]-amino-γ-propyl}-3,4-dimethoxyphenylacetonitrile α-isopropyl-α-{[N-methyl-N-[2-(3-methoxy-4-(3-dimethylamino-2-nitrooxypropoxy)-phenyl)-ethyl]]-amino-γ-propyl}-3,4-dimethoxyphenylacetonitrile α-isopropyl-α-{[N-methyl-N-[2-(4-methoxy-3-(2-nitrooxyethoxy)-phenyl)-ethyl]]-amino-γ-propyl}-3,4-dimethoxyphenylacetonitrile α-isopropyl-α-{[N-methyl-N-[2-(4-methoxy-3-(2-nitrooxypropoxy)-phenyl)-ethyl]]-amino-γ-propyl}-3,4-dimethoxyphenylacetonitrile α-isopropyl-α-{[N-methyl-N-[2-(4-methoxy-3-(3-amino-2-nitrooxypropoxy)-phenyl)-ethyl]]-amino-γ-propyl}-3,4-dimethoxyphenylacetonitrile α-ispropyl-α-{[N-methyl-N-[2-(4-methoxy-3-(3-dimethylamino-2-nitrooxypropoxy)-phenyl)-ethyl]]-amino-γ-propyl}-3,4-dimethoxyphenylacetonitrile 2-(nitrooxy)-N-{2-methoxy-4-}1-cyano-1-(methylethyl)-4-[N-methyl-N-[2-(3,4-dimethoxyphenyl)-ethyl]-aminobutyl]}-phenoxyethyl-2)-propionacid amide 4-(nitrooxy)-N-{2-methoxy-4-{1-cyano-1-(methylethyl)-4-[N-methyl-N-[2-(3,4-dimethoxyphenyl)-ethyl]-aminobutyl]}-phenoxy-ethyl-2}-butyric acid amide 3-(nitrooxy)-2,2-dimethyl-N-{2-methoxy-4-{1-cyano-1-(methylethyl)-4-[N-methyl-N-[2-(3,4-dimethoxyphenyl)-ethyl]-aminobutyl]}-phenoxyethyl-2}-butyric acid amide 2-(nitrooxy)-N-{2-methoxy-4-{1-cyano-1-(methylethyl)-4-[N-methyl-N-[2-(3,4-dimethoxyphenyl)-ethyl]-aminobutyl]}-phenoxyethyl-2}-cyclohexane carboxylic acid amide 4-(nitrooxy)-N-{2-methoxy-4-{1-cyano-1-(methylethyl)-4-[N-methyl-N-[2-(3,4-dimethoxyphenyl)-ethyl]-aminobutyl]}-phenoxyethyl-2}-cyclohexane carboxylic acid amide 2-(nitrooxy)-N-{2-methoxy-4-{2-{N-methyl-N-[4-cyano-4-(methylethyl)-4-(3,4-dimethoxyphenyl)-butyl]-aminoethyl}}-phenoxyethyl-2}-propionic acid amide 4-(nitrooxy)-N-{2-methoxy-4-{2-{N-methyl-N-[4-cyano-4-(methylethyl)-4-(3,4-dimethoxyphenyl)-butyl]-aminoethyl}}-phenoxyethyl-2}-butyric acid amide 3-(nitrooxy)-2,2-dimethyl-N-{2-methoxy-4-{2-{N-methyl-N-[4-cyano-4-(methylethyl)-4-(3,4-dimethoxyphenyl)-butyl]-aminoethyl}}-phenoxyethyl-2}-butyric acid amide 2-(nitrooxy)-N-{2-methoxy-4-{2-{N-methyl-N-[4-cyano-4-(methylethyl)-4-(3,4-dimethoxyphenyl)-butyl]-aminoethyl}}-phenoxyethyl-2}-cyclohexane carboxylic acid amide 4-(nitrooxy)-N-{2-methoxy-4-{2-{N-methyl-N-[4-cyano-4-(methylethyl)-4-(3,4-dimethoxyphenyl)-butyl]-aminoethyl}}-phenoxyethyl-2}-cyclohexane carboxylic acid amide.

Also prepared are analogous compounds which, instead of the nitrooxy group, have a hydroxyl group, as starting materials, as well as possibly as pharmacologically active compounds.

In the following Tables, there are set out further compounds which are useful according to the present invention:

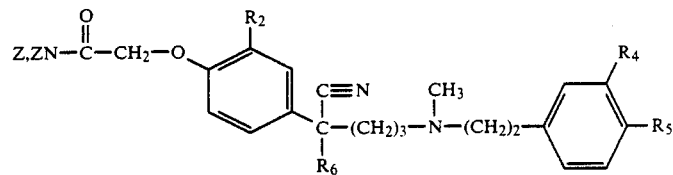

| —NZ,Z | R$_2$ | R$_6$ | R$_4$ | R$_5$ |
|---|---|---|---|---|
| pyrrolidine-CH$_2$—ONO$_2$ | —OCH$_3$ | —CH(CH$_3$)$_2$ | —OCH$_3$ | —OCH$_3$ |
| pyrrolidine-CH$_2$CH$_2$ONO$_2$ | —OCH$_3$ | —CH(CH$_3$)$_2$ | —OCH$_3$ | —OCH$_3$ |
| piperidine-CH$_2$CH$_2$ONO$_2$ | —OCH$_3$ | —CH(CH$_3$)$_2$ | —OCH$_3$ | —OCH$_3$ |
| 4-(CH$_2$CH$_2$ONO$_2$)piperidine | —OCH$_3$ | —CH(CH$_3$)$_2$ | —OCH$_3$ | —OCH$_3$ |
| piperazine-N-CH$_2$CH$_2$ONO$_2$ | —OCH$_3$ | —CH(CH$_3$)$_2$ | —OCH$_3$ | —OCH$_3$ |
| piperazine-N-CO—CH(ONO$_2$)—CH$_3$ | —OCH$_3$ | —CH(CH$_3$)$_2$ | —OCH$_3$ | —OCH$_3$ |
| —N(CH$_3$)-cyclohexyl-ONO$_2$ | —OCH$_3$ | —CH(CH$_3$)$_2$ | —OCH$_3$ | —OCH$_3$ |

-continued
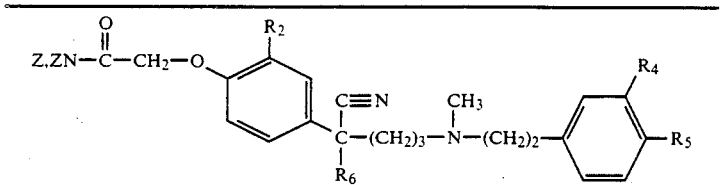
| —NZ.Z | R2 | R6 | R4 | R5 |
|---|---|---|---|---|
| 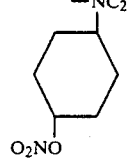 | —OCH$_3$ | —CH(CH$_3$)$_2$ | —OCH$_3$ | —OCH$_3$ |
| 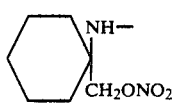 | —OCH$_3$ | —CH(CH$_3$)$_2$ | —OCH$_3$ | —OCH$_3$ |
| 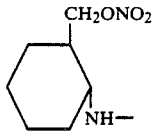 | —OCH$_3$ | —CH(CH$_3$)$_2$ | —OCH$_3$ | —OCH$_3$ |
| 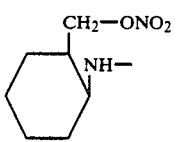 | —OCH$_3$ | —CH(CH$_3$)$_2$ | —OCH$_3$ | —OCH$_3$ |
| 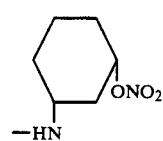 | —OCH$_3$ | —CH(CH$_3$)$_2$ | —OCH$_3$ | —OCH$_3$ |
| 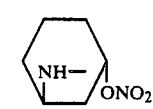 | —OCH$_3$ | —CH(CH$_3$)$_2$ | —OCH$_3$ | —OCH$_3$ |
| 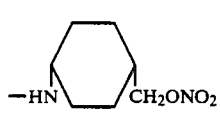 | —OCH$_3$ | —CH(CH$_3$)$_2$ | —OCH$_3$ | —OCH$_3$ |
| 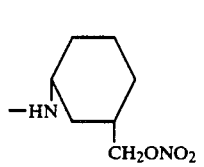 | —OCH$_3$ | —CH(CH$_3$)$_2$ | —OCH$_3$ | —OCH$_3$ |
| 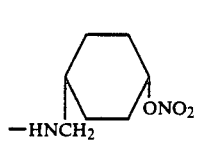 | —OCH$_3$ | —CH(CH$_3$)$_2$ | —OCH$_3$ | —OCH$_3$ |
| 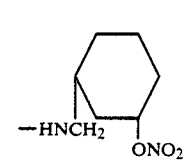 | —OCH$_3$ | —CH(CH$_3$)$_2$ | —OCH$_3$ | —OCH$_3$ |

-continued
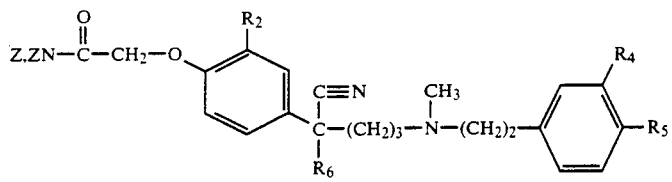
| —NZ,Z | $R_2$ | $R_6$ | $R_4$ | $R_5$ |
|---|---|---|---|---|
| 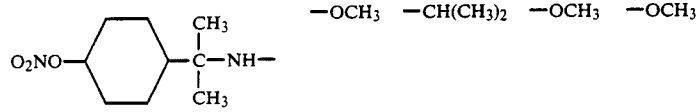 cis + trans | —$OCH_3$ | —$CH(CH_3)_2$ | —$OCH_3$ | —$OCH_3$ |
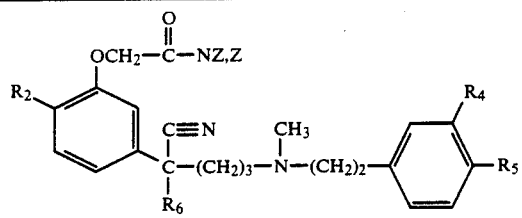
| —NZ,Z | $R_2$ | $R_6$ | $R_4$ | $R_5$ |
|---|---|---|---|---|
| 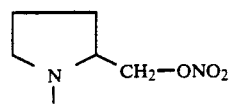 | —$OCH_3$ | —$CH(CH_3)_2$ | —$OCH_3$ | —$OCH_3$ |
| 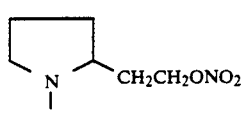 | —$OCH_3$ | —$CH(CH_3)_2$ | —$OCH_3$ | —$OCH_3$ |
| 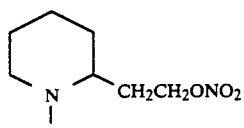 | —$OCH_3$ | —$CH(CH_3)_2$ | —$OCH_3$ | —$OCH_3$ |
| 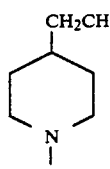 | —$OCH_3$ | —$CH(CH_3)_2$ | —$OCH_3$ | —$OCH_3$ |
| 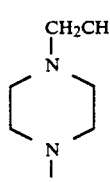 | —$OCH_3$ | —$CH(CH_3)_2$ | —$OCH_3$ | —$OCH_3$ |

-continued

Structure:
R2-substituted phenyl with OCH2-C(=O)-NZ,Z at ortho and C(CN)(R6)-(CH2)3-N(CH3)-(CH2)2-phenyl(R4,R5)

| −NZ,Z | R2 | R6 | R4 | R5 |
|---|---|---|---|---|
| piperazine N-CO-CH(ONO2)-CH3 (N-methyl piperazine with acyl group bearing ONO2) | −OCH3 | −CH(CH3)2 | −OCH3 | −OCH3 |
| 4-(ONO2)-cyclohexyl-N(CH3)− | −OCH3 | −CH(CH3)2 | −OCH3 | −OCH3 |
| 4-(O2NO)-cyclohexyl-N(C2H5)− | −OCH3 | −CH(CH3)2 | −OCH3 | −OCH3 |
| 2-(CH2ONO2)-cyclohexyl-NH− | −OCH3 | −CH(CH3)2 | −OCH3 | −OCH3 |
| 3-(CH2ONO2)-cyclohexyl-NH− | −OCH3 | −CH(CH3)2 | −OCH3 | −OCH3 |
| 2-(CH2ONO2)-cyclohexyl-NH− (isomer) | −OCH3 | −CH(CH3)2 | −OCH3 | −OCH3 |
| 3-(ONO2)-cyclohexyl-NH− | −OCH3 | −CH(CH3)2 | −OCH3 | −OCH3 |
| 3-(ONO2)-piperidin-NH− | −OCH3 | −CH(CH3)2 | −OCH3 | −OCH3 |
| 3-(CH2ONO2)-piperidin-NH− | −OCH3 | −CH(CH3)2 | −OCH3 | −OCH3 |

-continued
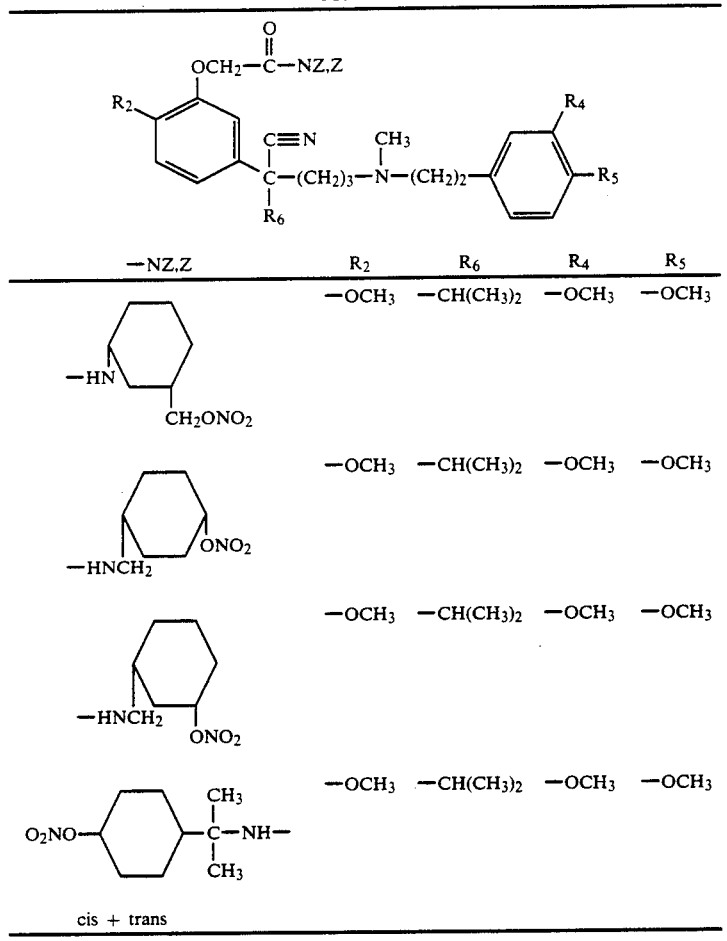
| −NZ,Z | $R_2$ | $R_6$ | $R_4$ | $R_5$ |
|---|---|---|---|---|
|  | −OCH$_3$ | −CH(CH$_3$)$_2$ | −OCH$_3$ | −OCH$_3$ |
|  | −OCH$_3$ | −CH(CH$_3$)$_2$ | −OCH$_3$ | −OCH$_3$ |
|  | −OCH$_3$ | −CH(CH$_3$)$_2$ | −OCH$_3$ | −OCH$_3$ |
|  | −OCH$_3$ | −CH(CH$_3$)$_2$ | −OCH$_3$ | −OCH$_3$ |
cis + trans
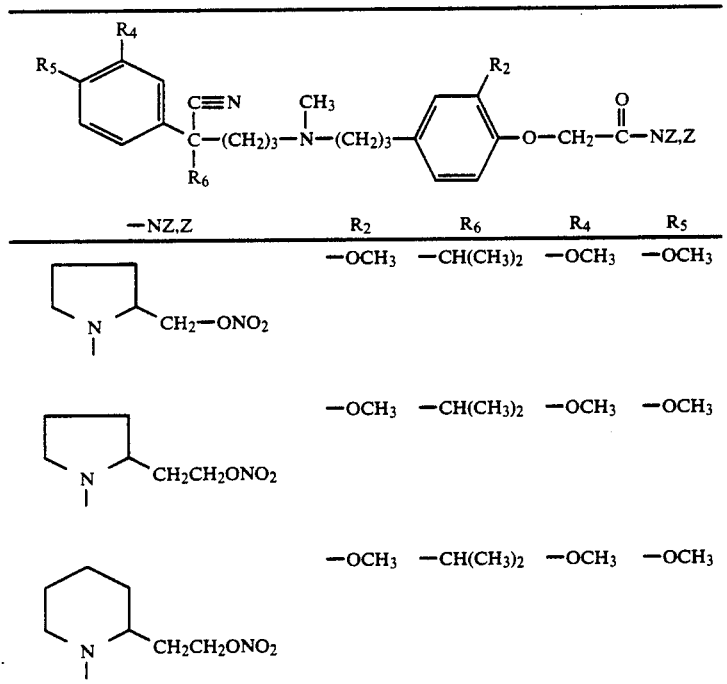
| −NZ,Z | $R_2$ | $R_6$ | $R_4$ | $R_5$ |
|---|---|---|---|---|
|  | −OCH$_3$ | −CH(CH$_3$)$_2$ | −OCH$_3$ | −OCH$_3$ |
|  | −OCH$_3$ | −CH(CH$_3$)$_2$ | −OCH$_3$ | −OCH$_3$ |
|  | −OCH$_3$ | −CH(CH$_3$)$_2$ | −OCH$_3$ | −OCH$_3$ |

-continued
| —NZ.Z | R2 | R6 | R4 | R5 |
|---|---|---|---|---|
| 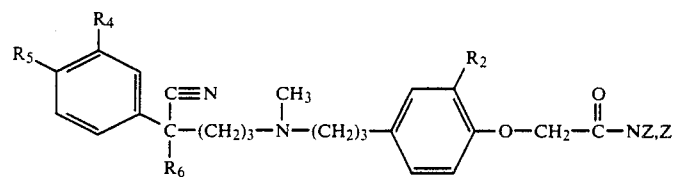 | —OCH3 | —CH(CH3)2 | —OCH3 | —OCH3 |
| 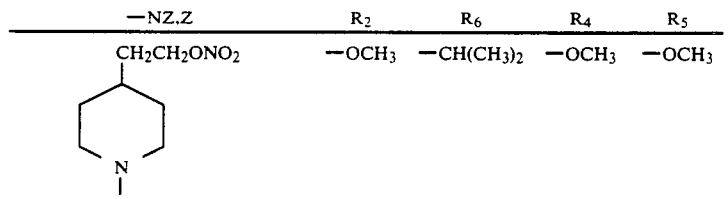 | —OCH3 | —CH(CH3)2 | —OCH3 | —OCH3 |
| 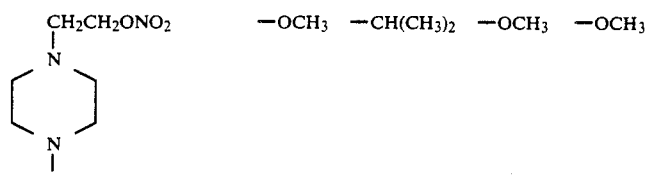 | —OCH3 | —CH(CH3)2 | —OCH3 | —OCH3 |
| 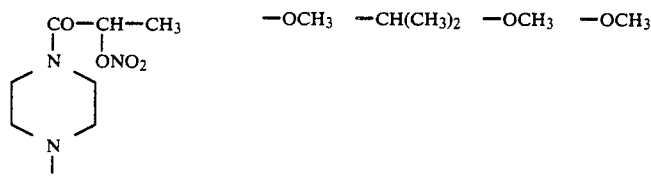 | —OCH3 | —CH(CH3)2 | —OCH3 | —OCH3 |
| 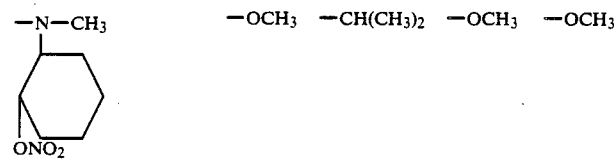 | —OCH3 | —CH(CH3)2 | —OCH3 | —OCH3 |
| 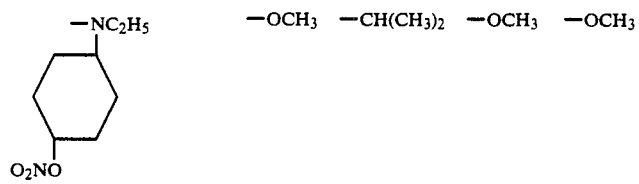 | —OCH3 | —CH(CH3)2 | —OCH3 | —OCH3 |
| 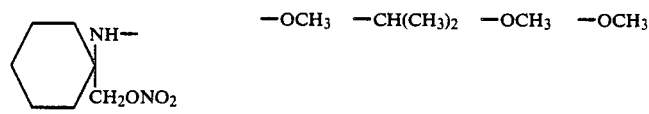 | —OCH3 | —CH(CH3)2 | —OCH3 | —OCH3 |
| 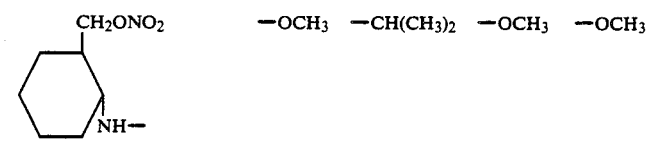 | —OCH3 | —CH(CH3)2 | —OCH3 | —OCH3 |
| 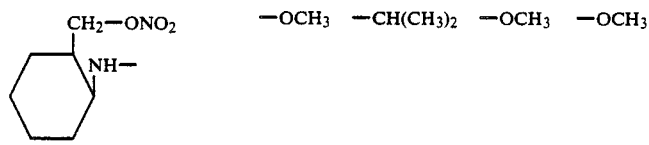 | —OCH3 | —CH(CH3)2 | —OCH3 | —OCH3 |

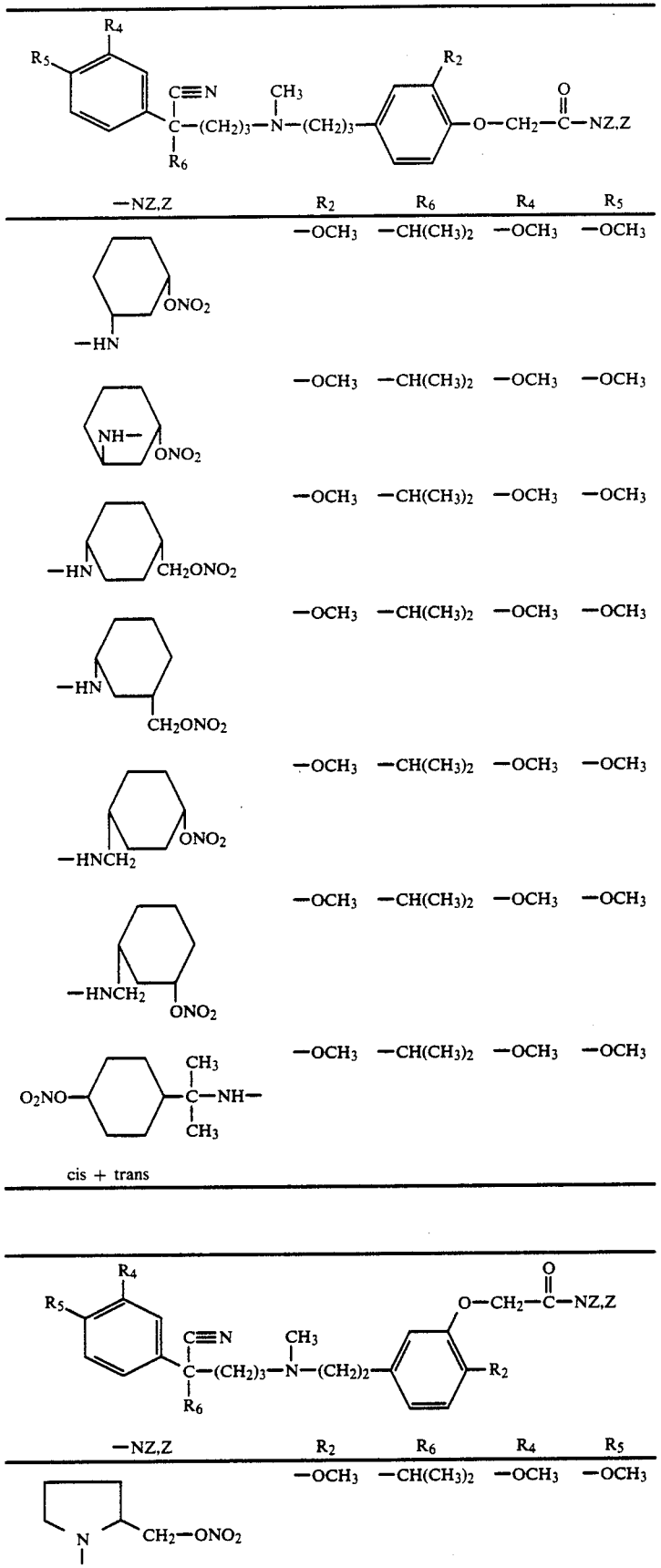

-continued
| —NZ,Z | R₂ | R₆ | R₄ | R₅ |
|---|---|---|---|---|
| 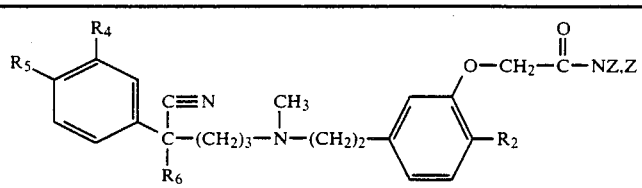 | —OCH₃ | —CH(CH₃)₂ | —OCH₃ | —OCH₃ |
| 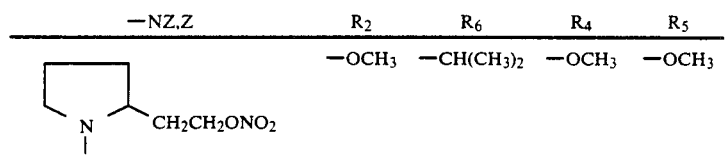 | —OCH₃ | —CH(CH₃)₂ | —OCH₃ | —OCH₃ |
| 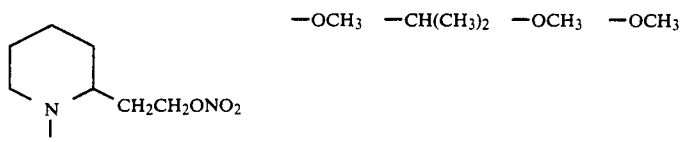 | —OCH₃ | —CH(CH₃)₂ | —OCH₃ | —OCH₃ |
| 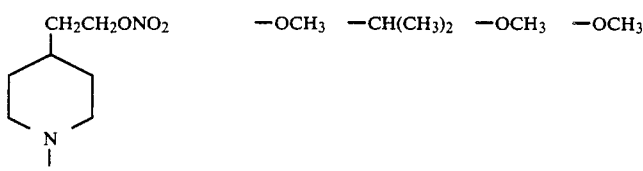 | —OCH₃ | —CH(CH₃)₂ | —OCH₃ | —OCH₃ |
| 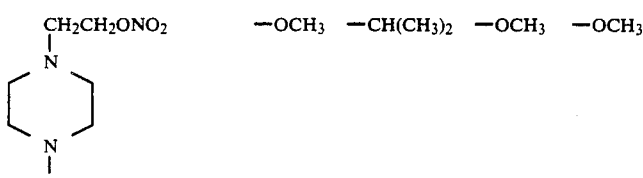 | —OCH₃ | —CH(CH₃)₂ | —OCH₃ | —OCH₃ |
| 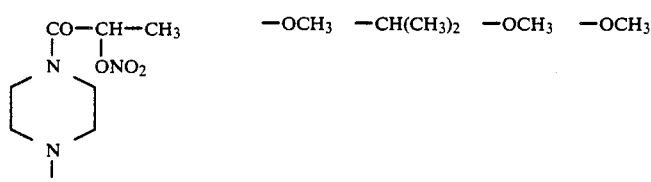 | —OCH₃ | —CH(CH₃)₂ | —OCH₃ | —OCH₃ |
| 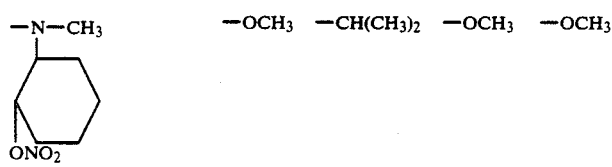 | —OCH₃ | —CH(CH₃)₂ | —OCH₃ | —OCH₃ |
| 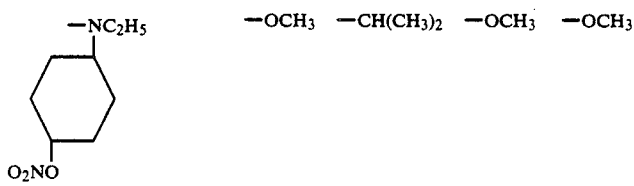 | —OCH₃ | —CH(CH₃)₂ | —OCH₃ | —OCH₃ |
| 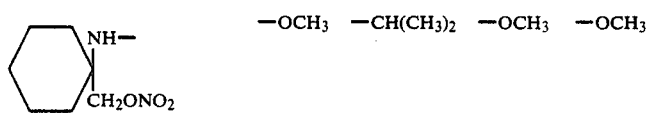 | —OCH₃ | —CH(CH₃)₂ | —OCH₃ | —OCH₃ |

-continued

[Structure: R5-R4-substituted phenyl-C(R6)(CN)-(CH2)3-N(CH3)-(CH2)2-phenyl(R2)-O-CH2-C(=O)-NZ,Z]

| —NZ,Z | R₂ | R₆ | R₄ | R₅ |
|---|---|---|---|---|
| cyclohexyl-CH₂ONO₂ with NH— | —OCH₃ | —CH(CH₃)₂ | —OCH₃ | —OCH₃ |
| cyclohexyl-CH₂—ONO₂ with NH— | —OCH₃ | —CH(CH₃)₂ | —OCH₃ | —OCH₃ |
| cyclohexyl with ONO₂, —HN | —OCH₃ | —CH(CH₃)₂ | —OCH₃ | —OCH₃ |
| piperidine NH—, ONO₂ | —OCH₃ | —CH(CH₃)₂ | —OCH₃ | —OCH₃ |
| —HN-cyclohexyl-CH₂ONO₂ | —OCH₃ | —CH(CH₃)₂ | —OCH₃ | —OCH₃ |
| —HN-piperidine-CH₂ONO₂ | —OCH₃ | —CH(CH₃)₂ | —OCH₃ | —OCH₃ |
| —HNCH₂-cyclohexyl-ONO₂ | —OCH₃ | —CH(CH₃)₂ | —OCH₃ | —OCH₃ |
| —HNCH₂-cyclohexyl-ONO₂ | —OCH₃ | —CH(CH₃)₂ | —OCH₃ | —OCH₃ |
| O₂NO-cyclohexyl-C(CH₃)₂-NH— cis + trans | —OCH₃ | —CH(CH₃)₂ | —OCH₃ | —OCH₃ |

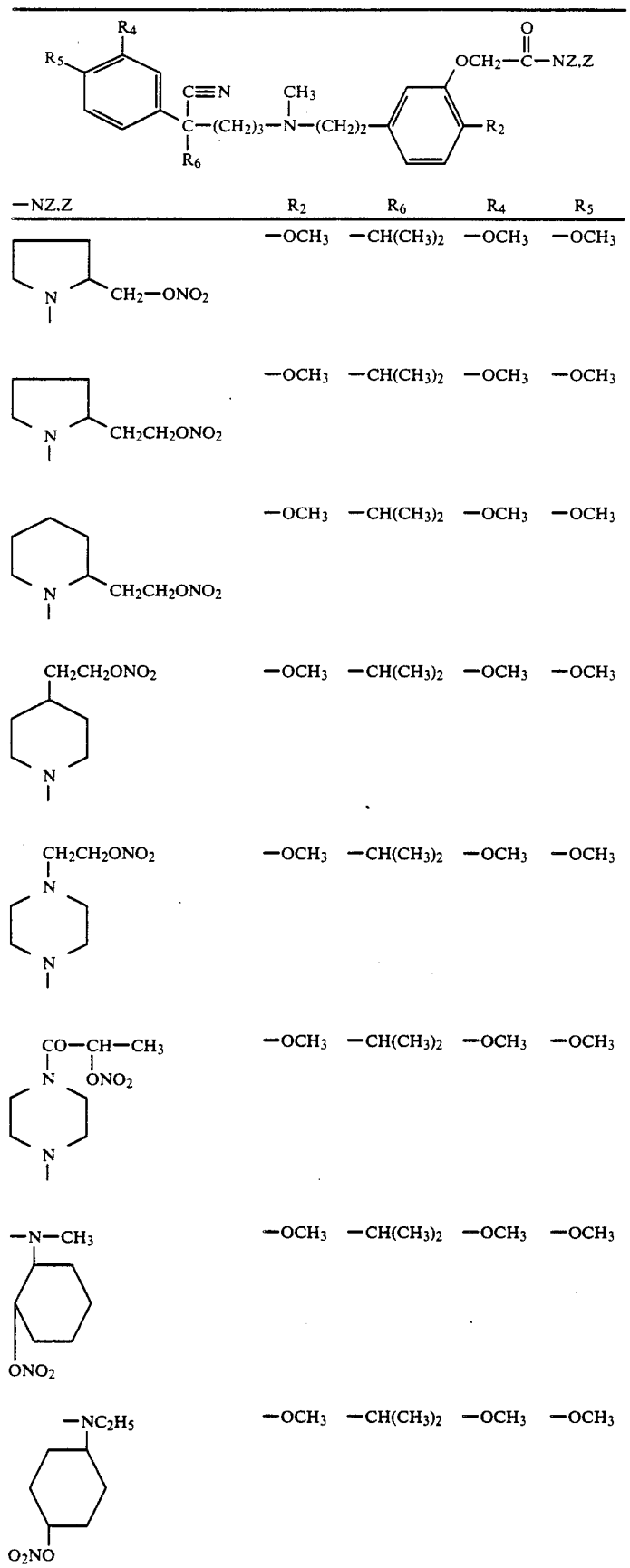

-continued
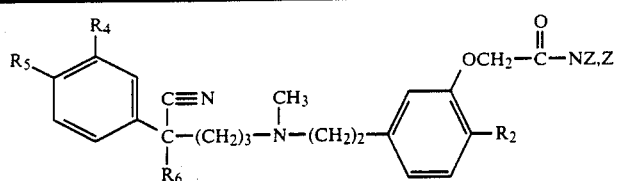
| —NZ,Z | R₂ | R₆ | R₄ | R₅ |
|---|---|---|---|---|
| 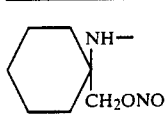 | —OCH₃ | —CH(CH₃)₂ | —OCH₃ | —OCH₃ |
| 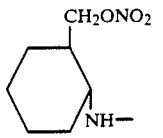 | —OCH₃ | —CH(CH₃)₂ | —OCH₃ | —OCH₃ |
| 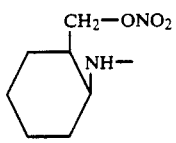 | —OCH₃ | —CH(CH₃)₂ | —OCH₃ | —OCH₃ |
| 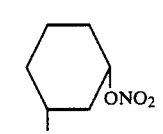 | —OCH₃ | —CH(CH₃)₂ | —OCH₃ | —OCH₃ |
| 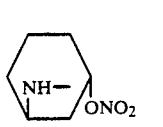 | —OCH₃ | —CH(CH₃)₂ | —OCH₃ | —OCH₃ |
| 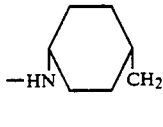 | —OCH₃ | —CH(CH₃)₂ | —OCH₃ | —OCH₃ |
| 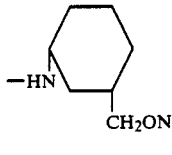 | —OCH₃ | —CH(CH₃)₂ | —OCH₃ | —OCH₃ |
| 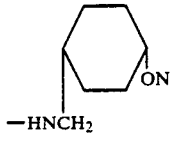 | —OCH₃ | —CH(CH₃)₂ | —OCH₃ | —OCH₃ |
| 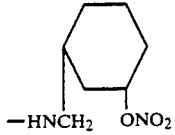 | —OCH₃ | —CH(CH₃)₂ | —OCH₃ | —OCH₃ |

-continued
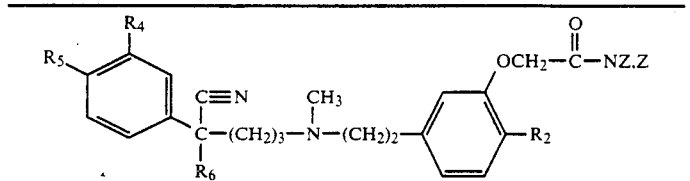
| —NZ,Z | $R_2$ | $R_6$ | $R_4$ | $R_5$ |
|---|---|---|---|---|
| 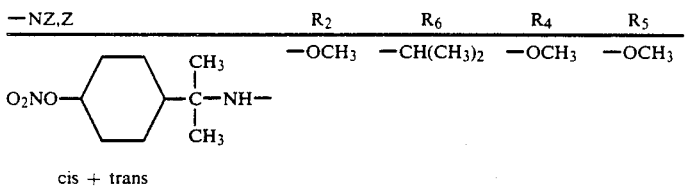 cis + trans | —OCH$_3$ | —CH(CH$_3$)$_2$ | —OCH$_3$ | —OCH$_3$ |
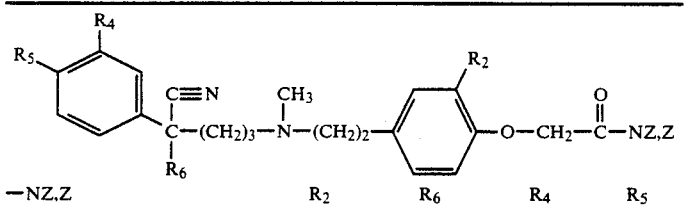
| —NZ,Z | $R_2$ | $R_6$ | $R_4$ | $R_5$ |
|---|---|---|---|---|
| 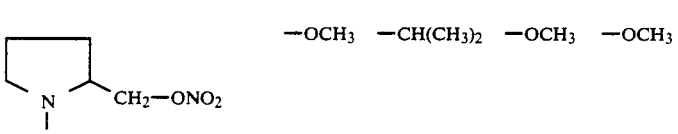 | —OCH$_3$ | —CH(CH$_3$)$_2$ | —OCH$_3$ | —OCH$_3$ |
| 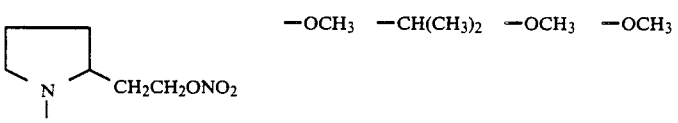 | —OCH$_3$ | —CH(CH$_3$)$_2$ | —OCH$_3$ | —OCH$_3$ |
| 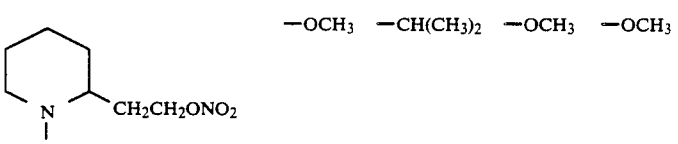 | —OCH$_3$ | —CH(CH$_3$)$_2$ | —OCH$_3$ | —OCH$_3$ |
| 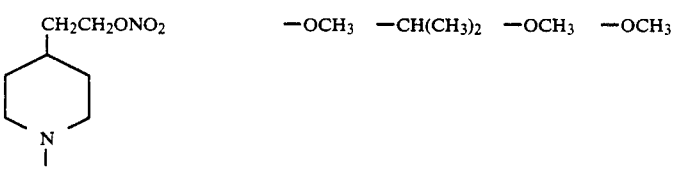 | —OCH$_3$ | —CH(CH$_3$)$_2$ | —OCH$_3$ | —OCH$_3$ |
| 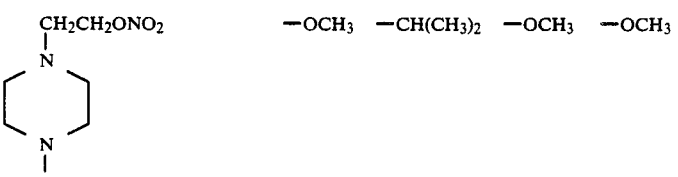 | —OCH$_3$ | —CH(CH$_3$)$_2$ | —OCH$_3$ | —OCH$_3$ |
| 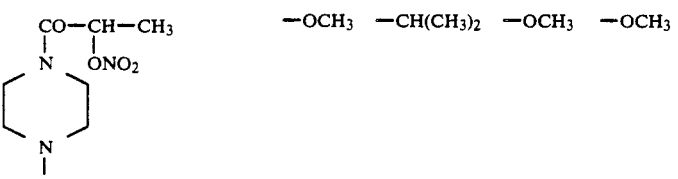 | —OCH$_3$ | —CH(CH$_3$)$_2$ | —OCH$_3$ | —OCH$_3$ |

-continued
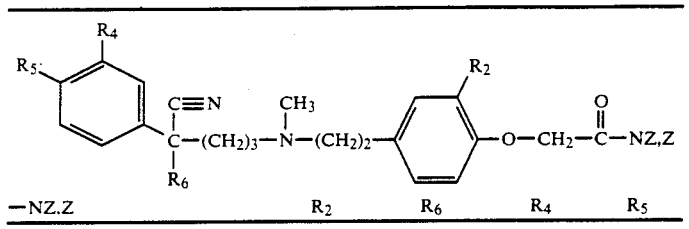
| —NZ.Z | R2 | R6 | R4 | R5 |
|---|---|---|---|---|
| 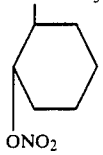 | —OCH3 | —CH(CH3)2 | —OCH3 | —OCH3 |
| 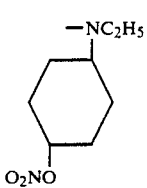 | —OCH3 | —CH(CH3)2 | —OCH3 | —OCH3 |
| 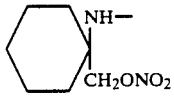 | —OCH3 | —CH(CH3)2 | —OCH3 | —OCH3 |
| 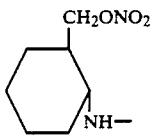 | —OCH3 | —CH(CH3)2 | —OCH3 | —OCH3 |
| 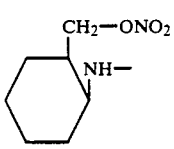 | —OCH3 | —CH(CH3)2 | —OCH3 | —OCH3 |
| 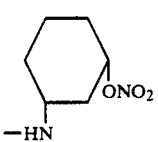 | —OCH3 | —CH(CH3)2 | —OCH3 | —OCH3 |
| 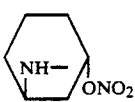 | —OCH3 | —CH(CH3)2 | —OCH3 | —OCH3 |
| 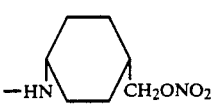 | —OCH3 | —CH(CH3)2 | —OCH3 | —OCH3 |
| 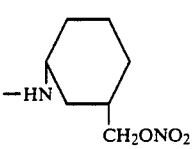 | —OCH3 | —CH(CH3)2 | —OCH3 | —OCH3 |

-continued
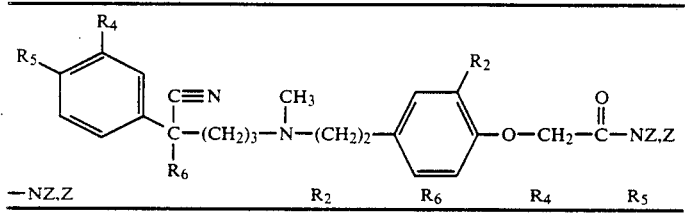
| —NZ,Z | R₂ | R₆ | R₄ | R₅ |
|---|---|---|---|---|
| 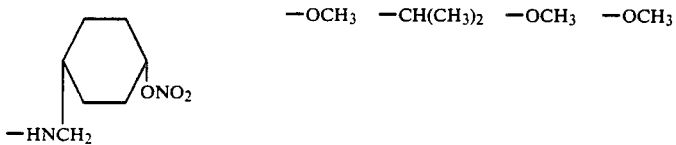 | —OCH₃ | —CH(CH₃)₂ | —OCH₃ | —OCH₃ |
| 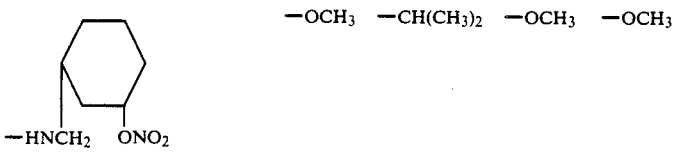 | —OCH₃ | —CH(CH₃)₂ | —OCH₃ | —OCH₃ |
| 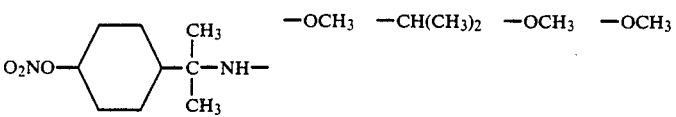 cis + trans | —OCH₃ | —CH(CH₃)₂ | —OCH₃ | —OCH₃ |
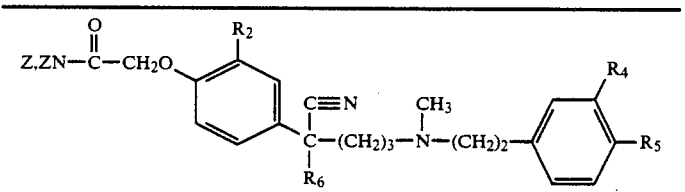
| —NZ,Z | R₂ | R₆ | R₄ | R₅ |
|---|---|---|---|---|
| 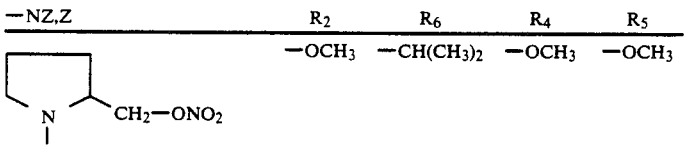 | —OCH₃ | —CH(CH₃)₂ | —OCH₃ | —OCH₃ |
| 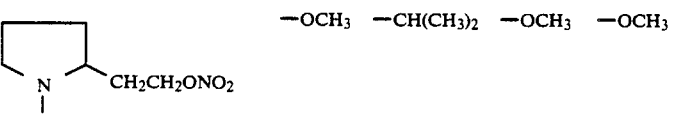 | —OCH₃ | —CH(CH₃)₂ | —OCH₃ | —OCH₃ |
| 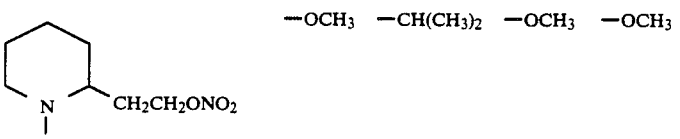 | —OCH₃ | —CH(CH₃)₂ | —OCH₃ | —OCH₃ |
| 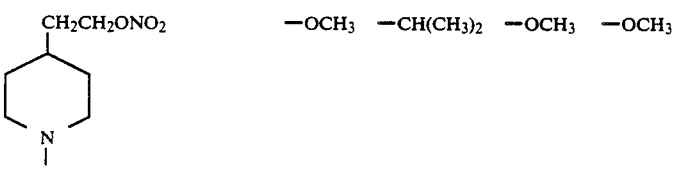 | —OCH₃ | —CH(CH₃)₂ | —OCH₃ | —OCH₃ |

-continued

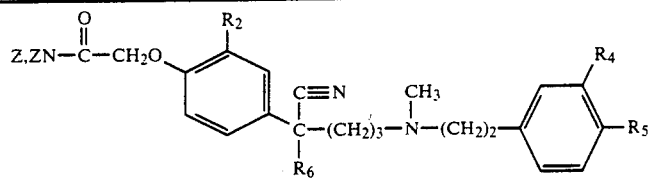

| —NZ,Z | R2 | R6 | R4 | R5 |
|---|---|---|---|---|
| piperazine with CH2CH2ONO2 on N | —OCH3 | —CH(CH3)2 | —OCH3 | —OCH3 |
| piperazine with CO—CH(ONO2)—CH3 on N | —OCH3 | —CH(CH3)2 | —OCH3 | —OCH3 |
| N(CH3)-cyclohexyl-ONO2 | —OCH3 | —CH(CH3)2 | —OCH3 | —OCH3 |
| N(C2H5)-cyclohexyl-ONO2 | —OCH3 | —CH(CH3)2 | —OCH3 | —OCH3 |
| NH-cyclohexyl-CH2ONO2 | —OCH3 | —CH(CH3)2 | —OCH3 | —OCH3 |
| cyclohexyl with CH2ONO2 and NH | —OCH3 | —CH(CH3)2 | —OCH3 | —OCH3 |
| NH-cyclohexyl-CH2—ONO2 | —OCH3 | —CH(CH3)2 | —OCH3 | —OCH3 |
| HN-cyclohexyl-ONO2 | —OCH3 | —CH(CH3)2 | —OCH3 | —OCH3 |
| piperidine NH with ONO2 | —OCH3 | —CH(CH3)2 | —OCH3 | —OCH3 |

-continued
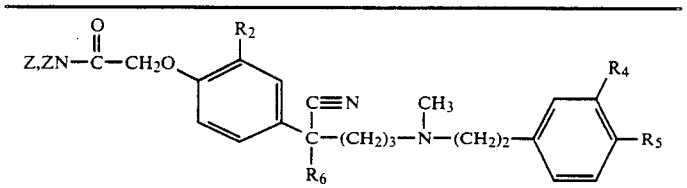
| −NZ,Z | R₂ | R₆ | R₄ | R₅ |
|---|---|---|---|---|
| 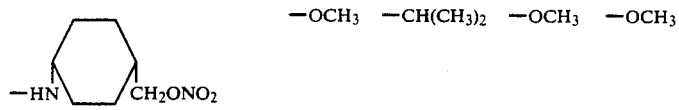 | −OCH₃ | −CH(CH₃)₂ | −OCH₃ | −OCH₃ |
| 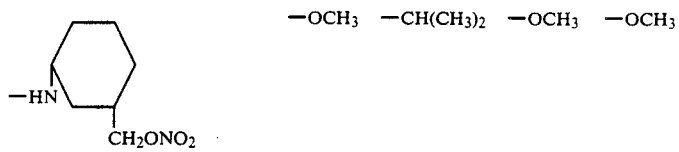 | −OCH₃ | −CH(CH₃)₂ | −OCH₃ | −OCH₃ |
| 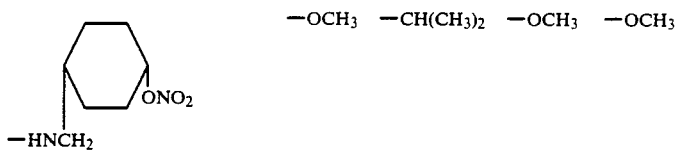 | −OCH₃ | −CH(CH₃)₂ | −OCH₃ | −OCH₃ |
| 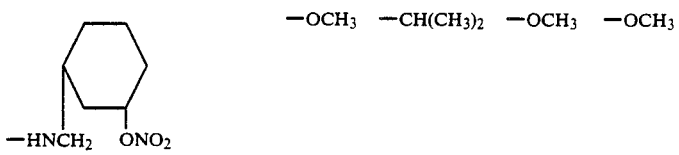 | −OCH₃ | −CH(CH₃)₂ | −OCH₃ | −OCH₃ |
| 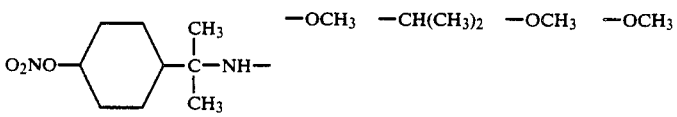  cis + trans | −OCH₃ | −CH(CH₃)₂ | −OCH₃ | −OCH₃ |
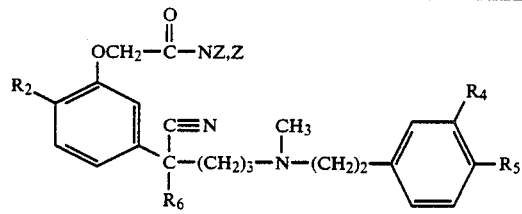
| −NZ,Z | R₂ | R₆ | R₄ | R₅ |
|---|---|---|---|---|
| 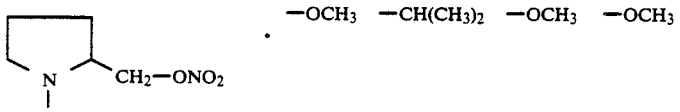 | −OCH₃ | −CH(CH₃)₂ | −OCH₃ | −OCH₃ |
| 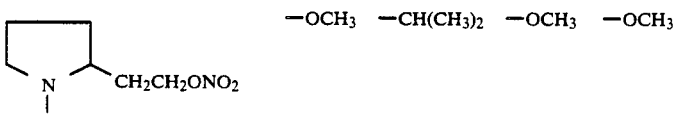 | −OCH₃ | −CH(CH₃)₂ | −OCH₃ | −OCH₃ |

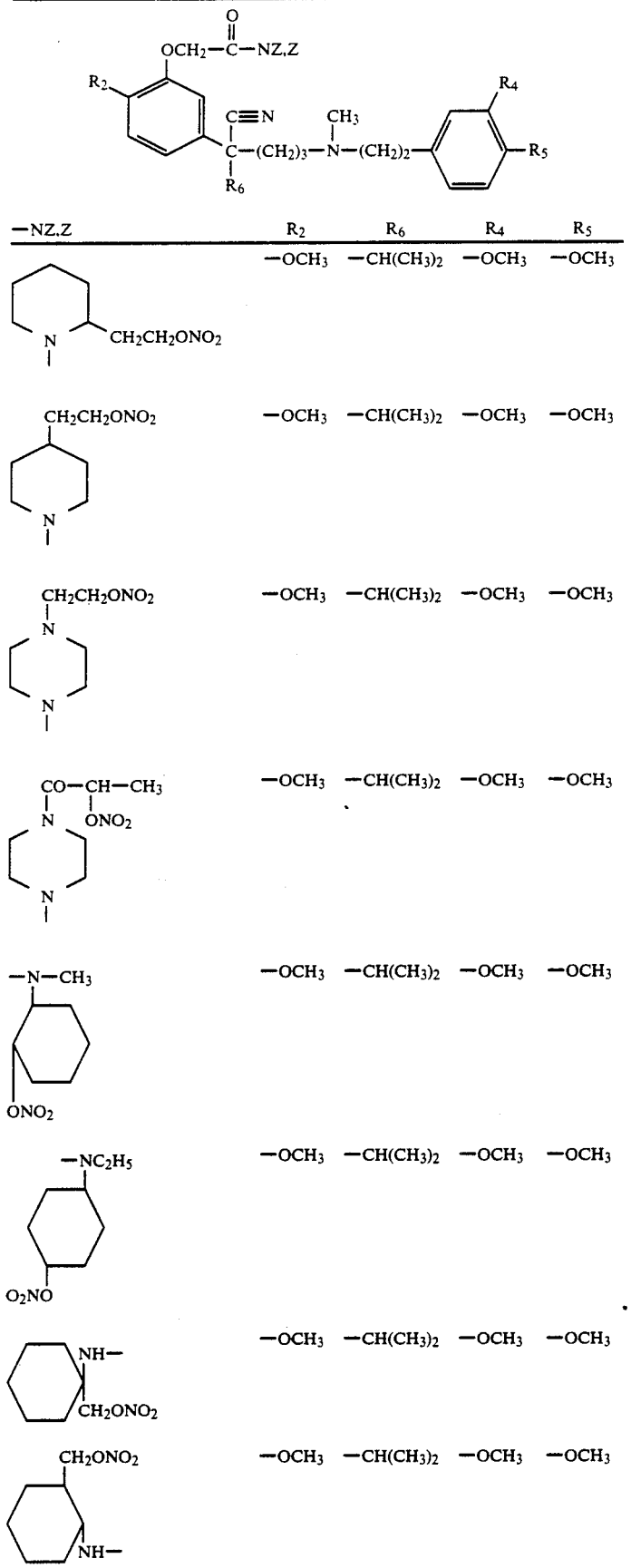

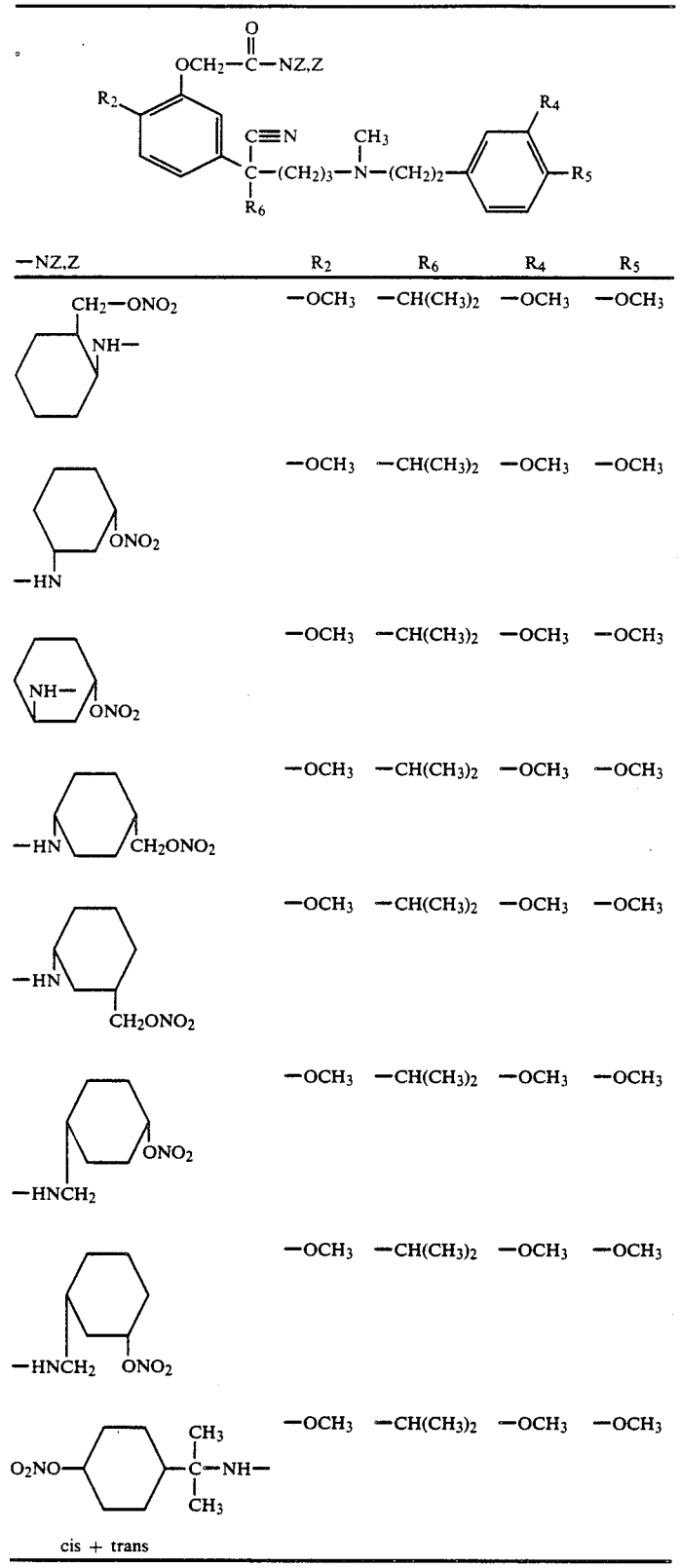

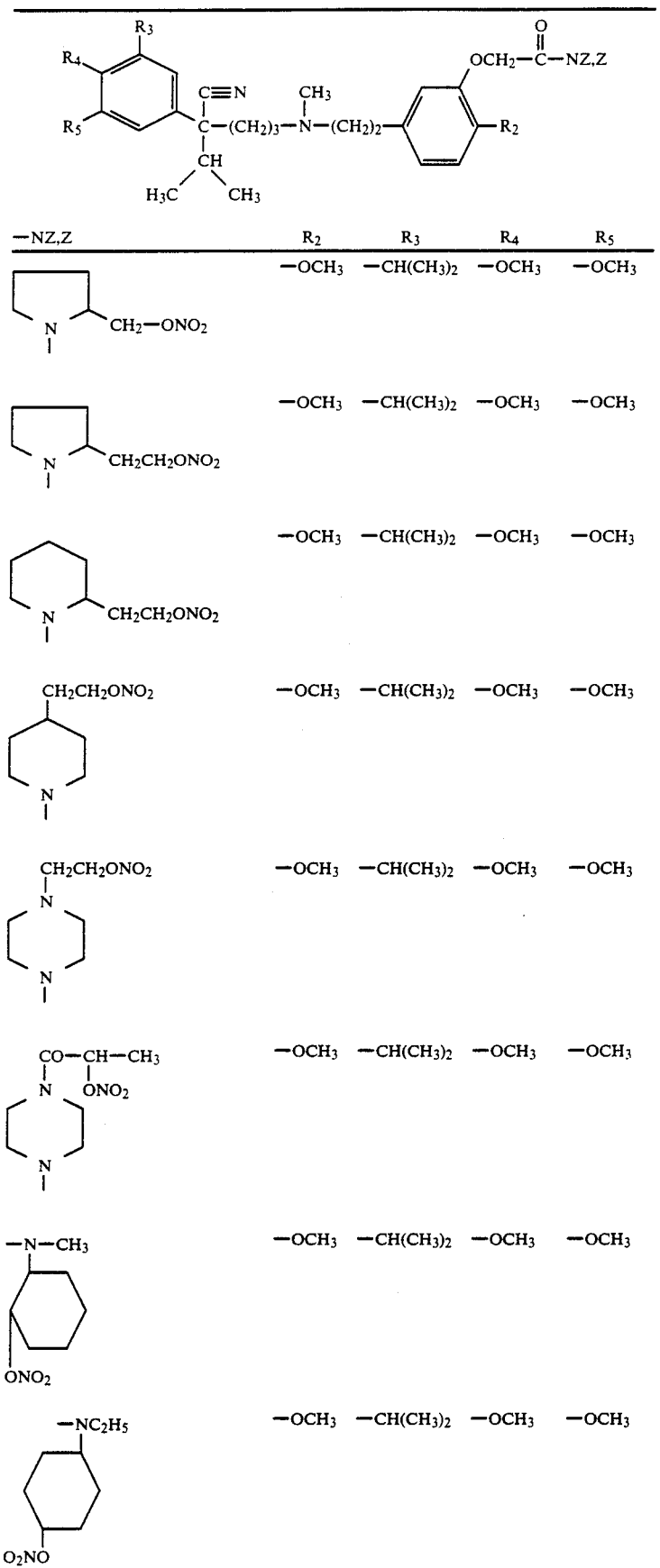

| —NZ,Z | R₂ | R₃ | R₄ | R₅ |
|---|---|---|---|---|
| pyrrolidine-CH₂—ONO₂ | —OCH₃ | —CH(CH₃)₂ | —OCH₃ | —OCH₃ |
| pyrrolidine-CH₂CH₂ONO₂ | —OCH₃ | —CH(CH₃)₂ | —OCH₃ | —OCH₃ |
| piperidine-CH₂CH₂ONO₂ | —OCH₃ | —CH(CH₃)₂ | —OCH₃ | —OCH₃ |
| 4-(CH₂CH₂ONO₂)piperidine | —OCH₃ | —CH(CH₃)₂ | —OCH₃ | —OCH₃ |
| piperazine-CH₂CH₂ONO₂ | —OCH₃ | —CH(CH₃)₂ | —OCH₃ | —OCH₃ |
| piperazine-CO—CH(ONO₂)—CH₃ | —OCH₃ | —CH(CH₃)₂ | —OCH₃ | —OCH₃ |
| —N(CH₃)-cyclohexyl-ONO₂ | —OCH₃ | —CH(CH₃)₂ | —OCH₃ | —OCH₃ |
| —N(C₂H₅)-cyclohexyl-ONO₂ | —OCH₃ | —CH(CH₃)₂ | —OCH₃ | —OCH₃ |

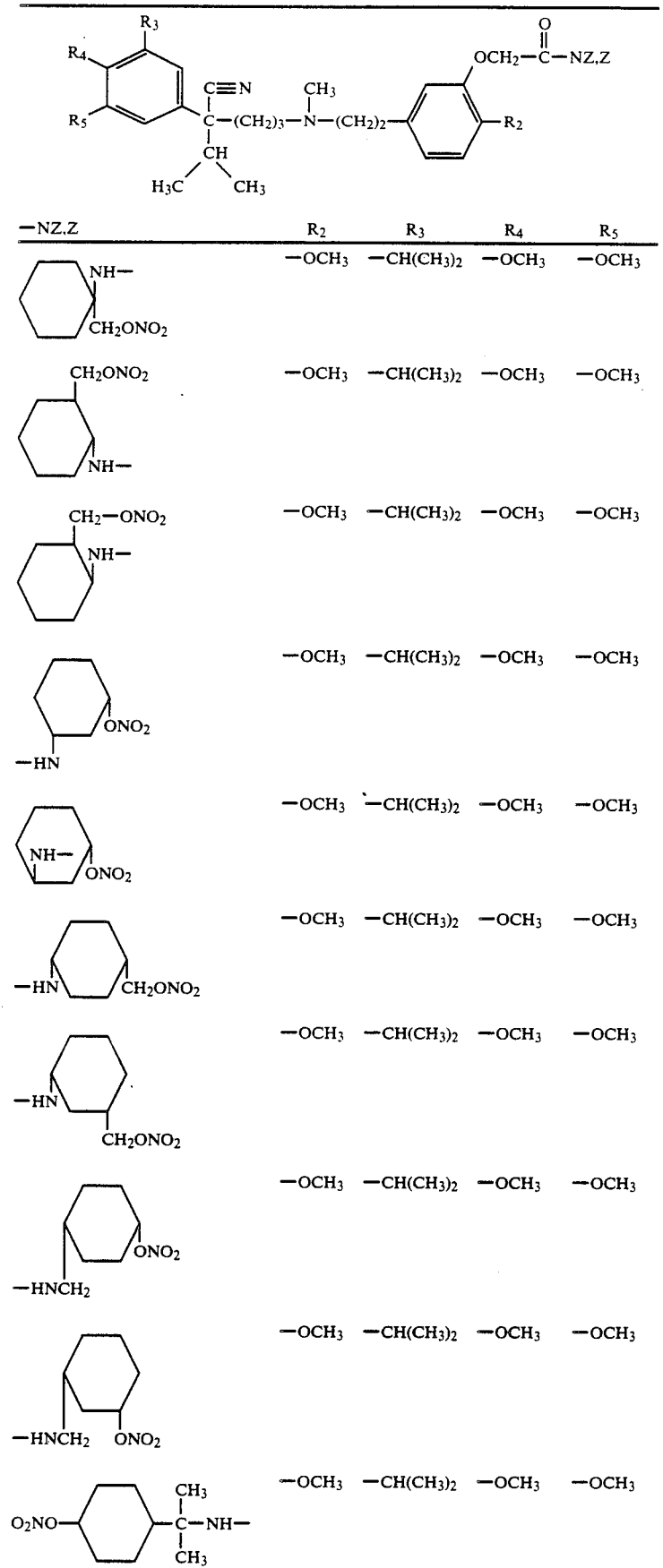

-continued

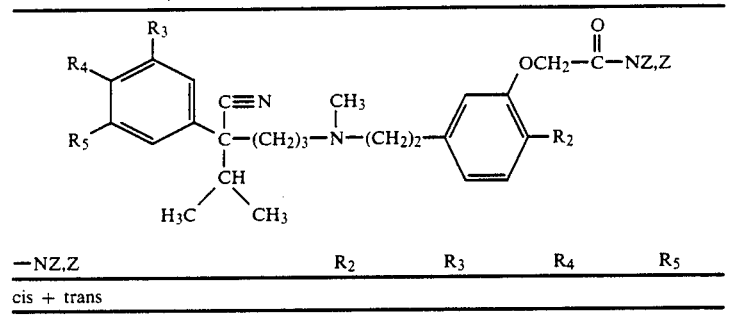

| —NZ,Z | R$_2$ | R$_3$ | R$_4$ | R$_5$ |
|---|---|---|---|---|
| cis + trans | | | | |

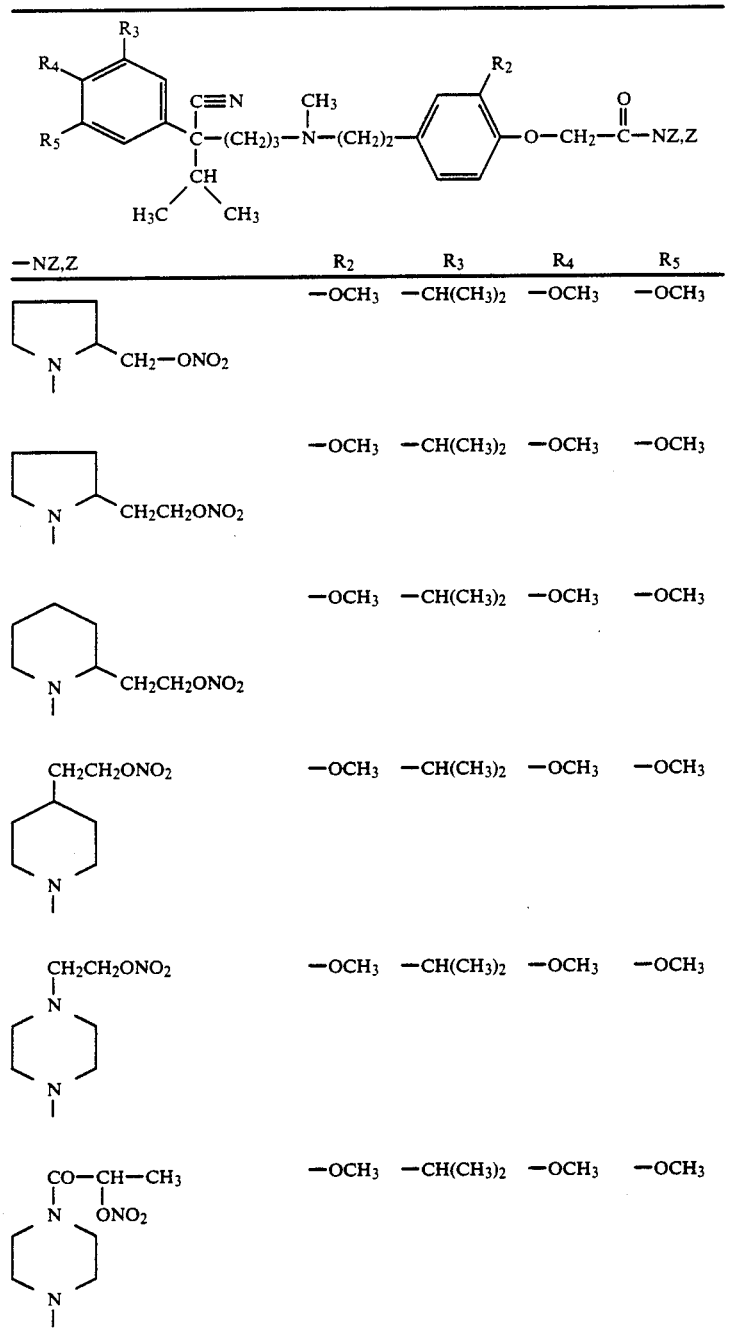

| —NZ,Z | R$_2$ | R$_3$ | R$_4$ | R$_5$ |
|---|---|---|---|---|
| N-methylpyrrolidinyl-CH$_2$—ONO$_2$ | —OCH$_3$ | —CH(CH$_3$)$_2$ | —OCH$_3$ | —OCH$_3$ |
| N-methylpyrrolidinyl-CH$_2$CH$_2$ONO$_2$ | —OCH$_3$ | —CH(CH$_3$)$_2$ | —OCH$_3$ | —OCH$_3$ |
| N-methylpiperidinyl-CH$_2$CH$_2$ONO$_2$ | —OCH$_3$ | —CH(CH$_3$)$_2$ | —OCH$_3$ | —OCH$_3$ |
| 4-(CH$_2$CH$_2$ONO$_2$)-piperidinyl | —OCH$_3$ | —CH(CH$_3$)$_2$ | —OCH$_3$ | —OCH$_3$ |
| piperazinyl-CH$_2$CH$_2$ONO$_2$ | —OCH$_3$ | —CH(CH$_3$)$_2$ | —OCH$_3$ | —OCH$_3$ |
| piperazinyl-CO—CH(ONO$_2$)—CH$_3$ | —OCH$_3$ | —CH(CH$_3$)$_2$ | —OCH$_3$ | —OCH$_3$ |

-continued
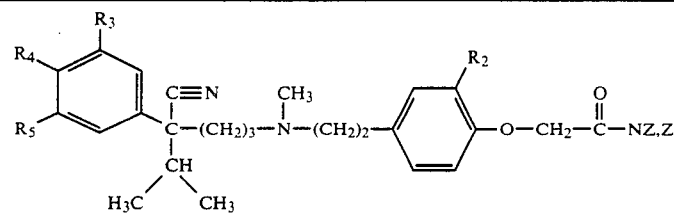
| −NZ,Z | R₂ | R₃ | R₄ | R₅ |
|---|---|---|---|---|
| 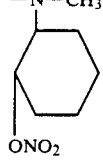 | −OCH₃ | −CH(CH₃)₂ | −OCH₃ | −OCH₃ |
|  | −OCH₃ | −CH(CH₃)₂ | −OCH₃ | −OCH₃ |
| 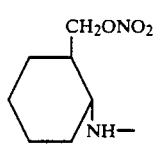 | −OCH₃ | −CH(CH₃)₂ | −OCH₃ | −OCH₃ |
| 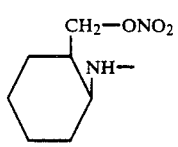 | −OCH₃ | −CH(CH₃)₂ | −OCH₃ | −OCH₃ |
| 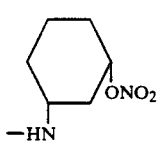 | −OCH₃ | −CH(CH₃)₂ | −OCH₃ | −OCH₃ |
| 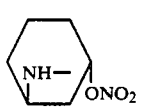 | −OCH₃ | −CH(CH₃)₂ | −OCH₃ | −OCH₃ |
| 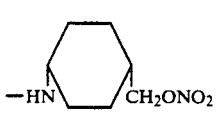 | −OCH₃ | −CH(CH₃)₂ | −OCH₃ | −OCH₃ |
| 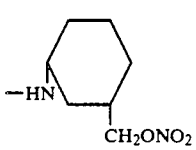 | −OCH₃ | −CH(CH₃)₂ | −OCH₃ | −OCH₃ |

-continued

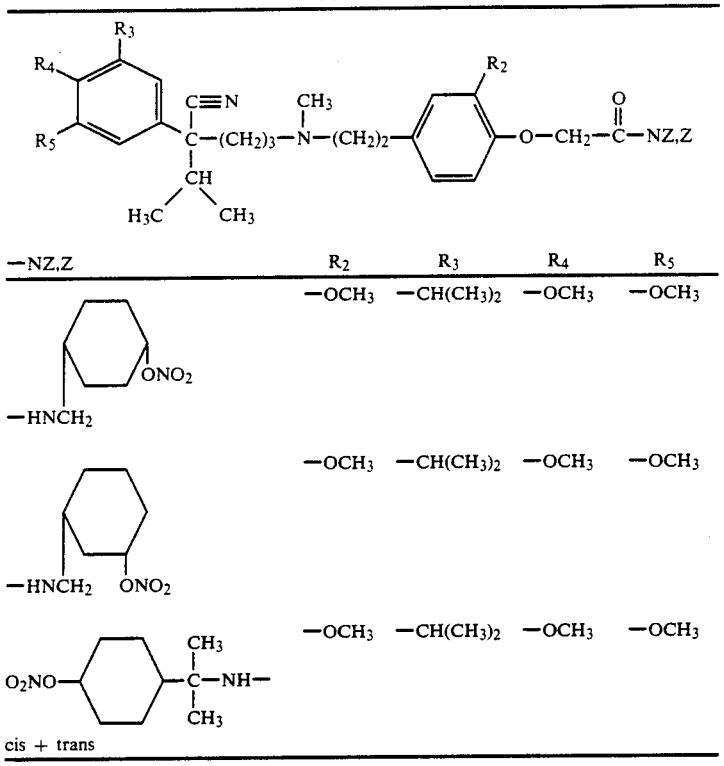

| —NZ,Z | $R_2$ | $R_3$ | $R_4$ | $R_5$ |
|---|---|---|---|---|
| —HNCH$_2$—(cyclohexyl-ONO$_2$) | —OCH$_3$ | —CH(CH$_3$)$_2$ | —OCH$_3$ | —OCH$_3$ |
| —HNCH$_2$—(cyclohexyl-ONO$_2$) | —OCH$_3$ | —CH(CH$_3$)$_2$ | —OCH$_3$ | —OCH$_3$ |
| O$_2$NO—(cyclohexyl)—C(CH$_3$)$_2$—NH— cis + trans | —OCH$_3$ | —CH(CH$_3$)$_2$ | —OCH$_3$ | —OCH$_3$ |

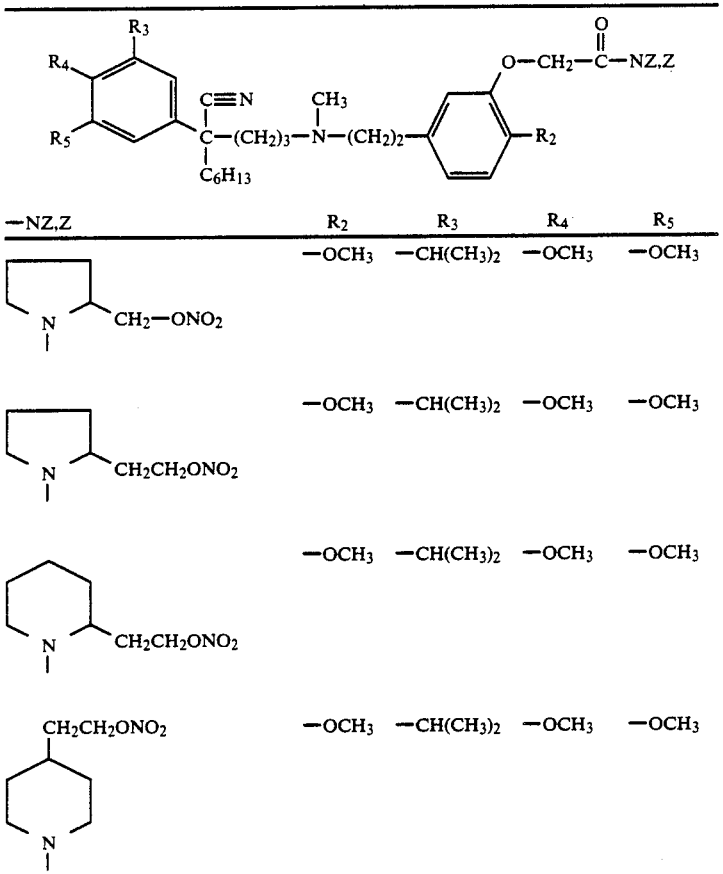

| —NZ,Z | $R_2$ | $R_3$ | $R_4$ | $R_5$ |
|---|---|---|---|---|
| pyrrolidinyl-CH$_2$—ONO$_2$ | —OCH$_3$ | —CH(CH$_3$)$_2$ | —OCH$_3$ | —OCH$_3$ |
| pyrrolidinyl-CH$_2$CH$_2$ONO$_2$ | —OCH$_3$ | —CH(CH$_3$)$_2$ | —OCH$_3$ | —OCH$_3$ |
| piperidinyl-CH$_2$CH$_2$ONO$_2$ | —OCH$_3$ | —CH(CH$_3$)$_2$ | —OCH$_3$ | —OCH$_3$ |
| 4-(CH$_2$CH$_2$ONO$_2$)-piperidinyl | —OCH$_3$ | —CH(CH$_3$)$_2$ | —OCH$_3$ | —OCH$_3$ |

-continued
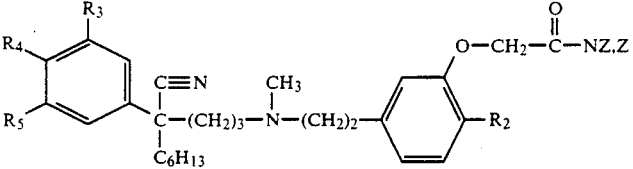
| —NZ,Z | R$_2$ | R$_3$ | R$_4$ | R$_5$ |
|---|---|---|---|---|
| 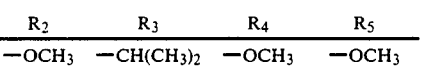 | —OCH$_3$ | —CH(CH$_3$)$_2$ | —OCH$_3$ | —OCH$_3$ |
| 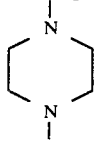 | —OCH$_3$ | —CH(CH$_3$)$_2$ | —OCH$_3$ | —OCH$_3$ |
| 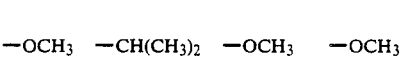 | —OCH$_3$ | —CH(CH$_3$)$_2$ | —OCH$_3$ | —OCH$_3$ |
| 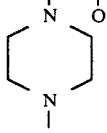 | —OCH$_3$ | —CH(CH$_3$)$_2$ | —OCH$_3$ | —OCH$_3$ |
| 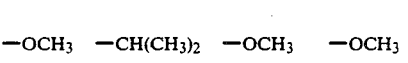 | —OCH$_3$ | —CH(CH$_3$)$_2$ | —OCH$_3$ | —OCH$_3$ |
| 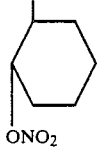 | —OCH$_3$ | —CH(CH$_3$)$_2$ | —OCH$_3$ | —OCH$_3$ |
| 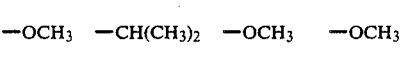 | —OCH$_3$ | —CH(CH$_3$)$_2$ | —OCH$_3$ | —OCH$_3$ |
| 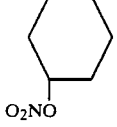 | —OCH$_3$ | —CH(CH$_3$)$_2$ | —OCH$_3$ | —OCH$_3$ |
| 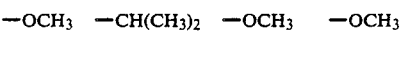 | —OCH$_3$ | —CH(CH$_3$)$_2$ | —OCH$_3$ | —OCH$_3$ |

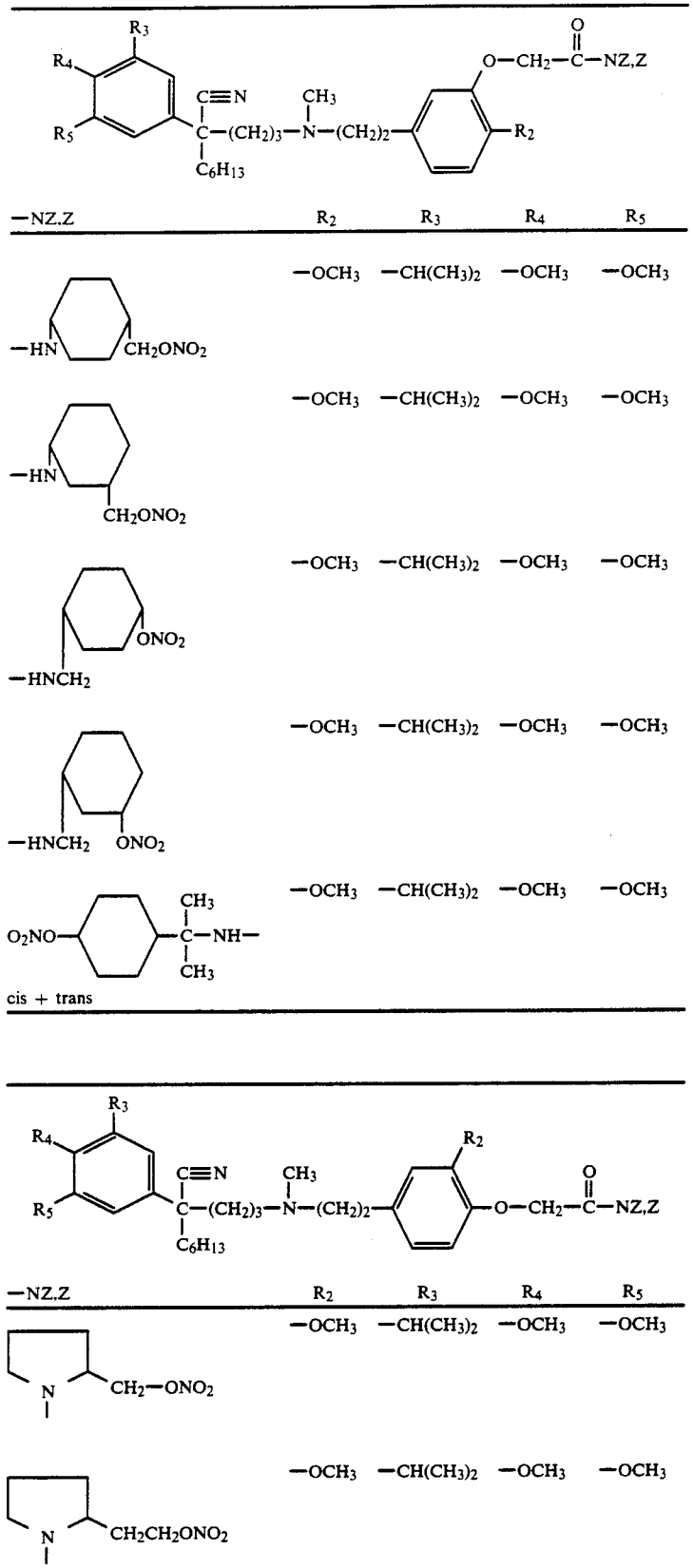

-continued
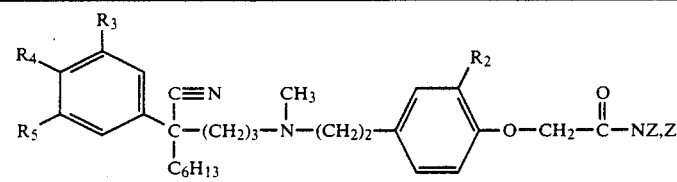
| —NZ,Z | R₂ | R₃ | R₄ | R₅ |
|---|---|---|---|---|
| 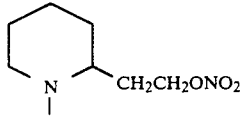 | —OCH₃ | —CH(CH₃)₂ | —OCH₃ | —OCH₃ |
| 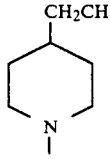 | —OCH₃ | —CH(CH₃)₂ | —OCH₃ | —OCH₃ |
| 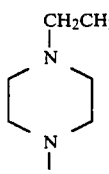 | —OCH₃ | —CH(CH₃)₂ | —OCH₃ | —OCH₃ |
| 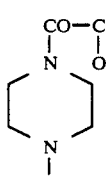 | —OCH₃ | —CH(CH₃)₂ | —OCH₃ | —OCH₃ |
| 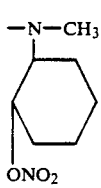 | —OCH₃ | —CH(CH₃)₂ | —OCH₃ | —OCH₃ |
| 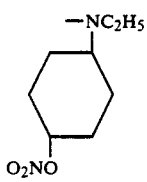 | —OCH₃ | —CH(CH₃)₂ | —OCH₃ | —OCH₃ |
| 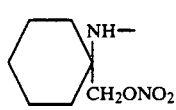 | —OCH₃ | —CH(CH₃)₂ | —OCH₃ | —OCH₃ |
| 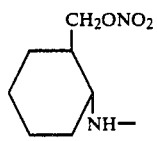 | —OCH₃ | —CH(CH₃)₂ | —OCH₃ | —OCH₃ |

-continued
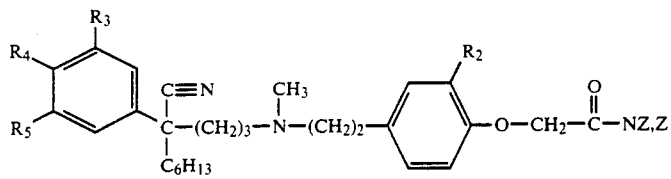
| —NZ,Z | R2 | R3 | R4 | R5 |
|---|---|---|---|---|
| 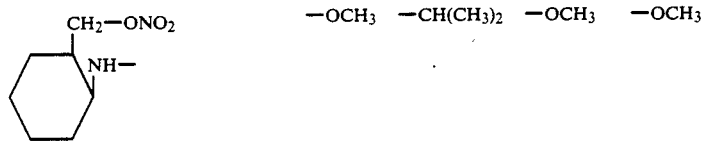 | —OCH3 | —CH(CH3)2 | —OCH3 | —OCH3 |
|  | —OCH3 | —CH(CH3)2 | —OCH3 | —OCH3 |
| 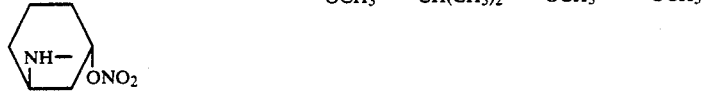 | —OCH3 | —CH(CH3)2 | —OCH3 | —OCH3 |
| 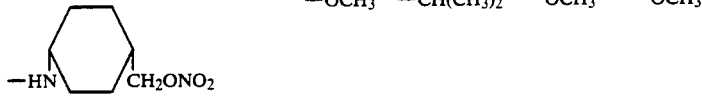 | —OCH3 | —CH(CH3)2 | —OCH3 | —OCH3 |
| 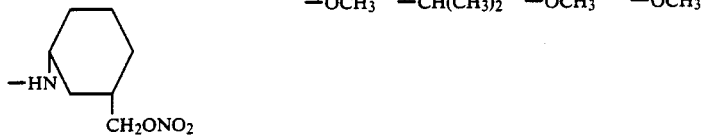 | —OCH3 | —CH(CH3)2 | —OCH3 | —OCH3 |
| 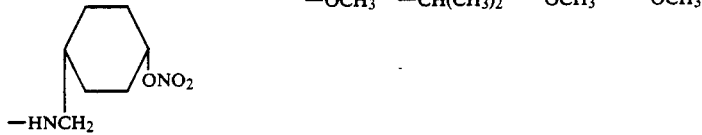 | —OCH3 | —CH(CH3)2 | —OCH3 | —OCH3 |
|  | —OCH3 | —CH(CH3)2 | —OCH3 | —OCH3 |
| 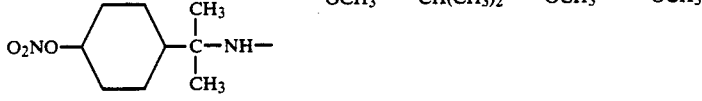<br>cis + trans | —OCH3 | —CH(CH3)2 | —OCH3 | —OCH3 |

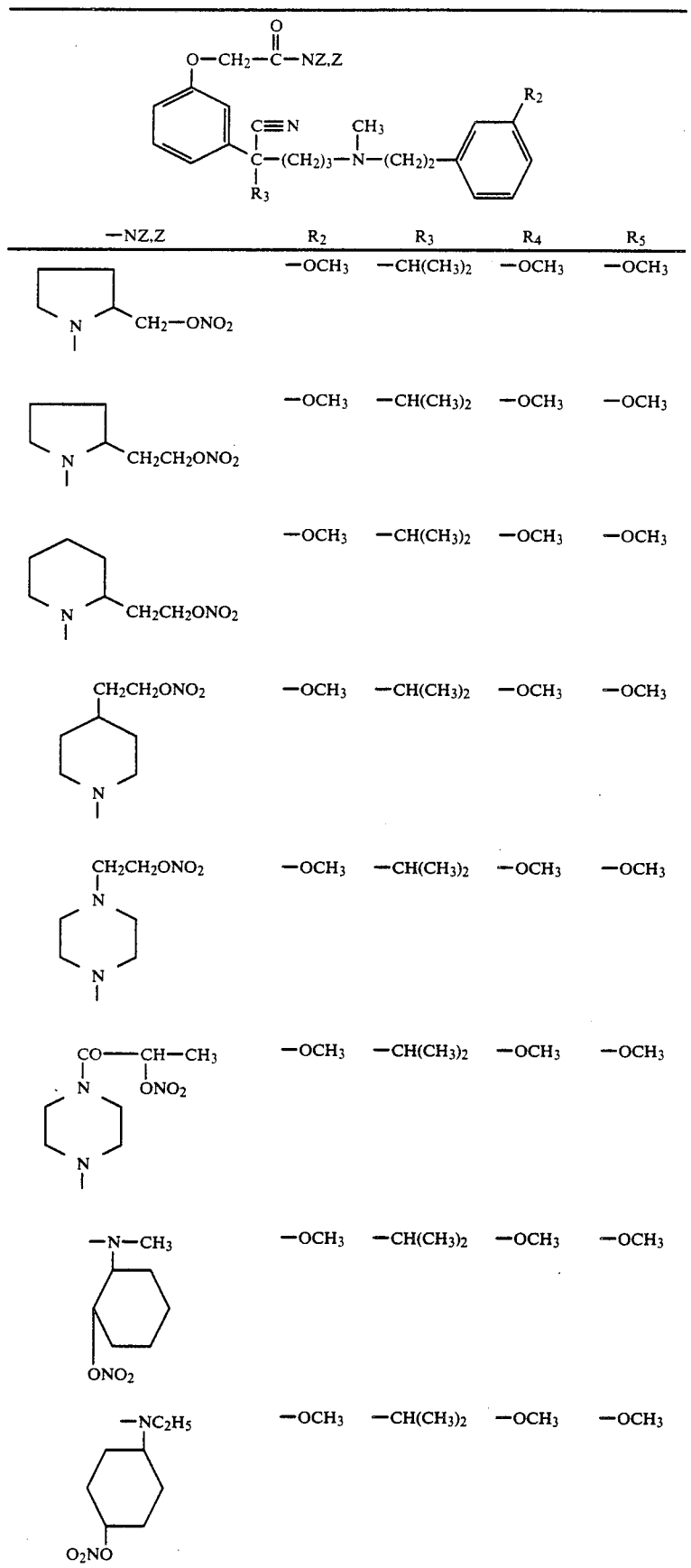

-continued
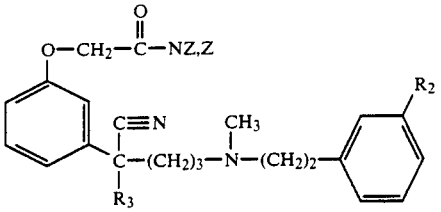
| —NZ,Z | $R_2$ | $R_3$ | $R_4$ | $R_5$ |
|---|---|---|---|---|
| 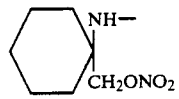 | —OCH$_3$ | —CH(CH$_3$)$_2$ | —OCH$_3$ | —OCH$_3$ |
| 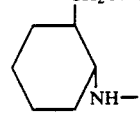 | —OCH$_3$ | —CH(CH$_3$)$_2$ | —OCH$_3$ | —OCH$_3$ |
| 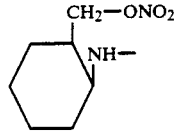 | —OCH$_3$ | —CH(CH$_3$)$_2$ | —OCH$_3$ | —OCH$_3$ |
| 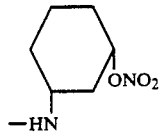 | —OCH$_3$ | —CH(CH$_3$)$_2$ | —OCH$_3$ | —OCH$_3$ |
| 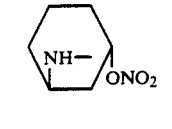 | —OCH$_3$ | —CH(CH$_3$)$_2$ | —OCH$_3$ | —OCH$_3$ |
| 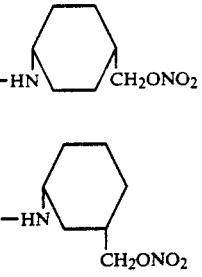 | —OCH$_3$ | —CH(CH$_3$)$_2$ | —OCH$_3$ | —OCH$_3$ |
| 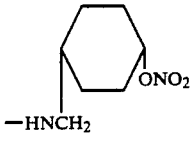 | —OCH$_3$ | —CH(CH$_3$)$_2$ | —OCH$_3$ | —OCH$_3$ |
| 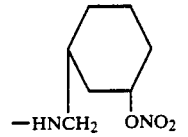 | —OCH$_3$ | —CH(CH$_3$)$_2$ | —OCH$_3$ | —OCH$_3$ |
| | —OCH$_3$ | —CH(CH$_3$)$_2$ | —OCH$_3$ | —OCH$_3$ |

-continued
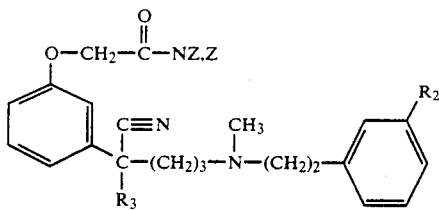
| —NZ.Z | R$_2$ | R$_3$ | R$_4$ | R$_5$ |
|---|---|---|---|---|
| 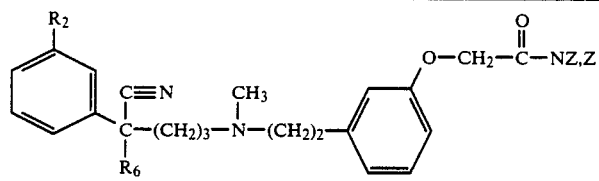 cis + trans | —OCH$_3$ | —CH(CH$_3$)$_2$ | —OCH$_3$ | —OCH$_3$ |
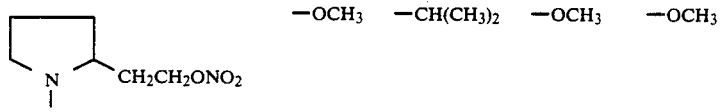
| —NZ.Z | R$_2$ | R$_6$ | R$_4$ | R$_5$ |
|---|---|---|---|---|
| 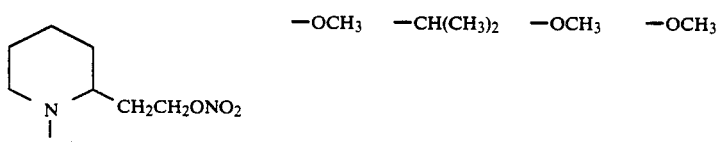 | —OCH$_3$ | —CH(CH$_3$)$_2$ | —OCH$_3$ | —OCH$_3$ |
| 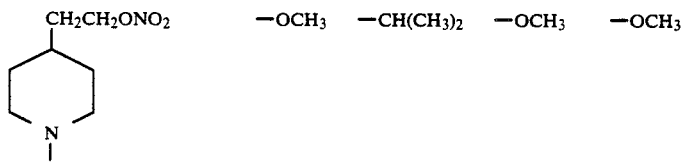 | —OCH$_3$ | —CH(CH$_3$)$_2$ | —OCH$_3$ | —OCH$_3$ |
| 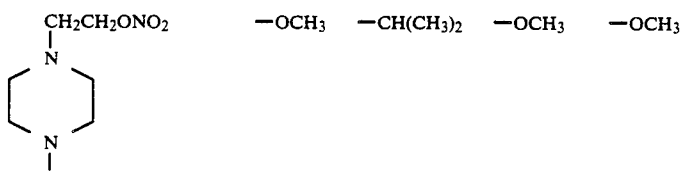 | —OCH$_3$ | —CH(CH$_3$)$_2$ | —OCH$_3$ | —OCH$_3$ |

-continued

| —NZ.Z | R₂ | R₆ | R₄ | R₅ |
|---|---|---|---|---|
| 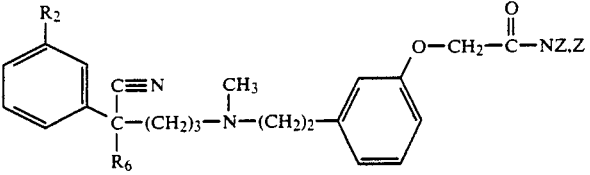 piperazine-CO-CH(CH₃)-ONO₂, N-methyl | —OCH₃ | —CH(CH₃)₂ | —OCH₃ | —OCH₃ |
|  N(CH₃)-cyclohexyl-ONO₂ | —OCH₃ | —CH(CH₃)₂ | —OCH₃ | —OCH₃ |
| 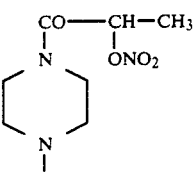 N(C₂H₅)-cyclohexyl-ONO₂ | —OCH₃ | —CH(CH₃)₂ | —OCH₃ | —OCH₃ |
| 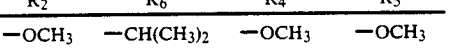 NH-cyclohexyl-CH₂ONO₂ | —OCH₃ | —CH(CH₃)₂ | —OCH₃ | —OCH₃ |
| 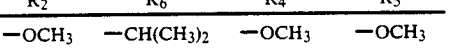 NH-cyclohexyl-CH₂ONO₂ | —OCH₃ | —CH(CH₃)₂ | —OCH₃ | —OCH₃ |
| 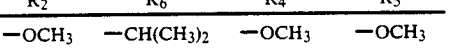 NH-cyclohexyl-CH₂ONO₂ | —OCH₃ | —CH(CH₃)₂ | —OCH₃ | —OCH₃ |
| 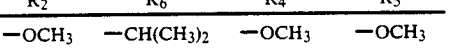 HN-cyclohexyl-ONO₂ | —OCH₃ | —CH(CH₃)₂ | —OCH₃ | —OCH₃ |
| 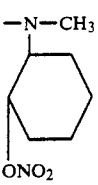 NH-cyclohexyl-ONO₂ | —OCH₃ | —CH(CH₃)₂ | —OCH₃ | —OCH₃ |
| 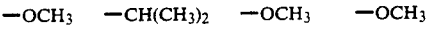 HN-cyclohexyl-CH₂ONO₂ | —OCH₃ | —CH(CH₃)₂ | —OCH₃ | —OCH₃ |

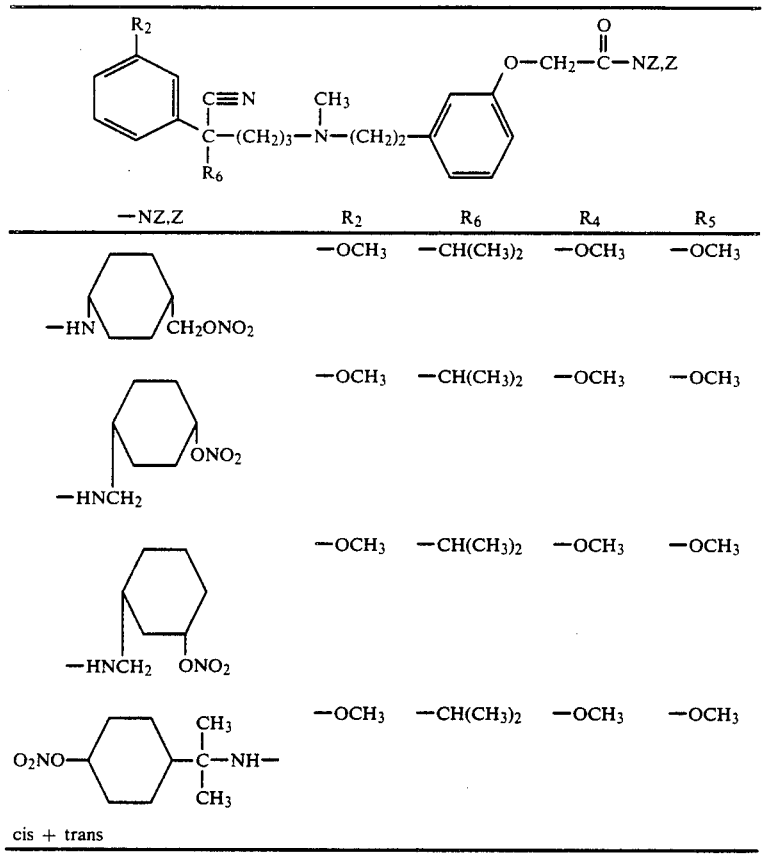

81
-continued
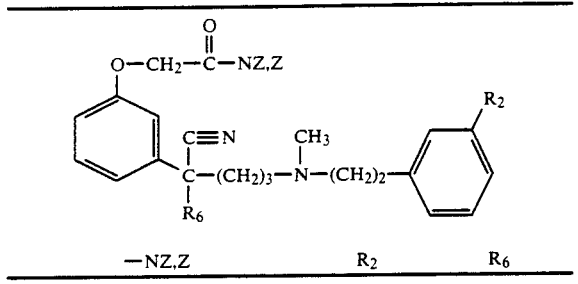
| —NZ,Z | R₂ | R₆ |
|---|---|---|
| 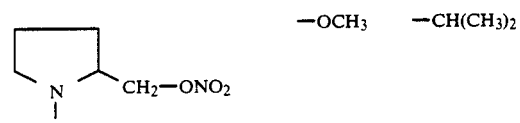 | —OCH₃ | —CH(CH₃)₂ |
| 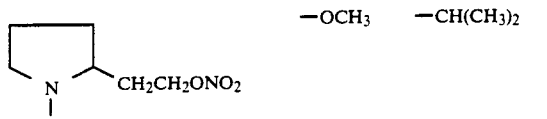 | —OCH₃ | —CH(CH₃)₂ |
| 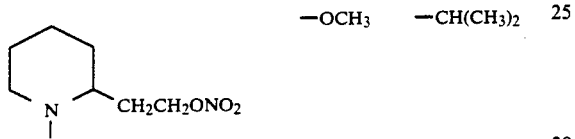 | —OCH₃ | —CH(CH₃)₂ |
| 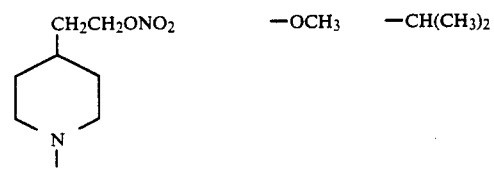 | —OCH₃ | —CH(CH₃)₂ |
| 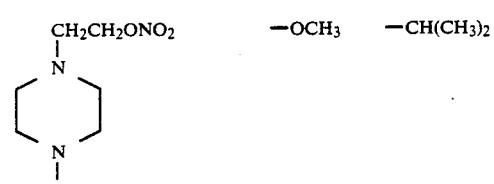 | —OCH₃ | —CH(CH₃)₂ |
| 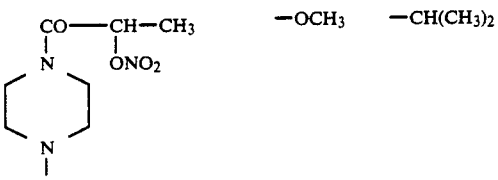 | —OCH₃ | —CH(CH₃)₂ |
| 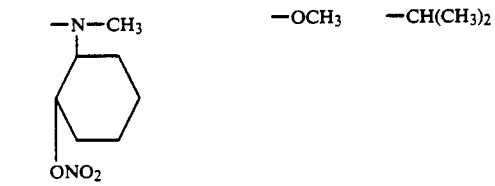 | —OCH₃ | —CH(CH₃)₂ |
| 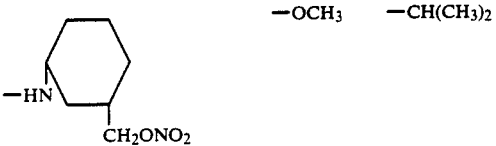 | —OCH₃ | —CH(CH₃)₂ |
82
-continued
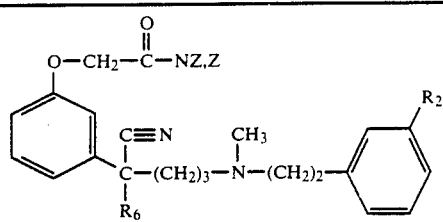
| —NZ,Z | R₂ | R₆ |
|---|---|---|
| 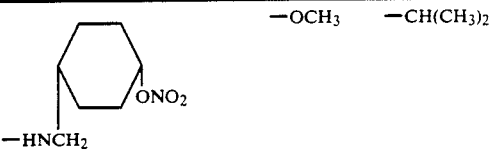 | —OCH₃ | —CH(CH₃)₂ |
| 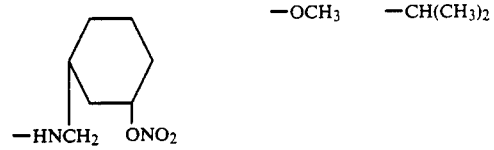 | —OCH₃ | —CH(CH₃)₂ |
| 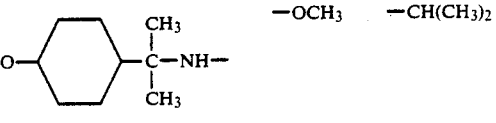 | —OCH₃ | —CH(CH₃)₂ |
cis + trans
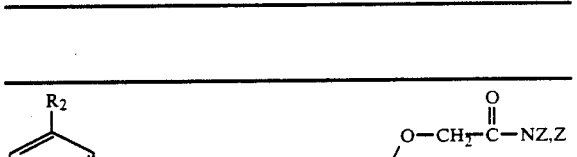
| —NZ,Z | R₂ | R₆ |
|---|---|---|
| 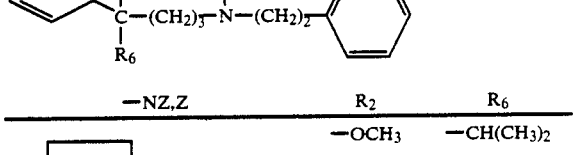 | —OCH₃ | —CH(CH₃)₂ |
| 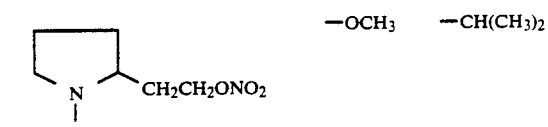 | —OCH₃ | —CH(CH₃)₂ |
| 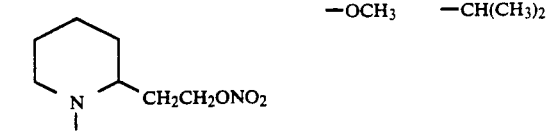 | —OCH₃ | —CH(CH₃)₂ |
| 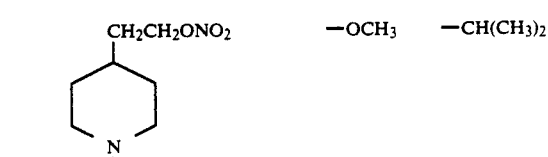 | —OCH₃ | —CH(CH₃)₂ |

-continued
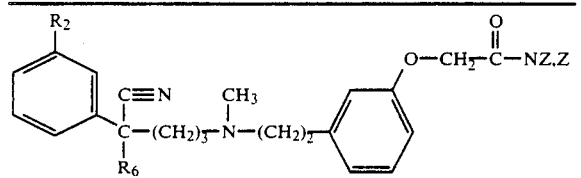
| —NZ,Z | R$_2$ | R$_6$ |
|---|---|---|
| 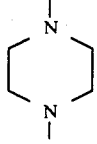 CH$_2$CH$_2$ONO$_2$ | —OCH$_3$ | —CH(CH$_3$)$_2$ |
| 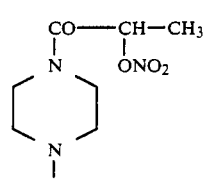 | —OCH$_3$ | —CH(CH$_3$)$_2$ |
| 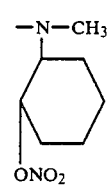 | —OCH$_3$ | —CH(CH$_3$)$_2$ |
| 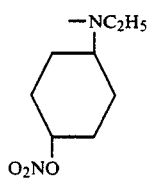 | —OCH$_3$ | —CH(CH$_3$)$_2$ |
| 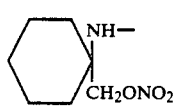 | —OCH$_3$ | —CH(CH$_3$)$_2$ |
| 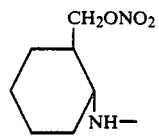 | —OCH$_3$ | —CH(CH$_3$)$_2$ |
| 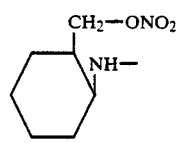 | —OCH$_3$ | —CH(CH$_3$)$_2$ |
| 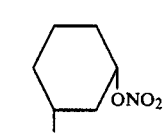 | —OCH$_3$ | —CH(CH$_3$)$_2$ |
| 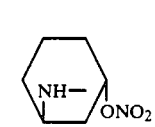 | —OCH$_3$ | —CH(CH$_3$)$_2$ |
-continued
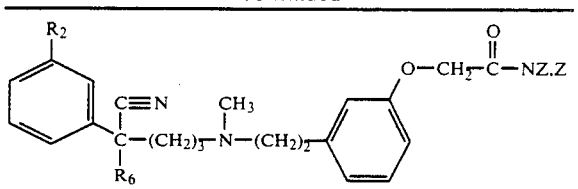
| —NZ,Z | R$_2$ | R$_6$ |
|---|---|---|
| 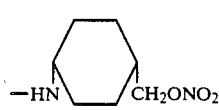 | —OCH$_3$ | —CH(CH$_3$)$_2$ |
| 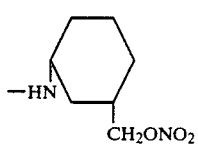 | —OCH$_3$ | —CH(CH$_3$)$_2$ |
| 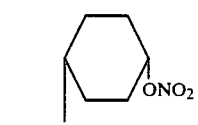 | —OCH$_3$ | —CH(CH$_3$)$_2$ |
| 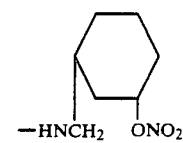 | —OCH$_3$ | —CH(CH$_3$)$_2$ |
| 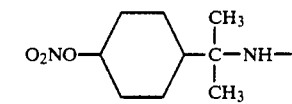 | —OCH$_3$ | —CH(CH$_3$)$_2$ |
cis + trans
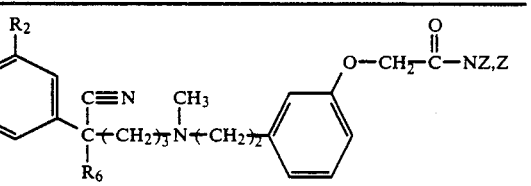
| —NZ,Z | R$_2$ | R$_6$ |
|---|---|---|
| 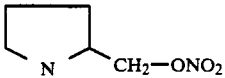 | —OCH$_3$ | —C$_6$H$_{13}$ |
|  | —OCH$_3$ | —C$_6$H$_{13}$ |

-continued

![Structure with R2, CN, CH3, NZ,Z groups]

| —NZ,Z | R₂ | R₆ |
|---|---|---|
| piperidine-N-CH₃ with CH₂CH₂ONO₂ at 2-position | —OCH₃ | —C₆H₁₃ |
| piperidine-N-CH₃ with CH₂CH₂ONO₂ at 4-position | —OCH₃ | —C₆H₁₃ |
| piperazine with CH₂CH₂ONO₂ | —OCH₃ | —C₆H₁₃ |
| piperazine with CO-CH(ONO₂)-CH₃ | —OCH₃ | —C₆H₁₃ |
| cyclohexyl-N(CH₃)- with ONO₂ | —OCH₃ | —C₆H₁₃ |
| cyclohexyl-N(C₂H₅)- with O₂NO | —OCH₃ | —C₆H₁₃ |
| cyclohexyl-NH- with CH₂ONO₂ | —OCH₃ | —C₆H₁₃ |
| cyclohexyl with CH₂ONO₂ and NH— | —OCH₃ | —C₆H₁₃ |

-continued

![Structure with R2, CN, CH3, NZ,Z groups]

| —NZ,Z | R₂ | R₆ |
|---|---|---|
| cyclohexyl-NH- with CH₂—ONO₂ | —OCH₃ | —C₆H₁₃ |
| cyclohexyl with ONO₂ and —HN | —OCH₃ | —C₆H₁₃ |
| cyclohexyl with NH and ONO₂ | —OCH₃ | —C₆H₁₃ |
| cyclohexyl with CH₂ONO₂ and —HN | —OCH₃ | —C₆H₁₃ |
| cyclohexyl with CH₂ONO₂ and —HN | —OCH₃ | —C₆H₁₃ |
| cyclohexyl with ONO₂ and —HNCH₂ | —OCH₃ | —C₆H₁₃ |
| cyclohexyl with ONO₂ and —HNCH₂ | —OCH₃ | —C₆H₁₃ |
| O₂NO-cyclohexyl-C(CH₃)₂-NH— | —OCH₃ | —C₆H₁₃ | cis + trans

| Y | R₃ | R₆ |
|---|---|---|
| $-CH_2-\underset{\underset{CH_3}{\mid}}{CH}-ONO_2$ | $-OCH_3$ | $-C_6H_{13}$ |
| $-\underset{\underset{CH_3}{\mid}}{CH}-(CH_2)_2-ONO_2$ | $-OCH_3$ | $-C_6H_{13}$ |
| $-(CH_2)_4-ONO_2$ | $-OCH_3$ | $-C_6H_{13}$ |
| $-(CH_2)_3-\underset{\underset{CH_3}{\mid}}{CH}-ONO_2$ | $-OCH_3$ | $-C_6H_{13}$ |
| $-CH_2-O-CH_2-CH_2-ONO_2$ | $-OCH_3$ | $-C_6H_{13}$ |
| $-CH_2-S-CH_2-CH_2-ONO_2$ | $-OCH_3$ | $-C_6H_{13}$ |
| $-\underset{\underset{CH_3}{\mid}}{CH}-S-CH_2-CH_2-ONO_2$ | $-OCH_3$ | $-C_6H_{13}$ |
| $-CH_2-S-\text{(cyclopentyl)}-ONO_2$ | $-OCH_3$ | $-C_6H_{13}$ |
| $-CH_2-S-\text{(cyclohexyl)}-ONO_2$ | $-OCH_3$ | $-C_6H_{13}$ |
| $-CO-\underset{\underset{CH_3}{\mid}}{\overset{\overset{CH_3}{\mid}}{C}}-CH_2-ONO_2$ | $-OCH_3$ | $-C_6H_{13}$ |
| $-CO-CH_2-\text{(cyclohexyl)}-ONO_2$ | $-OCH_3$ | $-C_6H_{13}$ |
| $O_2NO-\text{(cyclohexyl)}-CH_2-CO-$ | $-OCH_3$ | $-C_6H_{13}$ |
| $O_2NO-\text{(cyclohexyl)}-CH_2-CO-$ | $-OCH_3$ | $-C_6H_{13}$ |
| $-\overset{\overset{O}{\|}}{C}-(CH_2)_3-ONO_2$ | $-OCH_3$ | $-C_6H_{13}$ |

(Table 87 structure and Table 88 structure both show the parent compound with substituents $R_3$, $R_6$, and Y, with identical Y values listed for both tables.)

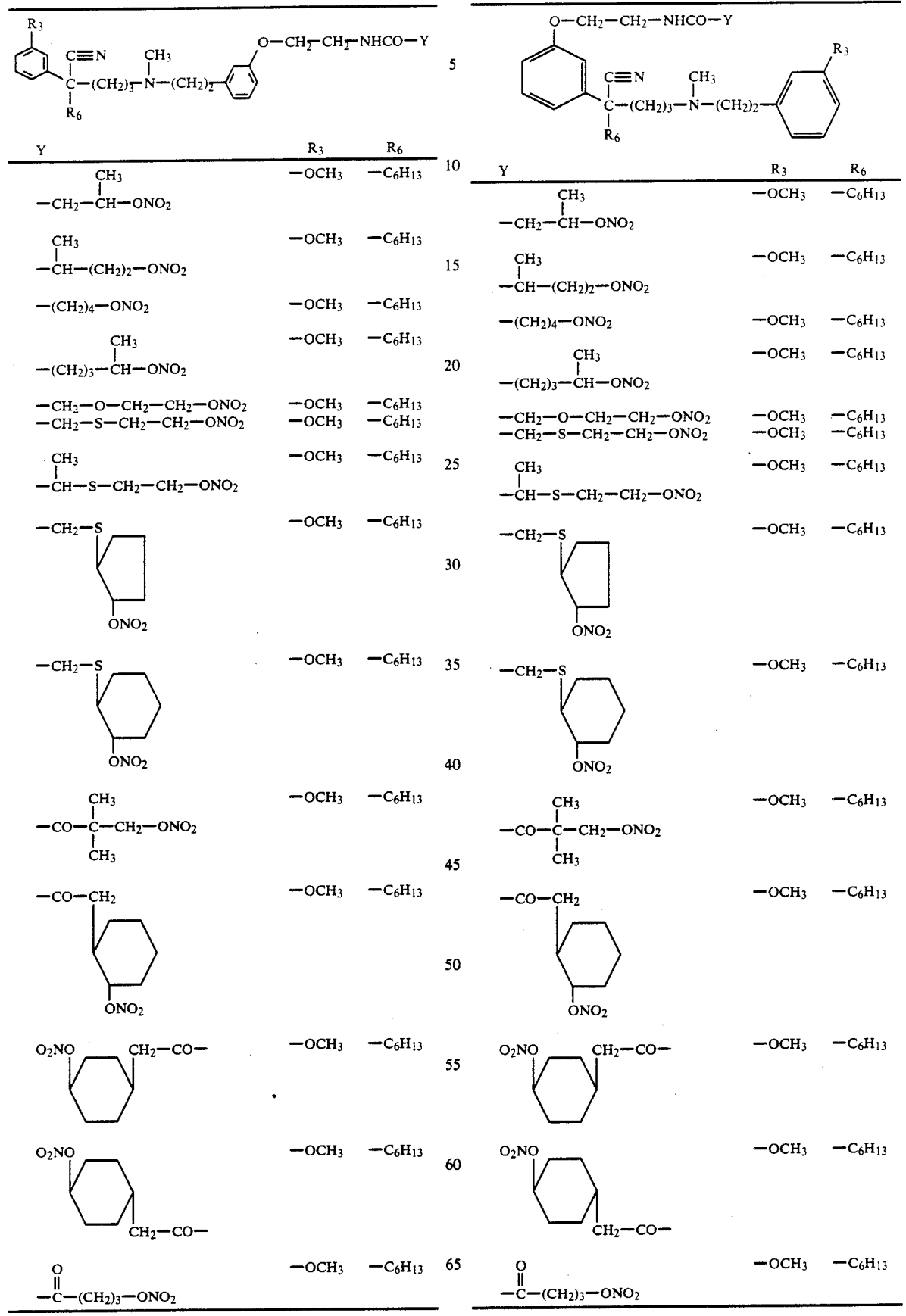

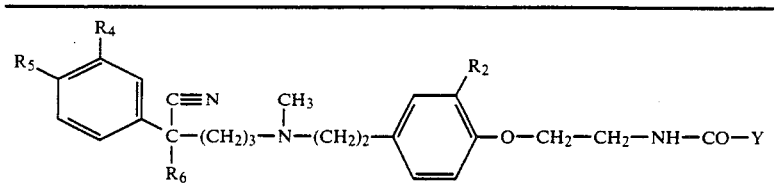

| Y | $R_2$ | $R_6$ | $R_4$ | $R_5$ |
|---|---|---|---|---|
| $-CH_2-\underset{\underset{CH_3}{\|}}{CH}-ONO_2$ | $-OCH_3$ | $-CH(CH_3)_2$ | $-OCH_3$ | $-OCH_3$ |
| $-\underset{\underset{CH_3}{\|}}{CH}-(CH_2)_2-ONO_2$ | $-OCH_3$ | " | $-OCH_3$ | $-OCH_3$ |
| $-(CH_2)_4-ONO_2$ | $-OCH_3$ | " | $-OCH_3$ | $-OCH_3$ |
| $-(CH_2)_3-\underset{\underset{CH_3}{\|}}{CH}-ONO_2$ | $-OCH_3$ | " | $-OCH_3$ | $-OCH_3$ |
| $-CH_2-O-CH_2-CH_2-ONO_2$ | $-OCH_3$ | " | $-OCH_3$ | $-OCH_3$ |
| $-CH_2-S-CH_2-CH_2-ONO_2$ | $-OCH_3$ | " | $-OCH_3$ | $-OCH_3$ |
| $-\underset{\underset{CH_3}{\|}}{CH}-S-CH_2-CH_2-ONO_2$ | $-OCH_3$ | " | $-OCH_3$ | $-OCH_3$ |
| $-CH_2-S-$ cyclopentyl-$ONO_2$ | $-OCH_3$ | " | $-OCH_3$ | $-OCH_3$ |
| $-CH_2-S-$ cyclohexyl-$ONO_2$ | $-OCH_3$ | " | $-OCH_3$ | $-OCH_3$ |
| $-\underset{\underset{CH_3}{\|}}{\overset{\overset{CH_3}{\|}}{C}}-CH_2-ONO_2$ | $-OCH_3$ | " | $-OCH_3$ | $-OCH_3$ |
| $-CH_2-$cyclohexyl-$ONO_2$ | $-OCH_3$ | " | $-OCH_3$ | $-OCH_3$ |
| $O_2NO-$cyclohexyl-$CH_2-$ | $-OCH_3$ | " | $-OCH_3$ | $-OCH_3$ |
| $O_2NO-$cyclohexyl-$CH_2-$ | $-OCH_3$ | " | $-OCH_3$ | $-OCH_3$ |
| $-(CH_2)_3-ONO_2$ | $-OCH_3$ | " | $-OCH_3$ | $-OCH_3$ |

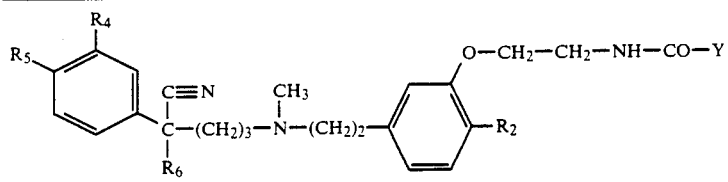

| Y | $R_2$ | $R_6$ | $R_4$ | $R_5$ |
|---|---|---|---|---|
| $-CH_2-\underset{\underset{CH_3}{\|}}{CH}-ONO_2$ | $-OCH_3$ | $-CH(CH_3)_2$ | $-OCH_3$ | $-OCH_3$ |
| $-\underset{\underset{CH_3}{\|}}{CH}-(CH_2)_2-ONO_2$ | $-OCH_3$ | " | $-OCH_3$ | $-OCH_3$ |
| $-(CH_2)_4-ONO_2$ | $-OCH_3$ | " | $-OCH_3$ | $-OCH_3$ |
| $-(CH_2)_3-\underset{\underset{CH_3}{\|}}{CH}-ONO_2$ | $-OCH_3$ | " | $-OCH_3$ | $-OCH_3$ |
| $-CH_2-O-CH_2-CH_2-ONO_2$ | $-OCH_3$ | " | $-OCH_3$ | $-OCH_3$ |
| $-CH_2-S-CH_2-CH_2-ONO_2$ | $-OCH_3$ | " | $-OCH_3$ | $-OCH_3$ |
| $-\underset{\underset{CH_3}{\|}}{CH}-S-CH_2-CH_2-ONO_2$ | $-OCH_3$ | " | $-OCH_3$ | $-OCH_3$ |
| $-CH_2-$ cyclopentyl-$S$-, $ONO_2$ | $-OCH_3$ | " | $-OCH_3$ | $-OCH_3$ |
| $-CH_2-$ cyclohexyl-$S$-, $ONO_2$ | $-OCH_3$ | " | $-OCH_3$ | $-OCH_3$ |
| $-\underset{\underset{CH_3}{\|}}{\overset{\overset{CH_3}{\|}}{C}}-CH_2-ONO_2$ | $-OCH_3$ | " | $-OCH_3$ | $-OCH_3$ |
| $-CH_2-$ cyclohexyl-$ONO_2$ | $-OCH_3$ | " | $-OCH_3$ | $-OCH_3$ |
| $O_2NO-$cyclohexyl$-CH_2-$ | $-OCH_3$ | " | $-OCH_3$ | $-OCH_3$ |
| $O_2NO-$cyclohexyl$-CH_2-$ | $-OCH_3$ | " | $-OCH_3$ | $-OCH_3$ |
| $-(CH_2)_3-ONO_2$ | $-OCH_3$ | " | $-OCH_3$ | $-OCH_3$ |

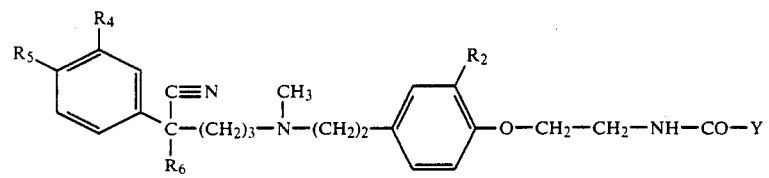

| Y | R₂ | R₆ | R₄ | R₅ |
|---|---|---|---|---|
| -CH₂-CH(CH₃)-ONO₂ | -OCH₃ | -CH(CH₃)₂ | -OCH₃ | -OCH₃ |
| -CH(CH₃)-(CH₂)₂-ONO₂ | -OCH₃ | " | -OCH₃ | -OCH₃ |
| -(CH₂)₄-ONO₂ | -OCH₃ | " | -OCH₃ | -OCH₃ |
| -(CH₂)₃-CH(CH₃)-ONO₂ | -OCH₃ | " | -OCH₃ | -OCH₃ |
| -CH₂-O-CH₂-CH₂-ONO₂ | -OCH₃ | " | -OCH₃ | -OCH₃ |
| -CH₂-S-CH₂-CH₂-ONO₂ | -OCH₃ | " | -OCH₃ | -OCH₃ |
| -CH(CH₃)-S-CH₂-CH₂-ONO₂ | -OCH₃ | " | -OCH₃ | -OCH₃ |
| -CH₂-S-(cyclopentyl-ONO₂) | -OCH₃ | " | -OCH₃ | -OCH₃ |
| -CH₂-S-(cyclohexyl-ONO₂) | -OCH₃ | " | -OCH₃ | -OCH₃ |
| -C(CH₃)₂-CH₂-ONO₂ | -OCH₃ | " | -OCH₃ | -OCH₃ |
| -CH₂-(cyclohexyl-ONO₂) | -OCH₃ | " | -OCH₃ | -OCH₃ |
| O₂NO-(cyclohexyl)-CH₂- | -OCH₃ | " | -OCH₃ | -OCH₃ |
| O₂NO-(cyclohexyl)-CH₂- | -OCH₃ | " | -OCH₃ | -OCH₃ |
| -(CH₂)₃-ONO₂ | -OCH₃ | " | -OCH₃ | -OCH₃ |

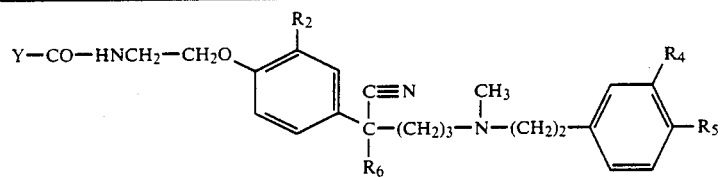

| Y | $R_2$ | $R_6$ | $R_4$ | $R_5$ |
|---|---|---|---|---|
| —CH₂—CH(CH₃)—ONO₂ | —OCH₃ | —CH(CH₃)₂ | —OCH₃ | —OCH₃ |
| —CH(CH₃)—(CH₂)₂—ONO₂ | —OCH₃ | " | —OCH₃ | —OCH₃ |
| —(CH₂)₄—ONO₂ | —OCH₃ | " | —OCH₃ | —OCH₃ |
| —(CH₂)₃—CH(CH₃)—ONO₂ | —OCH₃ | " | —OCH₃ | —OCH₃ |
| —CH₂—O—CH₂—CH₂—ONO₂ | —OCH₃ | " | —OCH₃ | —OCH₃ |
| —CH₂—S—CH₂—CH₂—ONO₂ | —OCH₃ | " | —OCH₃ | —OCH₃ |
| —CH(CH₃)—S—CH₂—CH₂—ONO₂ | —OCH₃ | " | —OCH₃ | —OCH₃ |
| —CH₂—S—(cyclopentyl-ONO₂) | —OCH₃ | " | —OCH₃ | —OCH₃ |
| —CH₂—S—(cyclohexyl-ONO₂) | —OCH₃ | " | —OCH₃ | —OCH₃ |
| —C(CH₃)₂—CH₂—ONO₂ | —OCH₃ | " | —OCH₃ | —OCH₃ |
| —CH₂—(cyclohexyl-ONO₂) | —OCH₃ | " | —OCH₃ | —OCH₃ |
| O₂N—(cyclohexyl)—CH₂— | —OCH₃ | " | —OCH₃ | —OCH₃ |
| O₂N—(cyclohexyl)—CH₂— | —OCH₃ | " | —OCH₃ | —OCH₃ |
| —(CH₂)₃—ONO₂ | —OCH₃ | " | —OCH₃ | —OCH₃ |

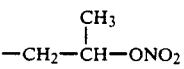

| Y | $R_2$ | $R_6$ | $R_4$ | $R_5$ |
|---|---|---|---|---|
| 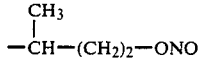 —CH$_2$—CH(CH$_3$)—ONO$_2$ | —OCH$_3$ | —CH(CH$_3$)$_2$ | —OCH$_3$ | —OCH$_3$ |
| —CH(CH$_3$)—(CH$_2$)$_2$—ONO$_2$ | —OCH$_3$ | " | —OCH$_3$ | —OCH$_3$ |
| —(CH$_2$)$_4$—ONO$_2$ | —OCH$_3$ | " | —OCH$_3$ | —OCH$_3$ |
| —(CH$_2$)$_3$—CH(CH$_3$)—ONO$_2$ | —OCH$_3$ | " | —OCH$_3$ | —OCH$_3$ |
| —CH$_2$—O—CH$_2$—CH$_2$—ONO$_2$ | —OCH$_3$ | " | —OCH$_3$ | —OCH$_3$ |
| —CH$_2$—S—CH$_2$—CH$_2$—ONO$_2$ | —OCH$_3$ | " | —OCH$_3$ | —OCH$_3$ |
| —CH(CH$_3$)—S—CH$_2$—CH$_2$—ONO$_2$ | —OCH$_3$ | " | —OCH$_3$ | —OCH$_3$ |
| 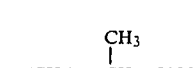 | —OCH$_3$ | " | —OCH$_3$ | —OCH$_3$ |
| 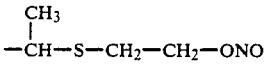 | —OCH$_3$ | " | —OCH$_3$ | —OCH$_3$ |
| —C(CH$_3$)$_2$—CH$_2$—ONO$_2$ | —OCH$_3$ | " | —OCH$_3$ | —OCH$_3$ |
|  | —OCH$_3$ | " | —OCH$_3$ | —OCH$_3$ |
|  | —OCH$_3$ | " | —OCH$_3$ | —OCH$_3$ |
| 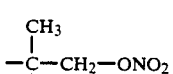 | —OCH$_3$ | " | —OCH$_3$ | —OCH$_3$ |
| —(CH$_2$)$_3$—ONO$_2$ | —OCH$_3$ | " | —OCH$_3$ | —OCH$_3$ |

| | | | | |
|---|---|---|---|---|
| | | Structure (verapamil-like core with O-CH₂-CH₂-NH-CO-Y substituent): $R_2$, CN, $R_6$, $(CH_2)_3$-N(CH$_3$)-$(CH_2)_2$-Ar($R_4$, $R_5$) | | |
| Y | $R_2$ | $R_6$ | $R_4$ | $R_5$ |
| -CH$_2$-CH(CH$_3$)-ONO$_2$ | -OCH$_3$ | -CH(CH$_3$)$_2$ | -OCH$_3$ | -OCH$_3$ |
| -CH(CH$_3$)-(CH$_2$)$_2$-ONO$_2$ | -OCH$_3$ | " | -OCH$_3$ | -OCH$_3$ |
| -(CH$_2$)$_4$-ONO$_2$ | -OCH$_3$ | " | -OCH$_3$ | -OCH$_3$ |
| -(CH$_2$)$_3$-CH(CH$_3$)-ONO$_2$ | -OCH$_3$ | " | -OCH$_3$ | -OCH$_3$ |
| -CH$_2$-O-CH$_2$-CH$_2$-ONO$_2$ | -OCH$_3$ | " | -OCH$_3$ | -OCH$_3$ |
| -CH$_2$-S-CH$_2$-CH$_2$-ONO$_2$ | -OCH$_3$ | " | -OCH$_3$ | -OCH$_3$ |
| -CH(CH$_3$)-S-CH$_2$-CH$_2$-ONO$_2$ | -OCH$_3$ | " | -OCH$_3$ | -OCH$_3$ |
| -CH$_2$-S-(cyclopentyl-ONO$_2$) | -OCH$_3$ | " | -OCH$_3$ | -OCH$_3$ |
| -CH$_2$-S-(cyclohexyl-ONO$_2$) | -OCH$_3$ | " | -OCH$_3$ | -OCH$_3$ |
| -C(CH$_3$)$_2$-CH$_2$-ONO$_2$ | -OCH$_3$ | " | -OCH$_3$ | -OCH$_3$ |
| -CH$_2$-(cyclohexyl-ONO$_2$) | -OCH$_3$ | " | -OCH$_3$ | -OCH$_3$ |
| O$_2$NO-(cyclohexyl)-CH$_2$- (cis) | -OCH$_3$ | " | -OCH$_3$ | -OCH$_3$ |
| O$_2$NO-(cyclohexyl)-CH$_2$- (trans) | -OCH$_3$ | " | -OCH$_3$ | -OCH$_3$ |
| -(CH$_2$)$_3$-ONO$_2$ | -OCH$_3$ | " | -OCH$_3$ | -OCH$_3$ |

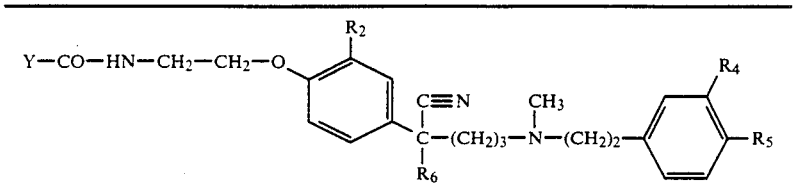

| Y | R₂ | R₆ | R₄ | R₅ |
|---|---|---|---|---|
| $-CH_2-\underset{\underset{CH_3}{\|}}{CH}-ONO_2$ | $-OCH_3$ | $-CH(CH_3)_2$ | $-OCH_3$ | $-OCH_3$ |
| $-\underset{\underset{CH_3}{\|}}{CH}-(CH_2)_2-ONO_2$ | $-OCH_3$ | " | $-OCH_3$ | $-OCH_3$ |
| $-(CH_2)_4-ONO_2$ | $-OCH_3$ | " | $-OCH_3$ | $-OCH_3$ |
| $-(CH_2)_3-\underset{\underset{CH_3}{\|}}{CH}-ONO_2$ | $-OCH_3$ | " | $-OCH_3$ | $-OCH_3$ |
| $-CH_2-O-CH_2-CH_2-ONO_2$ | $-OCH_3$ | " | $-OCH_3$ | $-OCH_3$ |
| $-CH_2-S-CH_2-CH_2-ONO_2$ | $-OCH_3$ | " | $-OCH_3$ | $-OCH_3$ |
| $-\underset{\underset{CH_3}{\|}}{CH}-S-CH_2-CH_2-ONO_2$ | $-OCH_3$ | " | $-OCH_3$ | $-OCH_3$ |
| $-CH_2-$ (cyclopentyl-S, with ONO₂) | $-OCH_3$ | " | $-OCH_3$ | $-OCH_3$ |
| $-CH_2-$ (cyclohexyl-S, with ONO₂) | $-OCH_3$ | " | $-OCH_3$ | $-OCH_3$ |
| $-\underset{\underset{CH_3}{\|}}{\overset{\overset{CH_3}{\|}}{C}}-CH_2-ONO_2$ | $-OCH_3$ | " | $-OCH_3$ | $-OCH_3$ |
| $-CH_2-$ (cyclohexyl with ONO₂) | $-OCH_3$ | " | $-OCH_3$ | $-OCH_3$ |
| $O_2NO-$ (cyclohexyl)$-CH_2-$ (cis) | $-OCH_3$ | " | $-OCH_3$ | $-OCH_3$ |
| $O_2NO-$ (cyclohexyl)$-CH_2-$ (trans) | $-OCH_3$ | " | $-OCH_3$ | $-OCH_3$ |
| $-(CH_2)_3-ONO_2$ | $-OCH_3$ | " | $-OCH_3$ | $-OCH_3$ |

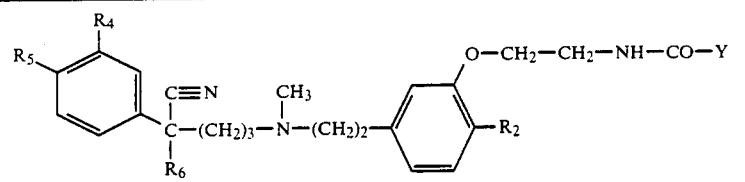

| Y | R₂ | R₆ | R₄ | R₅ |
|---|---|---|---|---|
| $-CH_2-\underset{\underset{CH_3}{\mid}}{CH}-ONO_2$ | —OCH₃ | —CH(CH₃)₂ | —OCH₃ | —OCH₃ |
| $-\underset{\underset{CH_3}{\mid}}{CH}-(CH_2)_2-ONO_2$ | —OCH₃ | " | —OCH₃ | —OCH₃ |
| $-(CH_2)_4-ONO_2$ | —OCH₃ | " | —OCH₃ | —OCH₃ |
| $-(CH_2)_3-\underset{\underset{CH_3}{\mid}}{CH}-ONO_2$ | —OCH₃ | " | —OCH₃ | —OCH₃ |
| $-CH_2-O-CH_2-CH_2-ONO_2$ | —OCH₃ | " | —OCH₃ | —OCH₃ |
| $-CH_2-S-CH_2-CH_2-ONO_2$ | —OCH₃ | " | —OCH₃ | —OCH₃ |
| $-\underset{\underset{CH_3}{\mid}}{CH}-S-CH_2-CH_2-ONO_2$ | —OCH₃ | " | —OCH₃ | —OCH₃ |
| $-CH_2-S-\text{(tetrahydrothiophene-ONO}_2\text{)}$ | —OCH₃ | " | —OCH₃ | —OCH₃ |
| $-CH_2-S-\text{(tetrahydrothiopyran-ONO}_2\text{)}$ | —OCH₃ | " | —OCH₃ | —OCH₃ |
| $-\underset{\underset{CH_3}{\mid}}{\overset{\overset{CH_3}{\mid}}{C}}-CH_2-ONO_2$ | —OCH₃ | " | —OCH₃ | —OCH₃ |
| $-CH_2-\text{(cyclohexyl-ONO}_2\text{)}$ | —OCH₃ | " | —OCH₃ | —OCH₃ |
| $O_2NO-\text{(cyclohexyl)}-CH_2-$ | —OCH₃ | " | —OCH₃ | —OCH₃ |
| $O_2NO-\text{(cyclohexyl)}-CH_2-$ | —OCH₃ | " | —OCH₃ | —OCH₃ |
| $-(CH_2)_3-ONO_2$ | —OCH₃ | " | —OCH₃ | —OCH₃ |

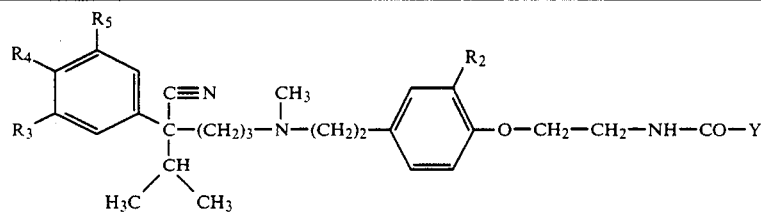

| Y | R₂ | R₃ | R₄ | R₅ |
|---|---|---|---|---|
| $-CH_2-CH(CH_3)-ONO_2$ | $-OCH_3$ | $-OCH_3$ | $-OCH_3$ | $-OCH_3$ |
| $-CH(CH_3)-(CH_2)_2-ONO_2$ | $-OCH_3$ | " | $-OCH_3$ | $-OCH_3$ |
| $-(CH_2)_4-ONO_2$ | $-OCH_3$ | " | $-OCH_3$ | $-OCH_3$ |
| $-(CH_2)_3-CH(CH_3)-ONO_2$ | $-OCH_3$ | " | $-OCH_3$ | $-OCH_3$ |
| $-CH_2-O-CH_2-CH_2-ONO_2$ | $-OCH_3$ | " | $-OCH_3$ | $-OCH_3$ |
| $-CH_2-S-CH_2-CH_2-ONO_2$ | $-OCH_3$ | " | $-OCH_3$ | $-OCH_3$ |
| $-CH(CH_3)-S-CH_2-CH_2-ONO_2$ | $-OCH_3$ | " | $-OCH_3$ | $-OCH_3$ |
| $-CH_2-S-$ (cyclopentyl-ONO₂) | $-OCH_3$ | " | $-OCH_3$ | $-OCH_3$ |
| $-CH_2-S-$ (cyclohexyl-ONO₂) | $-OCH_3$ | " | $-OCH_3$ | $-OCH_3$ |
| $-C(CH_3)_2-CH_2-ONO_2$ | $-OCH_3$ | " | $-OCH_3$ | $-OCH_3$ |
| $-CH_2-$ (cyclohexyl-ONO₂) | $-OCH_3$ | " | $-OCH_3$ | $-OCH_3$ |
| $O_2NO-$(cyclohexyl)$-CH_2-$ | $-OCH_3$ | " | $-OCH_3$ | $-OCH_3$ |
| $O_2NO-$(cyclohexyl)$-CH_2-$ | $-OCH_3$ | " | $-OCH_3$ | $-OCH_3$ |
| $-(CH_2)_3-ONO_2$ | $-OCH_3$ | " | $-OCH_3$ | $-OCH_3$ |

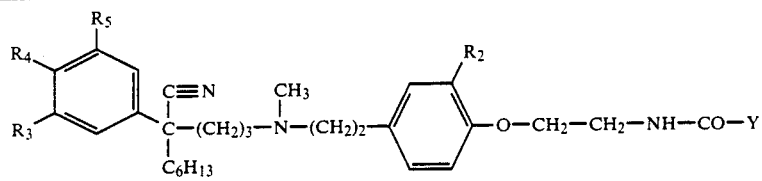

| Y | $R_2$ | $R_3$ | $R_4$ | $R_5$ |
|---|---|---|---|---|
| —CH₂—CH(CH₃)—ONO₂ | —OCH₃ | —OCH₃ | —OCH₃ | —OCH₃ |
| —CH(CH₃)—(CH₂)₂—ONO₂ | —OCH₃ | " | —OCH₃ | —OCH₃ |
| —(CH₂)₄—ONO₂ | —OCH₃ | " | —OCH₃ | —OCH₃ |
| —(CH₂)₃—CH(CH₃)—ONO₂ | —OCH₃ | " | —OCH₃ | —OCH₃ |
| —CH₂—O—CH₂—CH₂—ONO₂ | —OCH₃ | " | —OCH₃ | —OCH₃ |
| —CH₂—S—CH₂—CH₂—ONO₂ | —OCH₃ | " | —OCH₃ | —OCH₃ |
| —CH(CH₃)—S—CH₂—CH₂—ONO₂ | —OCH₃ | " | —OCH₃ | —OCH₃ |
| —CH₂—S—(cyclopentyl-ONO₂) | —OCH₃ | " | —OCH₃ | —OCH₃ |
| —CH₂—S—(cyclohexyl-ONO₂) | —OCH₃ | " | —OCH₃ | —OCH₃ |
| —C(CH₃)₂—CH₂—ONO₂ | —OCH₃ | " | —OCH₃ | —OCH₃ |
| —CH₂—(cyclohexyl-ONO₂) | —OCH₃ | " | —OCH₃ | —OCH₃ |
| (O₂NO-cyclohexyl)—CH₂— | —OCH₃ | " | —OCH₃ | —OCH₃ |
| (O₂NO-cyclohexyl)—CH₂— | —OCH₃ | " | —OCH₃ | —OCH₃ |
| —(CH₂)₃—ONO₂ | —OCH₃ | " | —OCH₃ | —OCH₃ |

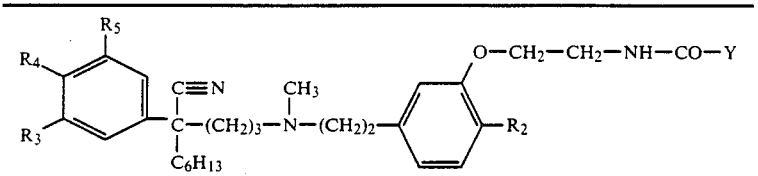

| Y | R₂ | R₃ | R₄ | R₅ |
|---|---|---|---|---|
| $-CH_2-\underset{\underset{CH_3}{\mid}}{CH}-ONO_2$ | $-OCH_3$ | $-OCH_3$ | $-OCH_3$ | $-OCH_3$ |
| $-\underset{\underset{CH_3}{\mid}}{CH}-(CH_2)_2-ONO_2$ | $-OCH_3$ | $-OCH_3$ | $-OCH_3$ | $-OCH_3$ |
| $-(CH_2)_4-ONO_2$ | $-OCH_3$ | $-OCH_3$ | $-OCH_3$ | $-OCH_3$ |
| $-(CH_2)_3-\underset{\underset{CH_3}{\mid}}{CH}-ONO_2$ | $-OCH_3$ | $-OCH_3$ | $-OCH_3$ | $-OCH_3$ |
| $-CH_2-O-CH_2-CH_2-ONO_2$ | $-OCH_3$ | $-OCH_3$ | $-OCH_3$ | $-OCH_3$ |
| $-CH_2-S-CH_2-CH_2-ONO_2$ | $-OCH_3$ | $-OCH_3$ | $-OCH_3$ | $-OCH_3$ |
| $-\underset{\underset{CH_3}{\mid}}{CH}-S-CH_2-CH_2-ONO_2$ | $-OCH_3$ | $-OCH_3$ | $-OCH_3$ | $-OCH_3$ |
| $-CH_2-S-$ cyclopentyl-$ONO_2$ | $-OCH_3$ | $-OCH_3$ | $-OCH_3$ | $-OCH_3$ |
| $-CH_2-S-$ cyclohexyl-$ONO_2$ | $-OCH_3$ | $-OCH_3$ | $-OCH_3$ | $-OCH_3$ |
| $-\underset{\underset{CH_3}{\mid}}{\overset{\overset{CH_3}{\mid}}{C}}-CH_2-ONO_2$ | $-OCH_3$ | $-OCH_3$ | $-OCH_3$ | $-OCH_3$ |
| $-CH_2-$cyclohexyl-$ONO_2$ | $-OCH_3$ | $-OCH_3$ | $-OCH_3$ | $-OCH_3$ |
| $O_2NO-$cyclohexyl-$CH_2-$ | $-OCH_3$ | $-OCH_3$ | $-OCH_3$ | $-OCH_3$ |
| $O_2NO-$cyclohexyl-$CH_2-$ | $-OCH_3$ | $-OCH_3$ | $-OCH_3$ | $-OCH_3$ |
| $-(CH_2)_3-ONO_2$ | $-OCH_3$ | $-OCH_3$ | $-OCH_3$ | $-OCH_3$ |

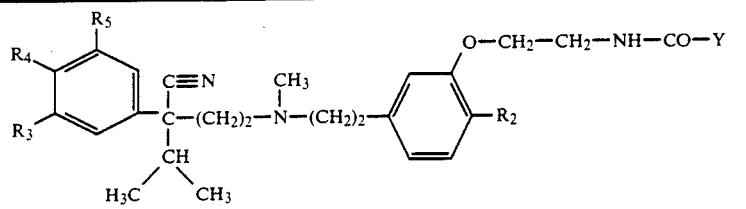

| Y | $R_2$ | $R_3$ | $R_4$ | $R_5$ |
|---|---|---|---|---|
| —CH$_2$—CH(CH$_3$)—ONO$_2$ | —OCH$_3$ | —OCH$_3$ | —OCH$_3$ | —OCH$_3$ |
| —CH(CH$_3$)—(CH$_2$)$_2$—ONO$_2$ | —OCH$_3$ | —OCH$_3$ | —OCH$_3$ | —OCH$_3$ |
| —(CH$_2$)$_4$—ONO$_2$ | —OCH$_3$ | —OCH$_3$ | —OCH$_3$ | —OCH$_3$ |
| —(CH$_2$)$_3$—CH(CH$_3$)—ONO$_2$ | —OCH$_3$ | —OCH$_3$ | —OCH$_3$ | —OCH$_3$ |
| —CH$_2$—O—CH$_2$—CH$_2$—ONO$_2$ | —OCH$_3$ | —OCH$_3$ | —OCH$_3$ | —OCH$_3$ |
| —CH$_2$—S—CH$_2$—CH$_2$—ONO$_2$ | —OCH$_3$ | —OCH$_3$ | —OCH$_3$ | —OCH$_3$ |
| —CH(CH$_3$)—S—CH$_2$—CH$_2$—ONO$_2$ | —OCH$_3$ | —OCH$_3$ | —OCH$_3$ | —OCH$_3$ |
| —CH$_2$—S—(cyclopentyl-ONO$_2$) | —OCH$_3$ | —OCH$_3$ | —OCH$_3$ | —OCH$_3$ |
| —CH$_2$—S—(cyclohexyl-ONO$_2$) | —OCH$_3$ | —OCH$_3$ | —OCH$_3$ | —OCH$_3$ |
| —C(CH$_3$)$_2$—CH$_2$—ONO$_2$ | —OCH$_3$ | —OCH$_3$ | —OCH$_3$ | —OCH$_3$ |
| —CH$_2$—(cyclohexyl-ONO$_2$) | —OCH$_3$ | —OCH$_3$ | —OCH$_3$ | —OCH$_3$ |
| O$_2$NO—(cyclohexyl)—CH$_2$— | —OCH$_3$ | —OCH$_3$ | —OCH$_3$ | —OCH$_3$ |
| O$_2$NO—(cyclohexyl)—CH$_2$— | —OCH$_3$ | —OCH$_3$ | —OCH$_3$ | —OCH$_3$ |
| —(CH$_2$)$_3$—ONO$_2$ | —OCH$_3$ | —OCH$_3$ | —OCH$_3$ | —OCH$_3$ |

The following Examples are given for tthe purpose of illustrating the present invention:

EXAMPLE 1

2-Methoxy-4-{1-cyano-1-(methylethyl)-4-[N-methyl-N-[2-(3,4-dimethoxyphenyl)-ethyl]-aminobutyl]}-phenoxy-N-(nitrooxyethyl)-acetamide oxalate dihydrate.

3 g. 2-Methoxy-4-{1-cyano-1-(methylethyl)-4-[N-methyl-N-[2-(3,4-dimethoxyphenyl)-ethyl]-aminobutyl}-phenoxyacetic acid are dissolved in a mixture of 60 ml. methylene chloride and 1.27 ml. triethylamine. A solution of 1 ml. ethyl chloroformate in 30 ml. methylene chloride is added dropwise thereto, while stirring, at −15° C. When the addition is finished, stirring is continued for 45 minutes at −15° C. and then 1.6 g. nitrooxyethylammonium nitrate is added thereto. Subsequently, while stirring at −15° C., a solution of 2.75 ml. triethylamine in 25 ml. methylene chloride is added dropwise thereto. The reaction mixture is further stirred for 30 minutes at −15° C., then diluted with 50 ml. methylene chloride and washed several times with water. The methylene chloride phase is dried over anhydrous sodium sulphate and evaporated.

For further purification, the residue is chromatographed on a silica gel column (220 g. silica gel 60; elution agent: methylene chloride/4% methanol). The column fractions obtained are evaporated, the residue is dissolved in methanol and the solution is mixed with a methanolic solution of 0.8 g. oxalic acid dihydrate. The solution is evaporated and the residue is treated with diisopropyl ether. There are obtained 3.75 g. (87% of theory) of the title compound in the form of crystals; m.p. 124°–125° C. (decomp.).

The following are prepared in an analogous manner:

EXAMPLE 2

2-Methoxy-4-{1-cyano-1-(methylethyl)-4-[N-methyl-N-[2-(3,4-dimethoxyphenyl)-ethyl]-aminobutyl]}-phenoxy-N-(2-nitrooxypropyl)-acetamide oxalate; m.p. 115°–116° C. (decomp.).

EXAMPLE 3

2-Methoxy-4-{1-cyano-1-(methylethyl)-4-[N-methyl-N-[2-(3,4-dimethoxyphenyl)-ethyl]-aminobutyl]}-phenoxy-N-(3-nitrooxybutyl-2)-acetamide oxalate; m.p. 136°–137° C. (decomp.).

EXAMPLE 4

2-Methoxy-4-{1-cyano-1-(methylethyl)-4-[N-methyl-N-[2-(3,4-dimethoxyphenyl)-ethyl]-aminobutyl]}-phenoxy-N-(2-methyl-3-nitrooxypropyl-2)-acetamide

EXAMPLE 5

2-Methoxy-4-{1-cyano-1-(methylethyl)-4-[N-methyl-N-[2-(3,4-dimethoxyphenyl)-ethyl]-aminobutyl]}-phenoxy-N-(1,3-bis-nitrooxycyclohexyl-2)-acetamide

EXAMPLE 6

2-Methoxy-4-{1-cyano-1-(methylethyl)-4-[N-methyl-N-[2-(3,4-dimethoxyphenyl)-ethyl]-aminobutyl]}-phenoxy-N,N-bis-(nitrooxyethyl)-acetamide oxalate dihydrate; m.p. 105°–107° C. (decomp.).

EXAMPLE 7

2-Methoxy-4-{1-cyano-1-(methylethyl)-4-[N-methyl-N-[2-(3,4-dimethoxyphenyl)-ethyl]-aminobutyl]}-phenoxy-N,N-bis-(2-nitrooxypropyl)-acetamide oxalate hydrate; m.p. 118°–120° C. (decomp.).

The 2-methoxy-4-{1-cyano-1-(methylethyl)-4-[N-methyl-N-[2-(3,4-dimethoxyphenyl)-ethyl]-aminobutyl]}-phenoxy acetic acid required as starting material is prepared as follows:

Step 1: 3-Methoxy-4-benzyloxy-α-isopropylbenzyl cyanide 150 g. 3-Methoxy-4-benzyloxybenzyl cyanide, together with 470 ml. 50% aqueous sodium hydroxide solution, 76 ml. 2-bromopropane and 6 g. benzyltributylammonium bromide are stirred for 5 hours at 55° C. The reaction mixture is then poured into 4 liters of water and extracted several times with methylene chloride. The combined methylene chloride phases are dried over anhydrous sodium sulphate, evaporated and the residue distilled in a high vacuum.

There are obtained 155 g. (90% of theory) 3-methoxy-4-benzyloxy-α-isopropylbenzyl cyanide; b.p. 184°–186° C./6.10$^{-2}$ mm; m.p. 68°–70° C.

Step 2: α-Isopropyl-α-[(N-methyl-N-homoveratryl)-amino-γ-propyl]-3-methoxy-4-benzyloxyphenylacetonitrile 36.6 g. 3-Methoxy-4-benzyloxy-α-isopropylbenzyl cyanide are dissolved in 150 ml. anhydrous dimethylformamide. 30.3 g. (N-methyl-N-homoveratryl)-amine-γ-chloropropane are added thereto and the mixture is warmed to 50° C. In the course of 1 hour, 5.7 g. 55% sodium hydride are added thereto, while stirring. After completion of the addition, stirring is continued for a further 2 hours at 50° C. and the reaction mixture is then poured into 4 liters of water. This is then extracted several times with methylene chloride and the combined methylene chloride phases are dried over anhydrous sodium sulphate and evaporated to dryness. For purification, the residue is chromatographed on a silica gel column (1.2 kg. silica gel; elution agent: methylene chloride/2% methanol). After evaporation of the column fractions, there are obtained 45 g. (70% of theory) α-isopropyl-α-[(N-methyl-N-homoveratryl)-amino-γ-propyl]-3-methoxy-4-benzyloxyphenylacetonitrile as an oily product.

Step 3: α-Isopropyl-α-[(N-methyl-N-homoveratryl)-amino-γ-propyl]-3-methoxy-4-hydroxyphenylacetonitrile 45 g. α-Isopropyl-α-[(N-methyl-N-homoveratryl)-amino-γ-propyl]-3-methoxy-4-benzyloxy-phenylacetonitrile are dissolved in 400 ml. methanol and, after the addition of 4 g. Pd/C (10%) catalyst, hydrogenated. After the take up of the calculated amount of hydrogen, the catalyst is filtered off and the filtrate evaporated. There are obtained 36 g. (97% of theory) α-isopropyl-α-[(N-methyl-N-homoveratryl)-amino-γ-propyl]-3-methoxy-4-hydroxyphenylacetonitrile in the form of an oily product.

Step 4: Ethyl 2-methoxy-4-{1-cyano-1-(methylethyl)-4-[N-methyl-N-[2-(3,4-dimethoxyphenyl)-ethyl]-aminobutyl]}-phenoxyacetate 34.5 g. α-Isopropyl-α-[(N-methyl-N-homoveratryl)-amino-γ-propyl]-3-methoxy-4-hydroxyphenylacetonitrile are dissolved in 200 ml. dimethylformamide and mixed, while stirring at ambient temperature, with 3.5 g. sodium hydride (55%). Stirring is continued for 15 minutes and then a solution of 9.8 ml. ethyl bromoacetate in 50 ml. dimethylformamide is added dropwise thereto. The temperature is hereby not to exceed 30° C. After completion of the addition, stirring is continued for 1 hour, the reaction mixture is poured into 4 liters of water and extracted several times with methylene chloride. The combined methylene chloride phases are dried over anhydrous sodium sulphate and then evaporated. For purification, the residue is chromatographed on a silica gel column (1.2 kg. silica gel; elution agent: methylene chloride/3% methanol). After evaporation of the column fractions, there are obtained 33.3 g. (81% of theory) ethyl 2-methoxy-4-{1-cyano-1-(methylethyl)-4-[N-methyl-N-[2-(3,4-dimethoxyphenyl)-ethyl]-aminobutyl]}-phenoxyacetate in the form of an oily product.

Step 5:
2-Methoxy-4-{1-cyano-1-(methylethyl)-4-[N-methyl-N-[2-(3,4-dimethoxyphenyl)-ethyl]-aminobutyl]}-phenoxyacetic acid Ethyl 2-methoxy-4-<1-cyano-1-(methylethyl)-4-[N-methyl-N-[2-(3,4-dimethoxyphenyl)-ethyl]-aminobutyl]>-phenoxyacetate are dissolved in 150 ml. ethanol. 125 ml. 1N aqueous sodium hydroxide solution are added dropwise thereto at ambient temperature, while stirring. After completion of the addition, stirring is continued for 1 hour at ambient temperature and the alcohol then evaporated off. 125 ml. 1N hydrochloric acid are then added thereto, followed by extracting several times with methylene chloride. The combined methylene chloride phases are dried over anhydrous sodium sulphate and evaporated. There are obtained 29.5 g. (94% of theory) 2-methoxy-4-{1-cyano-1-(methylethyl)-4-[N-methyl-N-[2-(3,4-dimethoxyphenyl)-ethyl]aminobutyl]}-phenoxyacetic acid as an oily product.

EXAMPLE 8

2-Methoxy-5-{1-cyano-1-(methylethyl)-4-[N-methyl-N-[2-(3,4-dimethoxyphenyl)-ethyl]-aminobutyl]}-phenoxy-N-(nitrooxyethyl)-acetamide oxalate hydrate 4.5 g. 2-Methoxy-5-{1-cyano-1-(methylethyl)-4-[N-methyl-N-[2-(3,4-dimethoxyphenyl)-ethyl]-aminobutyl]}-phenoxyacetic acid are dissolved in a mixture of 80 ml. methylene chloride and 1.9 ml. triethylamine. A solution of 1.35 ml. ethyl chloroformate in 30 ml. methylene chloride is added dropwise thereto at −15° C., while stirring. After completion of the addition, stirring is continued at −15° C. for a further 45 minutes and then 2.3 g. nitrooxyethylammonium nitrate are added thereto. Subsequently, a solution of 3.8 ml. triethylamine in 25 ml. methylene chloride is added dropwise thereto at −15° C., while stirring and the reaction solution is diluted with 50 ml. methylene chloride and washed several times with water. The methylene chloride phase is dried over anhydrous sodium sulphate and evaporated. For purification, the residue is chromatographed on a silica gel column (250 g. silica gel; elution agent: methylene chloride/3% methanol). The column fractions obtained are evaporated, the residue is dissolved in methanol and the solution is mixed with a methanolic solution of 1.25 g. oxalic acid dihydrate. The solution is evaporated and the residue treated with diisopropyl ether. There are obtained 4.9 g. (78% of theory) of the title compound in the form of crystals; m.p. 127°–129° C. (decomp.).

The following are prepared in an analogous manner:

EXAMPLE 9

2-Methoxy-5-{1-cyano-1-(methylethyl)-4-[N-methyl-N-[2-(3,4-dimethoxyphenyl)-ethyl]-aminobutyl]}-phenoxy-N-(2-nitrooxypropyl)-acetamide oxalate hydrate; m.p. 132°–134° C. (decomp.).

EXAMPLE 10

2-Methoxy-5-{1-cyano-1-(methylethyl)-4-[N-methyl-N-[2-(3,4-dimethoxyphenyl)-ethyl]-aminobutyl]}-phenoxy-N-(3-nitrooxybutyl-2)-acetamide oxalate dihydrate; m.p. 123°–125° C. (decomp.).

EXAMPLE 11

2-Methoxy-5-{1-cyano-1-(methylethyl)-4-[N-methyl-N-[2-(3,4-dimethoxyphenyl)-ethyl]-aminobutyl]}-phenoxy-N-(2-methyl-3-nitrooxypropyl-2)-acetamide oxalate hydrate; m.p. 125°–127° C. (decomp.).

EXAMPLE 12

2-Methoxy-5-{1-cyano-1-(methylethyl)-4-[N-methyl-N-[2-(3,4-dimethoxyphenyl)-ethyl]-aminobutyl]}-phenoxy-N-(1,3-bis-nitrooxycyclohexyl-2)-acetamide oxalate hydrate; m.p. 140°–142° C. (decomp.).

EXAMPLE 13

2-Methoxy-5-{1-cyano-1-(methylethyl)-4-[N-methyl-N-[2-(3,4-dimethoxyphenyl)-ethyl]-aminobutyl]}-phenoxy-N,N-bis-(nitrooxyethyl)-acetamide oxalate hydrate; m.p. 105°–107° C. (decomp.).

EXAMPLE 14

2-Methoxy-5-{1-cyano-1-(methylethyl)-4-[N-methyl-N-[2-(3,4-dimethoxyphenyl)-ethyl]-aminobutyl]}-phenoxy-N,N-bis-(2-nitroxypropyl)-acetamide oxalate hydrate; m.p. 118°–120° C. (decomp.). (reaction with 2-nitrooxypropylammonium-nitrate).

The 2-methoxy-5-{1-cyano-1-(methylethyl)-4-[N-methyl-N-[2-(3,4-dimethoxyphenyl)-ethyl]-aminobutyl]}-phenoxyacetic acid required as starting material is prepared analogously to 2-methoxy-4-{1-cyano-1-(methylethyl)-4-[N-methyl-N-[2-(3,4-dimethoxyphenyl)-ethyl]-aminobutyl]}-phenoxyacetic acid except that, instead of 3-methoxy-4-benzyloxybenzyl cyanide, 3-benzyloxy-4-methoxybenzyl cyanide is used as starting material.

EXAMPLE 15

2-Methoxy-4-{2-[N-methyl-N-[4-cyano-4-(methylethyl)-4-(3,4-dimethoxyphenyl)-butyl]-aminoethyl]}-phenoxy-N-(nitrooxyethyl)-acetamide oxalate hydrate.

3 g. 2-Methoxy-4-{2-[N-methyl-N-(4-cyano-4-(methylethyl)-4-(3,4-dimethoxyphenyl)-butyl]-aminoethyl]}-phenoxyacetic acid are dissolved in a mixture of 60 ml. methylene chloride and 1.3 ml. triethylamine. A solution of 1 ml. ethyl chloroformate in 30 ml. methylene chloride is added dropwise thereto at −15° C., while stirring. After completion of the addition, stirring is continued for 45 minutes at −15° C., 1.6 g. nitrooxyethylammonium nitrate is added thereto and a solution of 2.9 ml. triethylamine in 30 ml. methylene chloride is then added dropwise thereto. Stirring is continued for 30 minutes at −15° C. and the reaction solution is diluted with 50 ml. methylene chloride and washed several times with water. The methylene chloride phase is dried over anhydrous sodium sulphate and evaporated. For further purification, the residue is chromatographed on a silica gel column (220 g. silica gel; elution agent: methanol/4% methylene chloride). The column fractions obtained are evaporated, the residue is dissolved in methanol and the solution is mixed with a methanolic solution of 850 mg. oxalic acid dihydrate. The solution is evaporated and the residue treated with diisopropyl ether. There are obtained 3.7 g. (85% of theory) of the title compound in the form of crystals; m.p. 132° C. (decomp.).

The following are prepared analogously:

EXAMPLE 16

2-Methoxy-4-{2-[N-methyl-N-[4-cyano-4-(methylethyl)-4-(3,4-dimethoxyphenyl)-butyl]-aminoethyl]}-phenoxy-N-(2-nitrooxypropyl)-acetamide oxalate hydrate; m.p. 135°–136° C. (decomp.).

EXAMPLE 17

2-Methoxy-4-{2-[N-methyl-N-[4-cyano-4-(methylethyl)-4-(3,4-dimethoxyphenyl)-butyl]-aminoethyl]}-phenoxy-N-(3-nitrooxybutyl-2)-acetamide oxalate hydrate; m.p. 132°–134° C. (decomp.).

EXAMPLE 18

2-Methoxy-4-{2-[N-methyl-N-[4-cyano-4-(methylethyl)-4-(3,4-dimethoxyphenyl)-butyl]-aminoethyl]}-phenoxy-N-(2-methyl-3-nitrooxypropyl-2)-acetamide oxalate hydrate; m.p. 122°–124° C. (decomp.).

EXAMPLE 19

2-Methoxy-4-{2-[N-methyl-N-[4-cyano-4-(methylethyl)-4-(3,4-dimethoxyphenyl)-butyl]-aminoethyl]}-phenoxy-N-(1,3-bis-nitrooxycyclohexyl-2)-acetamide oxalate; m.p. 90°–92° C. (decomp.).

EXAMPLE 20

2-Methoxy-4-{2-[N-methyl-N-[4-cyano-4-(methylethyl)-4-(3,4-dimethoxyphenyl)-butyl]-aminoethyl]}-phenoxy-N,N-bis-(nitrooxyethyl)-acetamide oxalate hydrate; m.p. 110°–112° C. (decomp.).

EXAMPLE 21

2-Methoxy-4-{2-[N-methyl-N-[4-cyano-4-(methylethyl)-4-(3,4-dimethoxyphenyl)-butyl]-aminoethyl]}-phenoxy-N,N-bis-(2-nitrooxypropyl)-acetamide oxalate dihydrate; m.p. 110°–112° C. (decomp.).

EXAMPLE 22

2-Methoxy-4-{2-[N-methyl-N-[4-cyano-4-(methylethyl)-4-(3,4,5-trimethoxyphenyl)-butyl]-aminoethyl]}-phenoxy-N-(nitrooxyethyl)-acetamide oxalate dihydrate; m.p. 128°–130° C. (decomp.).

EXAMPLE 23

2-Methoxy-4-{2-[N-methyl-N-[4-cyano-4-(methylethyl)-4-(3,4,5-trimethoxyphenyl)-butyl]-aminoethyl]}-phenoxy-N-(2-nitrooxypropyl)-acetamide oxalate dihydrate; m.p. 135°–136° C. (decomp.).

EXAMPLE 24

2-Methoxy-4-{2-[N-methyl-N-[4-cyano-4-(methylethyl)-4-(3,4,5-trimethoxyphenyl)-butyl]-aminoethyl]}-phenoxy-N-(3-nitrooxybutyl-2)-acetamide oxalate dihydrate; m.p. 123°–124° C. (decomp.).

EXAMPLE 25

2-Methoxy-4-{2-[N-methyl-N-[4-cyano-4-(methylethyl)-4-(3,4,5-trimethoxyphenyl)-butyl]-aminoethyl]}-phenoxy-N-(1,3-bis-nitrooxycyclohexyl-2)-acetamide oxalate; m.p. 147°–149° C.

The 2-methoxy-4-{2-[N-methyl-N-[4-cyano-4-(methylethyl)-4-(3,4-dimethoxyphenyl)-butyl]-aminoethyl]}-phenoxyacetic acid required as starting material is prepared as follows:

Step 1:
α-Isopropyl-α-{[N-methyl-N-[2-(3-methoxy-4-benzyloxy)-ethyl]]-amino-γ-propyl}-3,4-dimethoxyphenylacetonitrile 48.5 g. α-Isopropyl-3,4-dimethoxyphenylacetonitrile are dissolved in 200 ml. dimethylformamide. 40.8 g. N-methyl-N-[2-(3-methoxy-4-benzyloxy)-ethyl]-N-(γ-chloropropyl)-amine are added thereto and the solution is warmed to 50° C. In the course of 1 hour, 8.15 g. sodium hydride (55%) are added thereto. After completion of the addition, stirring is continued for 3 hours at 50° C. and the reaction mixture is poured into 4 liters of water and extracted several times with methylene chloride. The combined methylene chloride phases are washed with water, dried over anhydrous sodium sulphate and evaporated. For purification, the residue is chromatographed on a silica gel column (1.8 kg. silica gel; elution agent: methylene chloride/3% methanol). After evaporation of the column fractions, there are obtained 52.8 g. (86% of theory) of α-isopropyl-α-{[N-methyl-N-[2-(3-methoxy-4-benzyloxy)-ethyl]]-amino-γ-propyl}-3,4-dimethoxyphenylacetonitrile in the form of an oily product.

Step 2:
α-Isopropyl-α-{[N-methyl-N-[2-(3-methoxy-4-hydroxyphenyl)-ethyl]]-amino-γ-propyl}-3,4-dimethoxyphenylacetonitrile 47.9 g. α-Isopropyl-α-{[N-methyl-N-[2-(3-methoxy-4-benzyloxy)-ethyl]]-amino-γ-propyl}-3,4-dimethoxyphenylacetonitrile are dissolved in 400 ml. methanol and, after the addition of 2 g. Pd/C (10%) catalyst, hydrogenated. After the take up of the calculated amount of hydrogen, the catalyst is filtered off and the filrate evaporated. There are obtained 38 g. (95% of theory) α-isopropyl-α-{[N-methyl-N-[2-(3-methoxy-4-hydroxy)-ethyl]]-amino-γ-propyl}-3,4-dimethoxyphenylacetonitrile in the form of an oily product.

Step 3: Ethyl 2-methoxy-4-{2-[N-methyl-N-[4-cyano-4-(methylethyl)-4-(3,4-dimethoxyphenyl)-butyl]-aminoethyl]}-phenoxyacetate 37.7 g. α-Isopropyl-α-{[N-methyl-N-[2-(3-methoxy-4-hydroxy)-ethyl]]-amino-γ-propyl}-3,4-dimethoxyacetonitrile are dissolved in 200 ml. anhydrous dimethylformamide and mixed, while stirring, with 3.7 g. sodium hydride (55%). Stirring is continued for 15 minutes and then a solution of 10.7 g. ethyl bromoacetate in 100 ml. dimethylformamide is added dropwise thereto. The temperature should hereby not exceed 30° C. After completion of the addition, stirring is continued for 1 hour and the reaction mixture is then poured into 4 liters of water and extracted several times with methylene chloride. The combined methylene chloride phases are washed with water, dried over anhydrous sodium sulphate and evaporated. The residue is purified by chromatographing on a silica gel column. (1.2 kg. silica gel; elution agent: methylene chloride/3% methanol). After evaporation of the column fractions, there are obtained 36.6 g. (81% of theory) ethyl 2-methoxy-4-{2-

[N-methyl-N-[4-cyano-4-(methylethyl)-4-(3,4-dimethoxyphenyl)-butyl]-aminoethyl]}-phenoxyacetate in the form of an oily product.

Step 4:
2-Methoxy-4-{2-[N-methyl-N-[4-cyano-4-(methylethyl)-4-(3,4-dimethoxyphenyl)-butyl]-aminoethyl]}-phenoxyacetic acid 36.5 g. Ethyl 2-methoxy-4-{2-[N-methyl-N-[4-cyano-4-(methylethyl)-4-(3,4-dimethoxyphenyl)-butyl]-aminoethyl]}-phenoxyacetate are dissolved in 150 ml. ethanol. 140 ml. 1N aqueous sodium hydroxide solution are added thereto dropwise at ambient temperature, while stirring. Stirring is continued for 1 hour, then 140 ml. 1N hydrochloric acid are added thereto and the alcohol is evaporated off. The aqueous phase is extracted with methylene chloride. The methylene chloride phase is dried over anhydrous sodium sulphate and evaporated. There are obtained 33.7 g. (97% of theory) 2-methoxy-4-{2-[N-methyl-N-[4-cyano-4-(methylethyl)-4-(3,4-dimethoxyphenyl)-butyl]-aminoethyl]}-phenoxyacetic acid in the form of an oily product.

The N-methyl-N-[2-(3-methoxy-4-benzyloxy)-ethyl]N-(γ-chloropropyl)-amine used as starting material in Step 1 is prepared as follows:

148 g. 3-Methoxy-4-benzyloxybenzyl cyanide are dissolved in 2.5 liters of methanol and, after the addition of 350 ml. liquid ammonia and 16 g. Raney nickel, hydrogenated at 100° C. and 80 ats. pressure. The hydrogenation is finished after 4 hours. The catalyst is filtered off, the filtrate is evaporated and the residue is purified chromatographically on a silica gel column (1.6 kg. silica gel; elution agent: methylene chloride/5% isopropylamine). After evaporation of the column fractions, there are obtained 126 g. (84% of theory) 3-methoxy-4-benzyloxy-β-phenylethylamine. This is dissolved in 500 ml. toluene and, after the addition of 48.5 ml. benzaldehyde, heated under a water separator. After completion of the separation of water, the reaction mixture is allowed to cool to ambient temperature and 46 ml. dimethylformamide are added thereto. Subsequently, it is heated under reflux for 30 minutes and then cooled to ambient temperature, two layers thereby being formed. The upper toluene layer is separated off and discarded. The lower layer is mixed with 500 ml. 80% ethanol and subsequently heated under reflux for 30 minutes. The alcohol is then distilled off and the residue taken up in methylene chloride. The methylene chloride phase is extracted with concentrated hydrochloric acid and then discarded.

The aqueous phase is rendered alkaline with a concentrated aqueous solution of sodium hydroxide, while cooling, an oil thereby separating out. This is taken up in methylene chloride and the methylene chloride phase is dried over anhydrous sodium sulphate and evaporated. There are obtained 106 g. (80% of theory) 3-methoxy-4-benzyloxy-β-phenyl-N-methylethylamine in the form of an oily product. This is dissolved in 500 ml. dimethylformamide and, after the addition of 132 g. of potash and 52 ml. 1-bromo-3-chloropropane, stirred for 5 hours at ambient temperature. The reaction mixture is diluted with methylene chloride and the insoluble residue filtered off with suction. The filtrate is diluted with water and extracted several times with methylene chloride. The methylene chloride phases are combined, dried over anhydrous sodium sulphate and evaporated. For purification, the residue is chromatographed on a silica gel column (1.2 kg. silica gel; elution agent: methylene chloride/3% methanol). After evaporation of the column fractions, there are obtained 48.5 g. (36% of theory) N-methyl-N-[2-(3-methoxy-4-benzyloxy)-ethyl]-N-(γ-chloropropyl)-amine in the form of an oily product.

EXAMPLE 26

2-Methoxy-5-{2-[N-methyl-N-[4-cyano-4-(methylethyl)-4-(3,4-dimethoxyphenyl)-butyl]-aminoethyl]}-phenoxy-N-(nitrooxyethyl)-acetamide oxalate 4.5 g. 2-Methoxy-5-{2-[N-methyl-N-[4-cyano-4-(methylethyl)-4-(3,4-dimethoxyphenyl)-butyl]-aminoethyl]}-phenoxyacetic acid are dissolved in a mixture of 80 ml. methylene chloride and 1.9 ml. triethylamine. A solution of 1.4 ml. ethyl chloroformate in 30 ml. methylene chloride is added dropwise thereto at −15° C., while stirring. After completion of the addition, stirring is continued for 45 minutes at −15° C., 2.3 g. nitrooxyethylammonium nitrate are added thereto and then a solution of 3.8 ml. triethylamine in 30 ml. anhydrous methylene chloride is added dropwise thereto. Stirring is continued for 30 minutes at −15° C. and the reaction solution is diluted with 50 ml. methylene chloride and washed several times with water. The methylene chloride phase is dried over anhydrous sodium sulphate and evaporated. For further purification, the residue is chromatographed over a silica gel column (220 g. silica gel; elution agent: methylene chloride/3% methanol). The column fractions are evaporated, the residue is dissolved in methanol and the solution is mixed with a methanolic solution of 1.2 g. oxalic acid dihydrate. The solution is evaporated and the residue treated with diisopropyl ether. There are obtained 4.5 g. (74% of theory) of the title compound in the form of crystals; m.p. 128°–130° C. (decomp.).

The following are prepared analogously:

EXAMPLE 27

2-Methoxy-5-{2-[N-methyl-N-[4-cyano-4-(methylethyl)-4-(3,4-dimethoxyphenyl)-butyl]-aminoethyl]}-phenoxy-N-(2-nitrooxypropyl)-acetamide oxalate hydrate; m.p. 133°–135° C. (decomp.).

EXAMPLE 28

2-Methoxy-5-{2-[N-methyl-N-[4-cyano-4-(methylethyl)-4-(3,4-dimethoxyphenyl)-butyl]-aminoethyl]}-phenoxy-N-(3-nitrooxybutyl-2)-acetamide oxalate dihydrate; m.p. 123°–125° C.

EXAMPLE 29

2-Methoxy-5-{2-[N-methyl-N-[4-cyano-4-(methylethyl)-4-(3,4-dimethoxyphenyl)-butyl]-aminoethyl]}-phenoxy-N-(2-methyl-3-nitrooxypropyl-2)-acetamide oxalate hydrate; m.p. 128°–130° C. (decomp.).

EXAMPLE 30

2-Methoxy-5-{2-[N-methyl-N-[4-cyano-4-(methylethyl)-4-(3,4-dimethoxyphenyl)-butyl]-aminoethyl]}-phenoxy-N-(1,3-bis-nitrooxycyclohexyl-2)-acetamide oxalate hydrate; m.p. 143°–145° C. (decomp.).

EXAMPLE 31

2-Methoxy-5-{2-[N-methyl-N-[4-cyano-4-(methylethyl)-4-(3,4-dimethoxyphenyl)-butyl]-aminoethyl]}-phenoxy-N,N-bis-(nitrooxyethyl)-acetamide oxalate hydrate; m.p. 110°–112° C. (decomp.).

EXAMPLE 32

2-Methoxy-5-{2-[N-methyl-N-[4-cyano-4-(methylethyl)-4-(3,4-dimethoxyphenyl)-butyl]-aminoethyl]}-phenoxy-N,N-bis-(2-nitrooxypropyl)-acetamide oxalate hydrate; m.p. 118°-120° C. (decomp.).

The 2-methoxy-5-{2-[N-methyl-N-[4-cyano-4-(methylethyl)-4-(3,4-dimethoxyphenyl)-butyl]-aminoethyl]}-phenoxy acetic acid required as starting material was prepared analogously to 2-methoxy-4-{2-[N-methyl-N-[4-cyano-4-(methylethyl)-4-(3,4-dimethoxyphenyl)-butyl]-aminoethyl]}-phenoxyacetic acid.

The following are prepared analogously:

EXAMPLE 33

3-{2-[N-Methyl-N-[4-cyano-4-dodecyl-4-(3,4-dimethoxyphenyl)-butyl]-aminoethyl]}-phenoxy-N-(nitrooxyethyl)-acetamide oxalate; m.p. 134°-136° C. (decomp.).

EXAMPLE 34

3-{2-[N-Methyl-N-[4-cyano-4-dodecyl-4-(3,4-dimethoxyphenyl)-butyl]-aminoethyl]}-phenoxy-N-(2-nitrooxypropyl)acetamide oxalate hydrate; m.p. 140°-142° C. (decomp.).

EXAMPLE 35

3-{2-[N-Methyl-N-[4-cyano-4-dodecyl-4-(3,4,5-trimethoxyphenyl)-butyl]-aminoethyl]}-phenoxy-N-(2-nitrooxyethyl)-acetamide oxalate hydrate; m.p. 127°-129° C. (decomp.).

EXAMPLE 36

3-{1-Cyano-1-hexyl-4-[N-methyl-N-[2-(3-methoxyphenyl)-ethyl]-aminobutyl]}-phenoxy-N-(2-nitrooxypropyl)-acetamide oxalate; m.p. 134°-136° C.

EXAMPLE 37

3-{1-Cyano-1-hexyl-4-[N-methyl-N-[2-(3-methoxyphenyl)-ethyl]-aminobutyl]}-phenoxy-N-(nitrooxyethyl)-acetamide oxalate; oily.

EXAMPLE 38

2-Methoxy-5-{1-cyano-1-(methylethyl)-4-[N-methyl-N-[2-(3,4-dimethoxyphenyl)-ethyl]-aminobutyl]}-phenoxy-N-(2,2-dimethyl-3-nitrooxypropyl-1)-acetamide oxalate dihydrate; m.p. 140° C. (decomp.).

EXAMPLE 39

2-Methoxy-5-{2-[N-methyl-N-[4-cyano-4-(methylethyl)-4-(3,4-dimethoxyphenyl)-butyl]-aminoethyl]}-phenoxy-N-(2,2-dimethyl-3-nitrooxypropyl-1)-acetamide oxalate dihydrate; m.p. 140° C. (decomp.).

EXAMPLE 40

2-Methoxy-4-{1-cyano-1-(methylethyl)-4-[N-methyl-N-[2-(3,4-dimethoxyphenyl)-ethyl]-aminobutyl]}-phenoxy-N-(2,2-dimethyl-3-nitrooxypropyl-1)-acetamide oxalate dihydrate; m.p. 140° C. (decomp.).

EXAMPLE 41

2-Methoxy-5-{2-[N-methyl-N-[4-cyano-4-(methylethyl)-4-(3,4-dimethoxyphenyl)-butyl]-aminoethyl]}-phenoxy-N-(3-nitrooxypropyl-1)-acetamide oxalate dihydrate; m.p. 132°-135° C. (decomp.).

EXAMPLE 42

2-Methoxy-5-{2-[N-methyl-N-[4-cyano-4-(methylethyl)-4-(3,4-dimethoxyphenyl)-butyl]-aminoethyl]}-phenoxyacetic acid 4-(α-nitrooxyethyl)-piperidylamide citrate hydrate; m.p. 142°-145° C. (decomp.).

EXAMPLE 43

2-Methoxy-5-{2-[N-methyl-N-[4-cyano-4-(methylethyl)-4-(3,4-dimethoxyphenyl)-butyl]-aminoethyl]}-phenoxyacetic acid 4-nitrooxymethyl)-piperidylamide citrate hydrate; m.p. 146°-147° C. (decomp.).

EXAMPLE 44

2-Methoxy-4-{2-[N-methyl-N-[4-cyano-4-(methylethyl)-4-(3,4-dimethoxyphenyl)-butyl]-aminoethyl]}-phenoxyacetic acid 4-(nitrooxymethyl)-piperidylamide citrate hydrate; m.p. 144°-146° C. (decomp.).

EXAMPLE 45

2-Methoxy-4-{2-[N-methyl-N-[4-cyano-4-(methylethyl)-4-(3,4-dimethoxyphenyl)-butyl]-aminoethyl]}-phenoxyacetic acid 4-(α-nitrooxyethyl)-piperidylamide citrate hydrate; m.p. 143°-144° C. (decomp.).

EXAMPLE 46

2-Methoxy-5-{1-cyano-1-(methylethyl)-4-[N-methyl-N-[2-(3,4-dimethoxyphenyl)-ethyl]-aminobutyl]}-phenoxyacetic acid 4-(nitrooxymethyl)-piperidylamide citrate hydrate; m.p. 142°-145° C. (decomp.).

EXAMPLE 47

2-Methoxy-5-{1-cyano-1-(methylethyl)-4-[N-methyl-N-[2-(3,4-dimethoxyphenyl)-ethyl]-aminobutyl]}-phenoxyacetic acid 4-(α-nitrooxyethyl)-piperidylamide citrate hydrate; m.p. 144°-146° C. (decomp.).

EXAMPLE 48

2-Methoxy-5-{2-[N-methyl-N-[4-cyano-4-(methylethyl)-4-(3,4,5-trimethoxyphenyl)-butyl]-aminoethyl]}-phenoxy-N-(3-nitrooxypropyl-1)-acetamide citrate hydrate; m.p. 141°-142° C. (decomp.).

EXAMPLE 49

2-Methoxy-5-{2-[N-methyl-N-[4-cyano-4-(methylethyl)-4-(3,4,5-trimethoxyphenyl)-butyl]-aminoethyl]}-phenoxyacetic acid 4-(nitrooxymethyl)-piperidylamide citrate hydrate; m.p. 139°-142° C. (decomp.).

EXAMPLE 50

2-Methoxy-4-{2-[N-methyl-N-[4-cyano-4-(methylethyl)-4-(3,4,5-trimethoxyphenyl)-butyl]-aminoethyl]}-phenoxyacetic acid 4-(α-nitrooxyethyl)-piperidylamide citrate hydrate; m.p. 143°-144° C. (decomp.).

EXAMPLE 51

2-Methoxy-4-{2-[N-methyl-N-[4-cyano-4-(methylethyl)-4-(3,4,5-trimethoxyphenyl)-butyl]-aminoethyl]}-phenoxyacetic acid 4-(nitrooxymethyl)-piperidylamide citrate hydrate; m.p. 142°-144° C. (decomp.).

EXAMPLE 52

2-Methoxy-4-{1-cyano-1-(methylethyl)-4-[N-methyl-N-[2-(3,4-dimethoxyphenyl)-ethyl]-aminobutyl]}-phenoxyacetic acid 4-(nitrooxymethyl)-piperidylamide citrate hydrate; m.p. 145°-147° C. (decomp.).

EXAMPLE 53

2-Methoxy-4-{1-cyano-1-(methylethyl)-4-[N-methyl-N-[2-(3,4-dimethoxyphenyl)-ethyl]-aminobutyl]}-phenoxyacetic acid 4-(α-nitrooxyethyl)-piperidylamide citrate hydrate; m.p. 143°–145° C. (decomp.).

EXAMPLE 54

3-{2-[N-Methyl-N-[4-cyano-4-hexyl-4-(3-methoxyphenyl)-butyl]-aminoethyl]}-phenoxy-N-(nitrooxyethyl)-acetamide oxalate hydrate; m.p. 134°–135° C. (decomp.).

EXAMPLE 55

3-{2-[N-Methyl-N-[4-cyano-4-hexyl-4-(3-methoxyphenyl)-butyl]-aminoethyl]}-phenoxy-N-(2-nitrooxypropyl)-acetamide oxalate hydrate; m.p. 136°–137° C. (decomp.).

EXAMPLE 56

2-Methoxy-4-{2-[N-methyl-N-[4-cyano-4-(methylethyl)-4-(3,4-dimethoxyphenyl)-butyl]-aminoethyl]}-phenoxy-N-(S(+)-2-nitrooxypropyl)-acetamide oxalate hydrate; m.p. 134°–135° C. (decomp.).

EXAMPLE 57

2-Methoxy-4-{2-[N-methyl-N-[4-cyano-4-(methylethyl)-4-(3,4-dimethoxyphenyl)-butyl]-aminoethyl]}-phenoxy-N-(R(−)-2-nitrooxypropyl)-acetamide oxalate hydrate; m.p. 126°–128° C. (decomp.).

EXAMPLE 58

2-Methoxy-4-{2-[N-methyl-N-[4-cyano-4-(methylethyl)-4-(3,4-dimethoxyphenyl)-butyl]-aminoethyl]}-phenoxy-N-[methyl-(2-nitrooxycyclohexyl)]-citrate hydrate; m.p. 144°–146° C. (decomp.).

EXAMPLE 59

2-Methoxy-5-{1-cyano-1-(methylethyl)-4-[N-methyl-N-[2-(3,4-dimethoxyphenyl)-ethyl]-aminobutyl]}-phenoxy-N-[methyl-(2-nitrooxycyclohexyl)]-acetamide citrate hydrate; m.p. 142°–143° C. (decomp.).

EXAMPLE 60

2-Methoxy-5-{2-[N-methyl-N-[4-cyano-4-(methylethyl)-4-(3,4-dimethoxyphenyl)-butyl]-aminoethyl]}-phenoxy-N-[methyl](2-nitrooxycyclohexyl)]-acetamide citrate hydrate; m.p. 80° C. (decomp.).

The phenoxyacetic acids required as starting materials are prepared in a manner analogous to that described in the preceding Examples.

It will be understood that the specification and examples are illustrative but not limitative of the present invention and that other embodiments within the spirit and scope of the invention will suggest themselves to those skilled in the art.

What is claimed is:

1. A phenylacetonitrile derivative compound of the formula

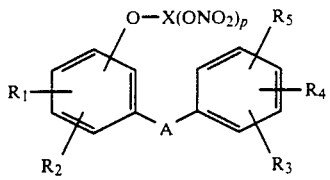

wherein $R_1$, $R_2$, $R_3$, $R_4$ and $R_5$, are the same or different and are hydrogen, fluorine, chlorine, bromine, $C_1$–$C_6$ alkyl, $C_1$–$C_6$ alkoxy, nitro, amino, or acylamino with up to 6 carbon atoms, or two adjacent substituents can together form methylenedioxy or ethylenedioxy, A is

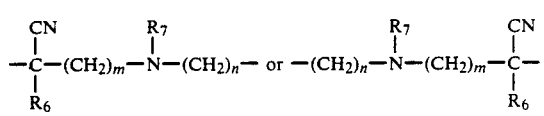

wherein $R_6$ is straight-chained, cyclic or branched, saturated or unsaturated alkyl containing 2 to 12 carbon atoms; $R_7$ is hydrogen or straight-chained or branched, saturated alkyl containing up to 6 carbon atoms; m is 2 or 3; n is 2 or 3; p is 1 or 2; and X is amino-substituted or unsubstituted straight-chained, cyclic or branched alkyl containing 2 to 10 carbon atoms, or is

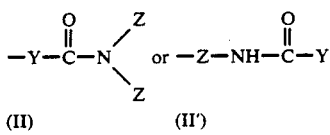

wherein Y and Z, which can be the same or different, are straight-chained or branched alkyl groups containing up to 8 carbon atoms or are monocycloalkyl or dicycloalkyl, alkyl-monocycloalkyl or alkyl-dicycloalkyl, or monocycloalkylalkyl or dicycloalkylalkyl groups, which groups are uninterrupted or interrupted by an oxygen or sulphur atom, and one of the groups Z can further be hydrogen or both Z groups are joined to form a ring containing 4 to 6 carbon atoms which is optionally interrupted by a further nitrogen or a further nitrogen which is substituted by alkyl or alkanoyl, the —O—NO$_2$ groups being substituents of Y as well as of Z; and the salts thereof with physiologically acceptable acids.

2. The compound of claim 1 wherein $R_2$, $R_4$ and $R_5$ are $C_1$–$C_6$ alkoxy, $R_3$ is hydrogen.

3. The compound of claim 2 wherein $R_2$, $R_4$ and $R_5$ are methoxy.

4. The compound of claim 2 wherein X is

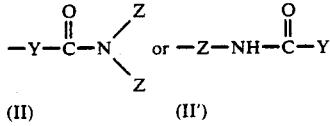

wherein Y and Z, are substituted with —O—NO$_2$ or are unsubstituted, can be the same or different, and are straight-chained or branched alkyl containing up to 8 carbon atoms or are monocycloalkyl, alkylmonocycloalkyl or monocycloalkylalkyl having 4 to 6 carbons and up to 2 nitrogens in the cyclic moiety, and up to 8 carbons in the alkyl moiety or one of the groups Z in general formula II is hydrogen or both Z groups are joined to form a ring containing 4 to 6 carbon atoms and up to one alkyl or alkanoyl substituted or unsubstituted nitrogen.

5. The compound of claim 1 having the formula

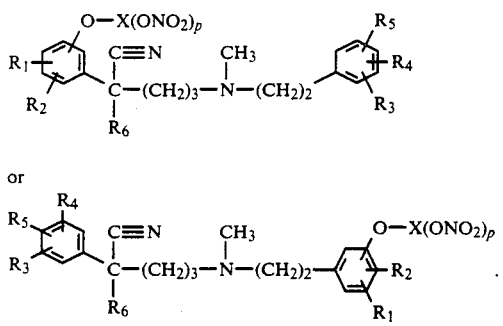

or

6. The compound of claim 5 wherein
$R_1$ is hydrogen
$R_2$ is —OCH$_3$
$R_4$ is —OCH$_3$
$R_5$ is —OCH$_3$
$R_6$ is —CH(CH$_3$)$_2$ 7. The compound of claim 5 wherein X is

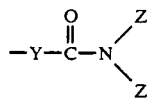

wherein both Z groups are joined to form a ring containing 4 to 6 carbon atoms and up to one alkyl or alkanoyl substituted or unsubstituted nitrogen.

8. The compound of claim 1 wherein X is

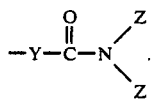

9. The compound of claim 1 wherein $R_1$, $R_2$, $R_3$, $R_4$ and $R_5$, are the same or different and are hydrogen, C$_1$-C$_6$ alkyl or C$_1$-C$_6$ alkoxy.

10. The compound of claim 1 wherein $R_1$, $R_2$, $R_3$, $R_4$ and $R_5$ are the same or different and are nitro, amino or acylamino with up to 6 carbon atoms.

11. The compound of claim 1 wherein $R_1$ and $R_2$ are adjacent substituents and together form methylenedioxy or ethylenedioxy.

12. The compound of claim 1 wherein $R_3$ and $R_4$ are adjacent and together form methylenedioxy or ethylenedioxy.

13. The compound of claim 1 wherein A is

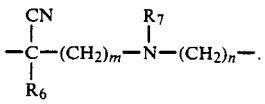

14. The compound of claim 1 wherein A is

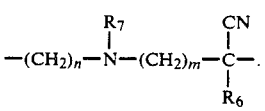

15. The compound of claim 1 wherein X is alkyl containing 2 to 10 carbon atoms.

16. The compound of claim 1 wherein X is amino substituted alkyl containing 2 to 10 carbon atoms.

17. The compound of claim 1 wherein X is

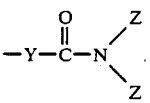

18. The compound of claim 1 wherein both Z groups are joined to form a ring containing 4 to 6 carbon atoms or a ring containing 4 to 6 carbon atoms and a further nitrogen.

19. The compound of claim 1 wherein Y and Z are alkyl groups containing up to 8 carbon atoms.

20. The compound of claim 1 wherein X is

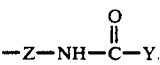

21. A pharmaceutical composition containing an effective amount of the compound of claim 1 to lower the blood preload pressure on the heart, for the treatment of heart and circulatory diseases, in admixture with pharmaceutically acceptable diluents or carriers.

22. A method for treatment of heart and circulatory diseases by reducing blood preload pressure of the heart, comprising administering an effective amount of the compound of claim 1.

23. The method of claim 22 wherein 50 mg to 500 mg per day per 75 kg of body weight, are administered.

* * * * *